US012121311B2

(12) United States Patent
Chi

(10) Patent No.: US 12,121,311 B2
(45) Date of Patent: Oct. 22, 2024

(54) METHODS AND SYSTEMS FOR ROBOTIC-ASSISTED SURGERY USING CUSTOMIZED BONE REGISTRATION GUIDES

(71) Applicant: Unik Orthopedics, Inc., San Jose, CA (US)

(72) Inventor: Charlie Wen-Ren Chi, Milpitas, CA (US)

(73) Assignee: Unik Orthopedics, Inc., San Jose, CA (US)

( * ) Notice: Subject to any disclaimer, the term of this patent is extended or adjusted under 35 U.S.C. 154(b) by 0 days.

(21) Appl. No.: 18/207,869

(22) Filed: Jun. 9, 2023

(65) Prior Publication Data

US 2023/0310097 A1 Oct. 5, 2023

Related U.S. Application Data

(63) Continuation of application No. 17/091,516, filed on Nov. 6, 2020, now Pat. No. 11,717,359.

(60) Provisional application No. 63/090,384, filed on Oct. 12, 2020, provisional application No. 62/933,874, filed on Nov. 11, 2019.

(51) Int. Cl.
*A61B 34/30* (2016.01)
*A61B 17/15* (2006.01)
*A61B 17/17* (2006.01)
*A61B 34/10* (2016.01)
(Continued)

(52) U.S. Cl.
CPC .......... *A61B 34/30* (2016.02); *A61B 17/1764* (2013.01); *A61B 34/10* (2016.02); *B25J 17/02* (2013.01); *A61B 2017/00212* (2013.01); *A61B 2017/00398* (2013.01); *A61B 2017/00477* (2013.01); *A61B 17/154* (2013.01); *A61B 17/1742* (2013.01); *A61B 17/1757* (2013.01);
(Continued)

(58) Field of Classification Search
CPC ....... A61B 17/15; A61B 17/154; A61B 17/17; A61B 17/1742; A61B 17/1746; A61B 17/175; A61B 17/1757; A61B 17/1764; A61B 2017/00212; A61B 2017/00398; A61B 2034/101; A61B 2034/105; A61B 2034/108; A61B 34/10; A61B 34/30
See application file for complete search history.

(56) References Cited

U.S. PATENT DOCUMENTS

2019/0388158 A1* 12/2019 Mahfouz ............ A61B 17/1764

* cited by examiner

*Primary Examiner* — Samuel S Hanna
(74) *Attorney, Agent, or Firm* — Polsinelli PC; Derek D. Donahoe

(57) ABSTRACT

Described within are systems, methods and apparatus for a bone mounted robotic-assisted orthopedic surgery system for precise implant position, soft tissue balancing and guidance of tools during a surgical procedure, particularly partial or total knee replacement procedure. The system features a bone mounted robotic arm with end-effector for precise positioning of surgical tool, position in of implants and balancing of soft tissues. The reconfigurable robotic system requires minimal training by surgeons, is intuitive to use similar to conventional instrumented surgery and has a small footprint. The system works with existing, conventional instruments, patient specific instruments, sensor-assisted systems and computer-assisted systems and does not require increased surgical time and safely provides the enhanced precision achievable by robotic-assisted systems and computer-assisted technologies.

10 Claims, 44 Drawing Sheets

(51) Int. Cl.
*B25J 17/02* (2006.01)
*A61B 17/00* (2006.01)
(52) U.S. Cl.
CPC ... *A61B 2034/105* (2016.02); *A61B 2034/108* (2016.02); *A61B 2034/301* (2016.02)

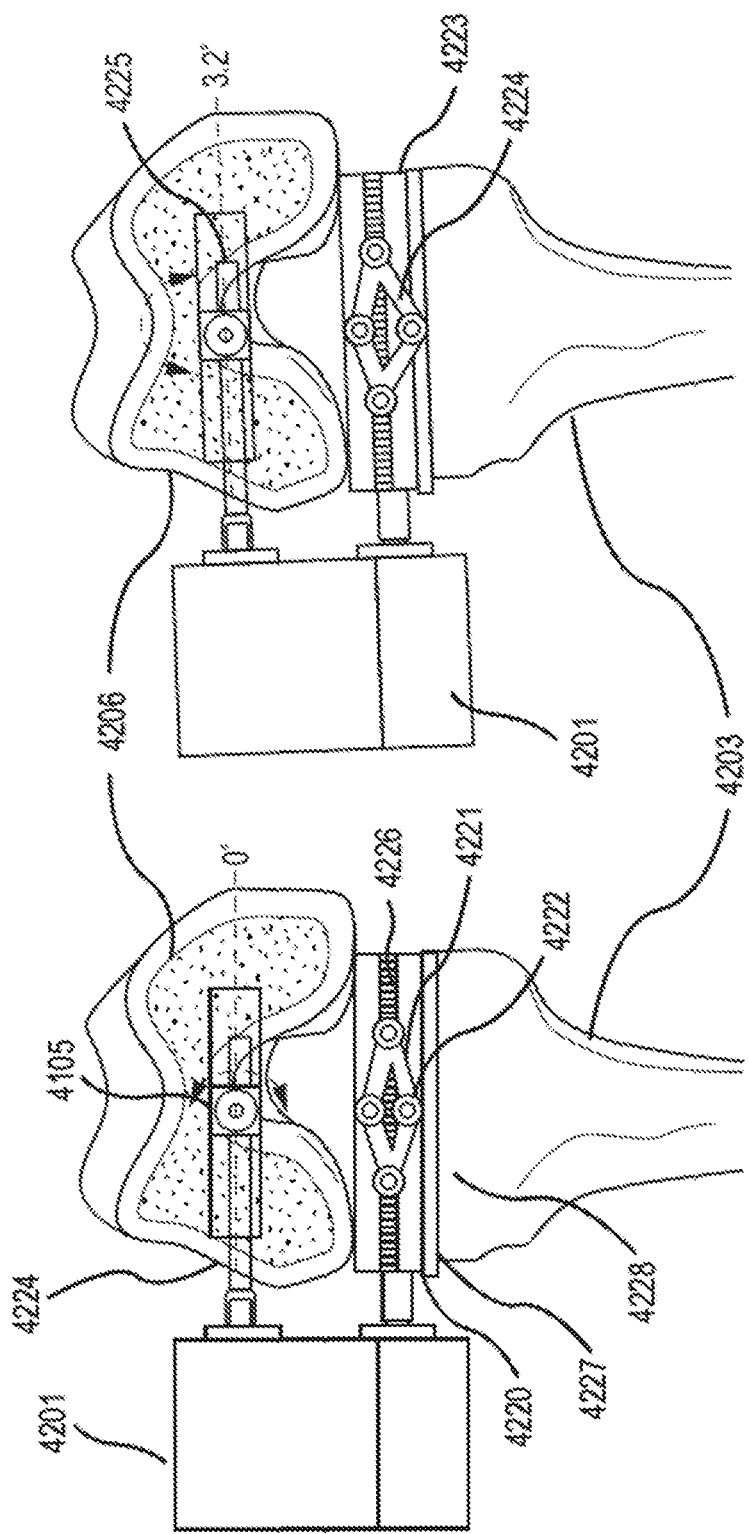

METHODS AND SYSTEMS FOR ROBOTIC-ASSISTED SURGERY USING CUSTOMIZED BONE REGISTRATION GUIDES

RELATED APPLICATIONS

This application is a continuation of and is related to U.S. Nonprovisional patent application Ser. No. 17/091,516, filed Nov. 6, 2020 entitled "METHODS AND SYSTEMS FOR ROBOTIC-ASSISTED SURGERY USING CUSTOMIZED BONE REGISTRATION GUIDES," which claims priority under 35 U.S.C. § 119(e) from U.S. Patent Application No. 62/933,874, filed Nov. 11, 2019 entitled "BONE-MOUNTED ROBOTIC-ASSISTED SURGICAL SYSTEMS," and from U.S. Patent Application No. 63/090,384, filed Oct. 12, 2020 entitled "ROBOTIC-ASSISTED SURGERY USING CUSTOMIZED BONE REGISTRATION GUIDES," both of which are hereby incorporated by reference in their entirety.

TECHNICAL FIELD

Embodiments of the present disclosure generally relate to systems and methods for creating and utilizing customized arthroplasty registration guides in joint replacement procedures. More specifically, the present disclosure relates to methods for creating arthroplasty registration guides customized to a particular patient for use in robot-assisted surgical procedures that provide three-dimensional reference information of the patient to the surgical robot to orient a surgical plan for execution by the surgical robot, including bone-mounted surgical robots.

BACKGROUND

Through repeated heavy lifting, traumatic events, bone disease and/or arthritis, a patient's joints, such as knee, hip, shoulder and ankle may become degenerated, damaged or loosened to the point that pain or paralysis does not respond to medication or other forms of non-surgical treatments. One type of procedure to address damage to a person's joint is a total or partial joint arthroplasty procedure. Arthroplasty is a medical procedure where a joint of a patient is replaced, remodeled, or realigned, often done to relieve pain in the joint after damage. Damage to the joint may result in a reduction or wearing away of cartilage in the joint area, which operates to provide frictional, compressive, shear, and tensile cushioning within the joint. As such, reduction in cartilage in a joint causes pain and decreased mobility of the joint. To combat this joint pain, a patient may undergo the arthroplasty procedure to restore function and use back to the damaged joint.

A joint replacement procedure generally involves removing parts of an arthritic or damaged joint and replaced with a metal, plastic or ceramic device called prosthesis. The prosthesis or implant is designed to replicate the movement of a normal, healthy joint. For example, the damaged ball (the upper end of the femur) is replaced with a metal ball attached to a metal stem that is fitted into the femur and a plastic socket is implanted into the pelvis, replacing the damaged socket. In addition, a balance joint contributes to improved alignment and stability. Ligament balancing helps reduce wear and loosening of the joint. A patient with a balanced joint is more likely to have increased range of motion and proprioception, and decreased pain. All these factors help minimize the need for revision surgery.

Several types of arthroplasty procedures are known, including total and partial knee arthroplasty, total and partial hip arthroplasty, total and partial shoulder arthroplasty, and spinal fusion procedures, and the like. In general, joint arthroplasty (JA) procedures involve replacing the diseased or damaged portion of the bones of the joint with metal or plastic components that are shaped to approximate the shape of the replaced portion or shaped to allow movement of the joint and relieve the joint pain. For example, a total knee arthroplasty (TKA) procedure may include replacement of a portion of the femur and a portion of the tibia that make up the knee joint. Similar procedures may be performed on other damaged joints, such as a hip, a shoulder, an elbow, and the like. General discussion of arthroplasty procedures herein are directed specifically to TKA-type procedures, but may be applied to arthroplasty procedures of other types of joints.

In a TKA procedure, a damaged portion of the distal region of the femur is removed and replaced with a metal or plastic component that is shaped to mirror or approximate the replaced portion. The metal or plastic component may be impacted onto the femur or fixed using a type of surgical cement or other fastening system. Further, a proximal portion of the tibia may also be removed and replaced with a generally flat metal or plastic component that is shaped to mirror or approximate the replaced portion. The tibia replacement implant may also be attached to the tibia through impaction onto the bone or fixed using a type of cement. In general, the femur implant and the tibia implant are mated to form a joint that approximates the shape and operation of the knee joint. In some examples, a plastic surface is placed between the femur implant and the tibia implant to prevent metal-on-metal interaction between the implants during use of the replaced joint.

As mentioned above, arthroplasty procedures often involve the removal and replacement of portions of the bones that make-up the injured joint. During the removal, the portions of the bones may be cut, drilled, resurfaced, and the like to create a surface on the bones that mates with the respective implants. In one particular example of a TKA procedure, the ends of the bones (distal end of the femur and proximate end of the tibia) may be completely removed to create a generally flat surface to which the implants are mated. Once the mating surfaces for the implants are created on the receiving bones, the implants may then be attached to the bones as described above.

Although the broad outline of the arthroplasty procedures is described above, there is much to consider when performing the procedure. For example, patients may undergo a preoperative planning phase of the procedure through one or more consultations with a doctor that could last a month or more before the arthroplasty surgery is performed. In addition, alignment of the implants in the joint with the rest of the patient's anatomy is crucial to the longevity of the implant and the implant's effectiveness in counteracting the pre-surgery joint condition. Methods have been developed over time in attempts to improve the effectiveness of the arthroplasty procedure and prevent or reduce post-surgery complications. On one end of the spectrum, surgeons may "free-hand" the resection or resurfacing of the bones of the joint create the surface for mating with the implants. However, as should be appreciated, this approach may not be as accurate as other procedures. In another example, systems and methods have been developed to produce customized arthroplasty cutting jigs that allow a surgeon to quickly and accurately perform the necessary resections of the bones that result in a successful arthroplasty procedure. In particular, cutting jigs may be generally customized for the particular patient's joint undergoing the arthroplasty procedure to ensure that the implants align with the patient's anatomy post-procedure. Through the use of such customized cutting jigs, the arthroplasty procedure is both more accurate (ensuring more longevity to the implants) and quicker (reducing the time required for the surgical procedure, thereby reducing the potential for post-surgery complications).

In yet another example, surgery-assisting robots or other robotic-like devices have been developed to assist the surgeon in performing the arthroplasty procedure. Aspects of the approved surgical plan may be uploaded to the robotic-assisting device for assisting the surgeon during the procedure. In some instances, the surgery-assisting robot may perform the resection or resurfacing of the bones, either through the guidance of the surgeon or alone through automatic executing one or more aspects of the arthroplasty procedure. In still other instances, combinations of procedures may be utilized to perform the arthroplasty procedure. For example, a surgeon may use a customized arthroplasty cutting jig to verify a cut plane or resection of the bone, but the resection or resurfacing may be done by the surgery-assisting robotic device. In another example, the surgeon may free-hand the resection with some guidance provided by the robotic device.

Regardless of the method utilized, several drawbacks may exist for the various procedures performed. For example, the preoperative planning phase of the procedure may involve multiple consultations with a doctor, scans or images taken of the patient, generation of the surgical plan, review and approval of the surgical plan by the surgeon, and time to generate the customized arthroplasty guide for use in the surgery. This pre-operative time may last several months over which the patient may experience pain and discomfort waiting for the arthroplasty procedure. In addition, robotic surgical equipment may be cost prohibitive for many health care providers, ranging into several million dollars. These costs may further increase for procedures that utilize one or more disposable instruments (such as disposable or one-use movement tracking devices utilized by some robotic surgical equipment) that incur an additional cost to the health care provider. The high cost and long lead time associated with some arthroplasty procedures make it undesirable for some patients that would otherwise benefit from such procedures.

In addition, one of the goals of computer-assisted robotic surgery (CARS) is to improve the accuracy and clinical outcome with which a given orthopedic procedure can be performed compared to conventional methods. Current methods of robotic-assisted orthopedic surgery has its advantages in terms of accuracy and precision, surgical efficiencies, operative time, minimally invasiveness and cost-effectiveness. One of the main disadvantages is its technological complexity compared to conventional surgery, which leads to a large increase in potential sources of surgical error. Some of these technological errors may be difficult for the inexperienced surgeon to recognize; therefore, poor outcomes may occur if the technology is relied upon the robot technician or blindly. Other disadvantages of robot-assisted surgery relative to conventional instrumentation methods include the cost of trainings the entire surgical team in robotic surgery, time-consuming learning curve associated with the adoption of new technology and the high cost of the robotic surgical system itself.

It is with these and other issues in mind that various aspects of the present disclosure were developed.

SUMMARY

One implementation of the present disclosure may take the form of robotic device for performing an arthroplasty procedure. The robotic device may include a base unit comprising a plurality of link joints each in mechanical communication with one of a plurality of activators, a processing device, and a non-transitory computer-readable medium encoded with instructions, which when executed by the processing device, cause the processing device to control the plurality of activators according to a joint arthroplasty procedure. The robotic device may also include a mounting device in mechanical communication with a first link joint of the plurality of link joints and comprising a first configurable link to orient the base unit corresponding to the joint arthroplasty procedure, the mounting plate mounted to a patient's anatomy via a customized registration device and a configurable resection guide in mechanical communication with a second link joint of the plurality of link joints and comprising a second configurable link to orient the resection guide corresponding to the joint arthroplasty procedure.

Another implementation of the present disclosure may take the form a method for performing an arthroplasty procedure. The method may include receiving a plurality of two-dimensional images of a patient's joint the subject of the arthroplasty procedure, generating, based on locating a plurality of mating shapes within the plurality of two-dimensional images of the patient's joint, a customized registration guide for the patient's joint for use during the arthroplasty procedure, and mounting, using the customized registration guide, a robotic device on the patient's anatomy. The robotic device may include a mounting device mounted to the patient's anatomy, a first link joint of a base unit in mechanical communication with the mounting device to orient the base unit corresponding to the joint arthroplasty procedure, and a configurable resection guide in mechanical communication with a second link joint of the base unit and oriented to provide a resection guide for the joint arthroplasty procedure.

BRIEF DESCRIPTION OF THE DRAWINGS

The various features and advantages of the technology of the present disclosure will be apparent from the following description of particular embodiments of those technologies, as illustrated in the accompanying drawings. It should be noted that the drawings are not necessarily to scale; however the emphasis instead is being placed on illustrating the principles of the technological concepts. The drawings depict only typical embodiments of the present disclosure and, therefore, are not to be considered limiting in scope.

FIGS. 42B-42F are illustrating an example of an intra-operative soft-tissue ligament balancing using a 3-DOF robot and a scissor jack in accordance with one embodiment.

DETAILED DESCRIPTION

Figure 1:
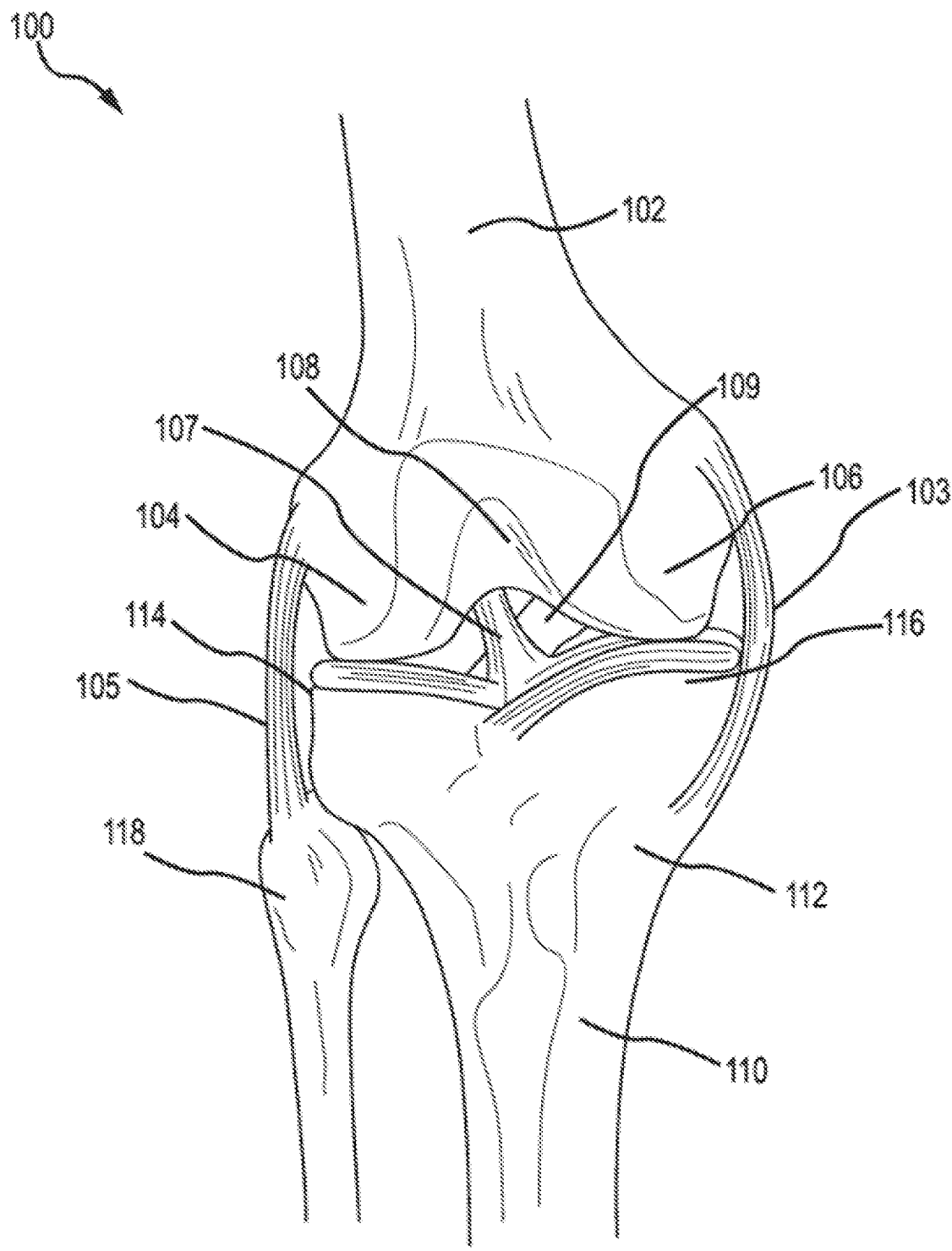
FIG. 1 is a frontal or coronal view of the human knee.

The present disclosure relates to systems and methods for a miniature bone-mounted robotic-assisted surgery system for treating patients suffering from joint disorders. For ease of discussion, the present disclosures are focused on knee procedures, but can be applied to other joints, such as hip, shoulder, elbow and ankle, as well as, spinal procedures, such as fusion. Some of the common types of knee procedure are as follows:

Total knee replacement
Partial or uni, bi-compartment knee replacement
Patella-femoral resurfacing
Osteotomies
Revision knee surgery Aspects of the present disclosure include systems, methods, computing devices, and the like for performing an arthroplasty procedure utilizing a customized registration guide for mating with a patient's anatomy and providing registration information to a surgery-assisting robotic device. Through the systems and processes described herein, a faster, cheaper, and more accurate robotic-assisted arthroplasty procedure may be performed utilizing the registration guide. In particular, a customized registration guide may be generated or created from a plurality of 2D images of a patient's anatomy. The registration guide may include one or more mating surfaces that mate with particular locations on the patient's bone of the damaged joint. Further, the generation of the registration guide may not require the approval of a surgical plan before being generated as the registration guide is based on the patient scans or images and does not include an indication of a resection plane or resurfacing information. During the arthroplasty procedure, the registration guide may be mated with the patient's bone, either by a surgeon or by the robotic device, and a location in three-dimensional space of the registration guide may be obtained for the robotic device. The robotic device may therefore determine the location of the patient anatomy without a registration process requiring a probe or a surgeon to locate particular locations on the patient's bone to provide the patient orientation to the robotic device. Rather, the registration device may attach to the robotic device and, because the dimensions of the registration device may be known, the location and orientation of the patient's anatomy may similarly be known. The location of the patient's anatomy may then be mapped to the surgical plan for resection and/or resurfacing by the robotic device.

In another implementation, the customized registration device may provide for attaching a bone-mounted robotic system for assisting total and partial knee procedures in resection of the patient's bone replaced by knee prosthesis of the same joint. The advantages of a bone mounted robotic-assisted surgery system, compared with a free standing or bed-mounted surgical robot, are such that once intra-operative registration is completed, motion tracking is not required since the robot moves with the patient's joint. In addition, the size and complexity of the robot may be reduced as the robot is designed for a particular workspace of each joint procedure compared to a general robot that can perform in different workspaces. Smaller and less expensive robotic-assisted surgery systems are attractive for many reasons including cost, ease of use, faster learning curve, less training required for the whole surgery staff and space limitations due to smaller operating rooms such as ambulatory surgery centers (ASCs).

In general, mounting the robot on the patient's anatomy based on a target implant size and position can be accomplished using several techniques, including but not limited to mechanical instrumentation, computer navigation or patient specific jig. For image-based systems that use X-rays, MRI CT scans, or other two-dimensional (2D) images pre-operatively, the registration process may include identifying bony landmarks in 2D image(s) or on virtual surface bone model. During the surgical procedure, computer navigation or patient specific guide (physical contact points) can be used for registering the robot to the actual patient's bone in the imaging data or for registering a position and/or orientation of the patient in the operative space relative to a standalone robot device. For imageless system, the bony landmarks may be identified intraoperatively by the surgeon using either computer navigation system, sensor-based instrumentation, or mechanical instrumentation. For both image and image-less systems, the registration process provides the robot's position and orientation in three-dimensional space along (X,Y,Z) axes relative to the patient's position, orientation and/or anatomical axes.

In another aspect of the present disclosure, one or more inertial sensors may be provided with a bone-mounted robotic system or separate from the robotic system for tracking of patient movement. Other aspects may include a mechanical fixture with locking system and/or mechanical protractors for intra-operative soft-tissue ligament balancing and leg alignment measurement. For example, after the implant position has been determined, static and/or dynamic soft-tissue balancing may be initiated. In static soft-tissue gap balancing, the knee is placed in full-extension (straight) and flexed to approximately 90 Degrees (femoral shaft to tibial shaft) to measure any gap imbalance. In dynamic-soft tissue gap balancing, a common femoral axis of rotation between the femoral and tibial joint line and patella-femoral joint line may be identified to model the kinematic motion of the knee and real-time adjustments to be made to obtain a correct knee kinematics and soft-tissue balancing. Subsequently, correction to the bone resection can be made using the robotic device to reproduce a desired bone spacing (extension and flexion gaps) and implant size during implantation.

In another aspect of the present disclosure may provide a robotic-assisted surgical system used during the joint procedure. The system may include a robotic device, computer, transceiver, monitor, and/or other apparatus, such as power tools, monitoring equipment, or robots. The computer part of the system may provide real-time data and communication to the robotic device during a procedure. However, it is not required for the operation of the robot as the robot may be bone-mounted or may be a stand-alone device with internal microprocessor, embedded firmware, sensor, memory and power supply.

In some instances and through the registration devices described herein, the use of optical locators in the arthroplasty procedure may be eliminated, thereby reducing the costs for performing the procedure to the patient and health care facility. The registration device may also provide a more accurate registration procedure than previous registration procedures. Further, one or more movement sensors may be mounted on or otherwise associated with the patient's anatomy that wirelessly transmit patient movement to the robotic device for adjustments to the determined location/orientation of the cut plane in relation to the patient's bone. The use of movement sensors, such as one or more inertial sensors, may be more accurate than optical sensors for detecting the movement of the patient due to the sensitivity of the sensors, further increasing the effectiveness of the arthroplasty procedure. The registration guide and inertial sensors may be utilized with any type of arthroplasty procedures, including procedures for knees, hips, shoulders, spine, etc. In some instances, virtual reality systems may be incorporated into the systems described to aid the surgeon in performing one or more aspects of the arthroplasty procedure. These and all other arthroplasty procedures may benefit through the systems and methods described herein.

There has thus been outlined, rather broadly, some of the features of the methods and systems of a robotic-assisted surgery system using a customized registration device for arthroplasty procedures. Additional features of the methods and systems for the robotic-assisted surgery system are also discussed herein, such as, fixture and locking systems, sensors (force and inertial sensors) for robot registration, real-time monitoring and communication, and intra-operative knee modeling for soft-tissue ligament balancing and limb alignment measurement. In this respect, it is to be understood that the methods and systems for the robotic-assisted surgical system are not limited in its application to the details of construction or to the arrangements of the components set forth in the following description or illustrated in the drawings. The methods and systems described herein are capable of other aspects and of being practiced and carried out in various ways. Also, it is to be understood that the phraseology and terminology employed herein are for the purpose of the description and should not be regarded as limiting.

As mentioned, aspects of the present disclosure involve methods and systems for a robotic-assisted surgical systems. To aid in the description below, a brief discussion of the anatomy of the human knee is now included. As mentioned above, the present disclosure may be applied to any region of a patient's joint as part of the orthopedic procedure. However, for ease of understanding, the discussion herein is limited to particulars of the knee as an example of the inventions relating to the present disclosure procedure and embodiments.

FIG. 1 illustrates a coronal or frontal view 100 of the patient's knee joint comprising the femur 102 and tibia 110 bone interconnected by four ligaments. The ligaments are called the medial collateral ligament (MCL) 103, the lateral collateral ligament (LCL) 105, the anterior cruciate ligament (ACL) 107 and the posterior cruciate ligament (PCL) 109. Other soft tissue and knee capsule surrounds the knee joint with fluid filled cavities and fat. The ligaments along with the patella tendon 202 provide knee stability during standing, walking and running. The ends of the femur 102 include cartilage typically 1-7 mm thick on a healthy adult knee, which acts as a bearing surface supporting the medial condyle 106, lateral condyle 104, and patella groove 108. The corresponding tibia 110 with medial plateau 116 and lateral plateau 114 also includes thick cartilage typically 3-7 mm on a healthy adult knee that act as shock absorbers along with the meniscus and bearing surface. The lateral tibia is further supported by the fibula 118 that provides additional stability in terms of load bearing, spring, damper and shock absorption. In addition, the LCL is connected to the fibula 118 head with 1-2 mm slack or loosening. This allows the knee to rotate (pivot) and slide more freely without any binding or resistance. When the cartilage of the knee joint is worn away, pain may occur when the nerve endings of the femur 102 and tibia 110 bones touch each other.

Figure 2:
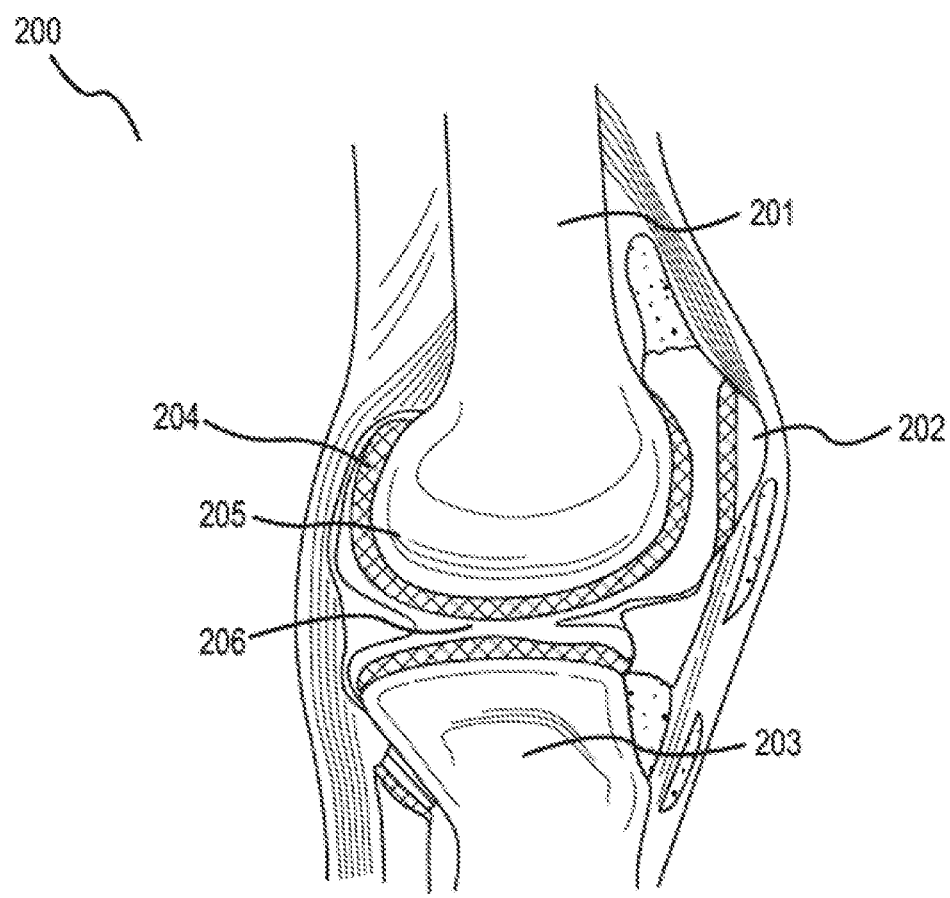
FIG. 2 is a lateral or sagittal view of a human knee.

FIG. 2 illustrates a sagittal or lateral view 200 of the patient's knee joint 206 comprising the lateral femur 201 and lateral tibia 203. The patella 202 sits on the anterior femur 201 in extension. As the knee bends or flexes, the patella 202 travels along the patella groove 108 and stops near the center of the knee. Surrounding the knee joint are tissues, such as muscles, fat, and ligaments and fluid that fills the cavity allowing the knee to have full extension and bending motion due to the folds within the capsule. The posterior condyle 205 with corresponding cartilage 204 is elliptical in shape in order to allow the knee to flex or bend with ease. In a healthy knee, the bone/cartilage on the femur 201, tibia 203 and patella 202 surface provide the ligament tension and stability needed during knee motion. When the cartilage surface is damaged or worn away, however, the knee joint may become painful, loose, and/or unstable. In some instances, a partial or total knee replacement may be performed to restore the knee stability and soft-tissue ligament balance and eliminate any pain. It's often critical to restore the balance and stability of the knee after surgery in order to extend the life of the prosthesis without requiring a second surgery, also known as a revision or manipulation of the soft tissue under anesthesia.

Figure 3:
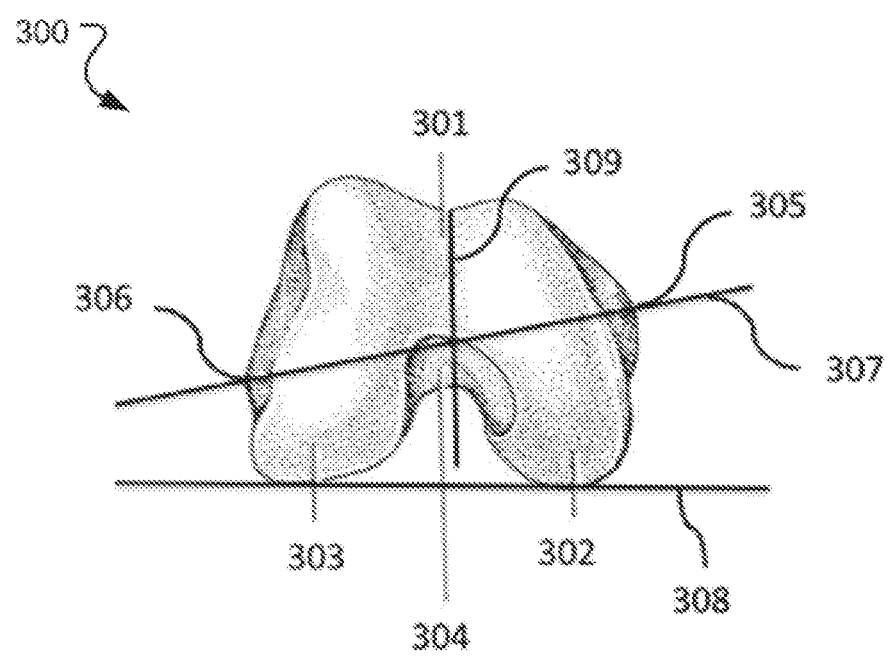
FIG. 3 is a transverse or axial view of a human femur.

FIG. 3 illustrates the axial or transverse view 300 of the patient's knee including the patella groove 301, medial condyle 302, and lateral condyle 303. The LCL 105 is shown attached to the lateral epicondyles 306 and the MCL 103 is attached to the medial epicondyles 305. The ACL and PCL are attached inside the femoral notch 304 on the medial 302 and lateral 303 condyles in a crisscross pattern, which is dome shaped allowing the ligaments to tension the knee in extension and flexion. A rotational axis can be established using the medial and lateral bone prominences of the femur (epicondyles) called the trans-epicondylar axis 307. Other axes can also be defined as well, such as the anterior-posterior (AP) axis 309, patellafemoral and posterior condylar axis 308. These axes are used during the total knee replacement procedure to assist the surgeon in establishing the proper orientation of the prosthesis. Malrotation of the knee prosthesis could result in the loss of knee flexion, pain due to ligament imbalance and premature failure requiring revision surgery. Therefore, it is useful to balance the soft tissue surrounding the knee joint in both extension and flexion, mimicking the bending motion and correct implant position and size.

Figure 4:
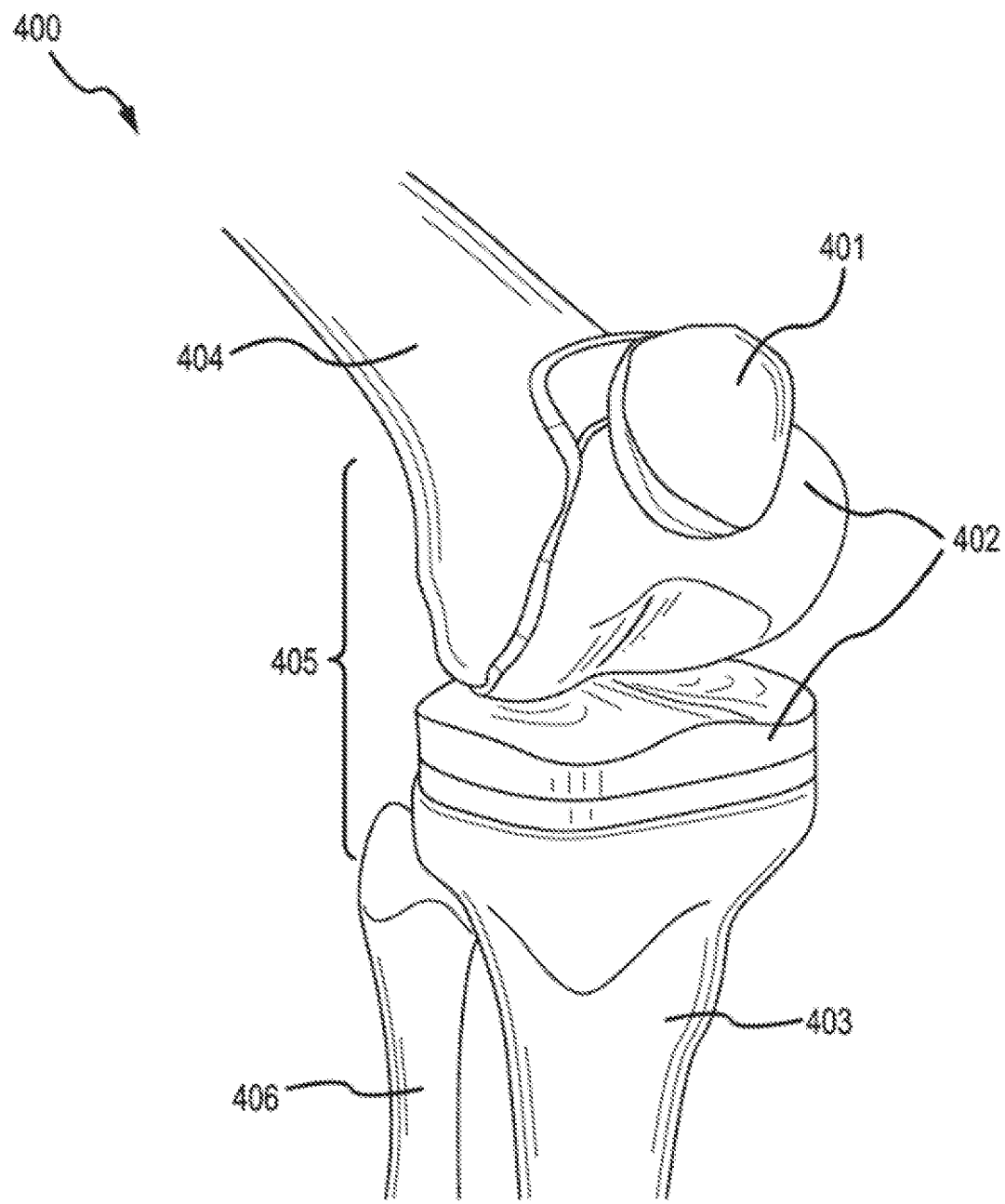
FIG. 4 is an isometric view of a total knee replacement procedure with corresponding prosthesis.

FIG. 4 is an isometric view 400 of a patient's knee 405 with corresponding prosthesis 402 after a total knee procedure. During the procedure, the bone and cartilage at the end of the femur 404 and tibia 403 are removed and replaced with metal and plastic components 402. In addition, the patella's bone and cartilage 401 may also be replaced with metal and/or plastic components. Typically, the prosthesis 402 are either cemented or press fitted to the bone for long-term fixation. The goal of a total knee replacement procedures is to replace the worn cartilage/bone surface with prosthesis 402 in order to subside the pain by removing the nerve endings of the femur 404 and tibia 403 bone. In order to preserve as much healthy bone as possible and also maintain the structural integrity and functionality (shape) of the knee, minimum amount of bone is removed using an oscillating saw and cutting guide based on the internal geometry of the prosthesis 402. For a standard, off-the-shelf prosthesis, the number of implant sizes are limited due to the instrumentation needed for each size and cost to manufacture and maintain a large implant inventory. For example, for a particular implant brand with a certain size (height and width dimensions), a corresponding cutting guide is needed to make the appropriate cuts to minimize bone removal. For example, most modern knee implant system are available in about 8-12 different sizes to cover the entire patient demographics compared to custom implants, which are designed or customized for each individual patient's knee.

Figure 5:
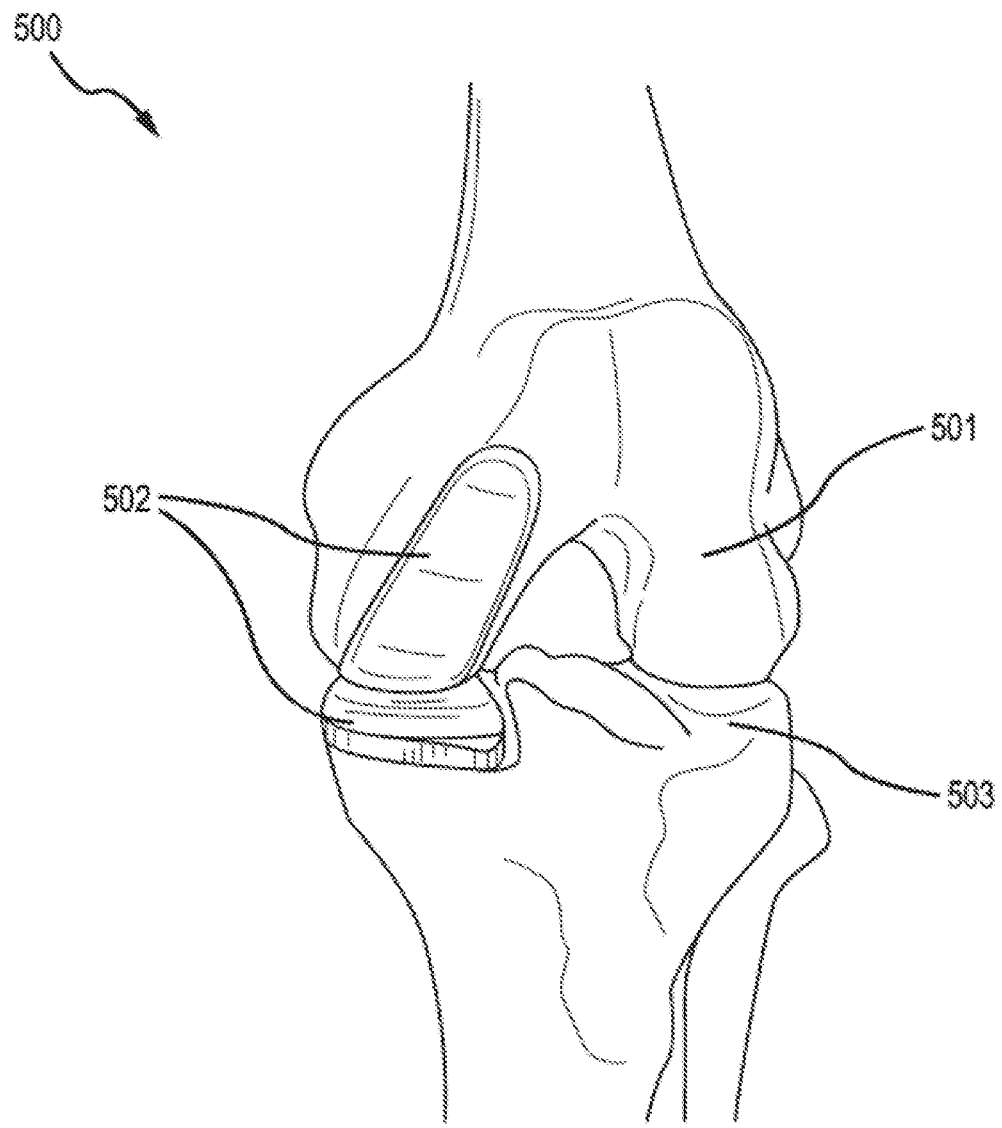
FIG. 5 is an isometric view of a partial or uni-knee replacement on the medial compartment with corresponding prosthesis.

FIG. 5 is an isometric view 500 of a partial or uni knee replacement on the medial compartment with corresponding prosthesis 502 of metal and plastic components. Depending on the locations of the damaged knee, other compartmental knee replacements are also possible. For example, the lateral compartment may include the lateral femoral condyle 501 and lateral tibial plateau 503. Other bi-compartmental replacements, such as the patella groove 301 and either the medial 302 or lateral 303 condyle may be replaced or any combination of patella, medial, and lateral condyle. A tri-compartmental is the same as a total knee replacement. As with total knee replacement, the goal is to preserve as much healthy bone as possible in case a revision or total knee replacement is needed in the future. Only the worn bone and cartilage are removed while preserving healthy bone/cartilage.

Figure 6:
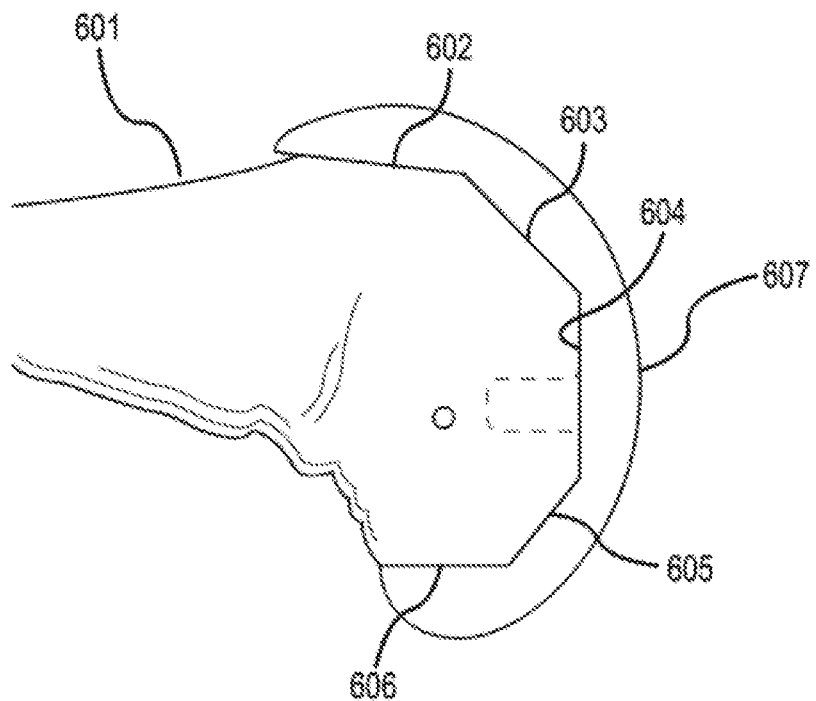
FIG. 6 is an illustration of a total knee prosthesis with internal geometry replacing the end of the femur bone where damaged occurred.

FIG. 6 is an illustration of a total knee prosthesis 607 with internal geometry replacing the end of the femur bone 601 where damaged occurred. As shown in FIG. 4 and described above, the implants for the femur and tibia are three-dimensional. For ease of discussion the internal geometry of prosthesis 607 is represented by lines in FIG. 6; but in reality, the prosthesis may be comprised of a series of connected planes. In one implementation and in order to minimize the amount of bone removed and to accommodate severe cartilage and bone loss, the internal geometry and thickness of the implant may include five geometric cuts (planes) called distal or primary 604, posterior 606, anterior 602, posterior chamfer 605, and anterior chamfer 603. For most implant manufacturers, the number of internal geometries may be the same, except the dimensions (height and width) of 607 varies for each size. For example, the height of distal plane 604 may vary for different sizes while all other internal geometric planes 602, 603, 605 and 606 may be the same. In one embodiment, the internal geometry of the prosthesis 607 may be different for different sizes. For example, in the case of custom implants, it is possible to have more or less internal geometries, thicknesses or smooth and continuous profiles matching the circular shape of the distal femur 601. In other embodiments, the internal geometry and size of implants are different for each manufacturer of implants. Therefore, conventional instrumentation provided by the implant manufacturer for making bone resections to match the internal geometries may be specific to each manufacturer.

Figure 7:
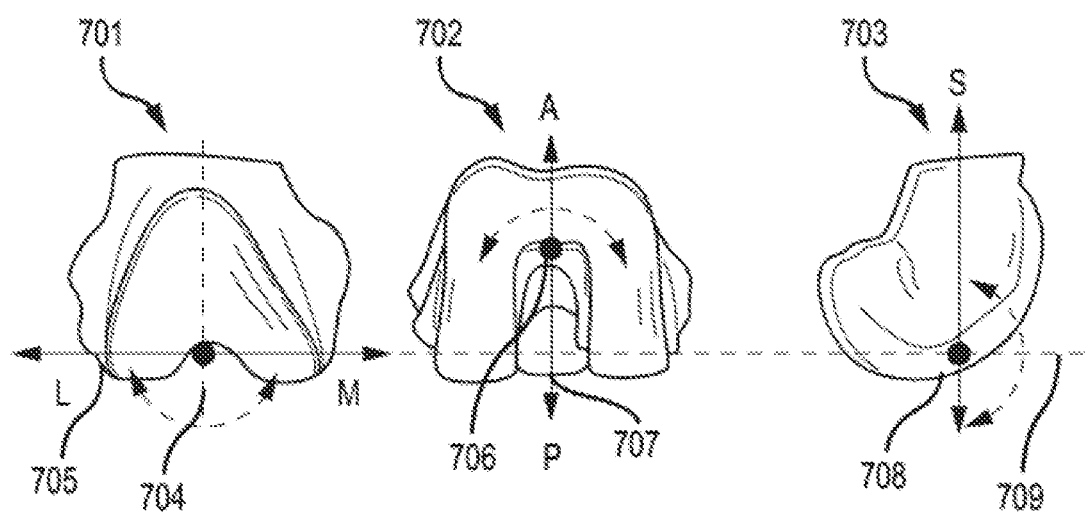
FIG. 7 are illustrations of the total knee in all three true anatomical views (coronal, axial and sagittal).

FIG. 7 is an illustration of the femur with corresponding prosthesis shown in three different planes: a coronal plane 701, an axial plane 702, and a sagittal plane 703. In some instances, the bone resection of the distal femur matching the internal geometries of the prosthesis determines the implant position and orientation in each plane. For example, in the coronal plane 701, the distal line 604 of FIG. 6 is a plane 705 that determines the yaw (varus/valgus rotation) angle and superior/inferior position of the implant relative to the center of the knee defined by line 704. Similarly, in the axial plane 702, the posterior line 606 is a plane 707 that determines the roll (internal/external rotation) angle and anterior/posterior position of the implant relative to the center of the knee defined by line 707. Lastly, in the sagittal plane 703, the distal line 604 is a plane 705 that determines the pitch (flexion/extension rotation) angle and superior/inferior position of the implant relative to the center of the knee defined by 708. The remainder of the geometries: anterior plane 602, anterior chamfer 603, and posterior chamfer 605 are based on the position of the implant defined by the distal plane, internal/external rotation and size.

Figure 8:
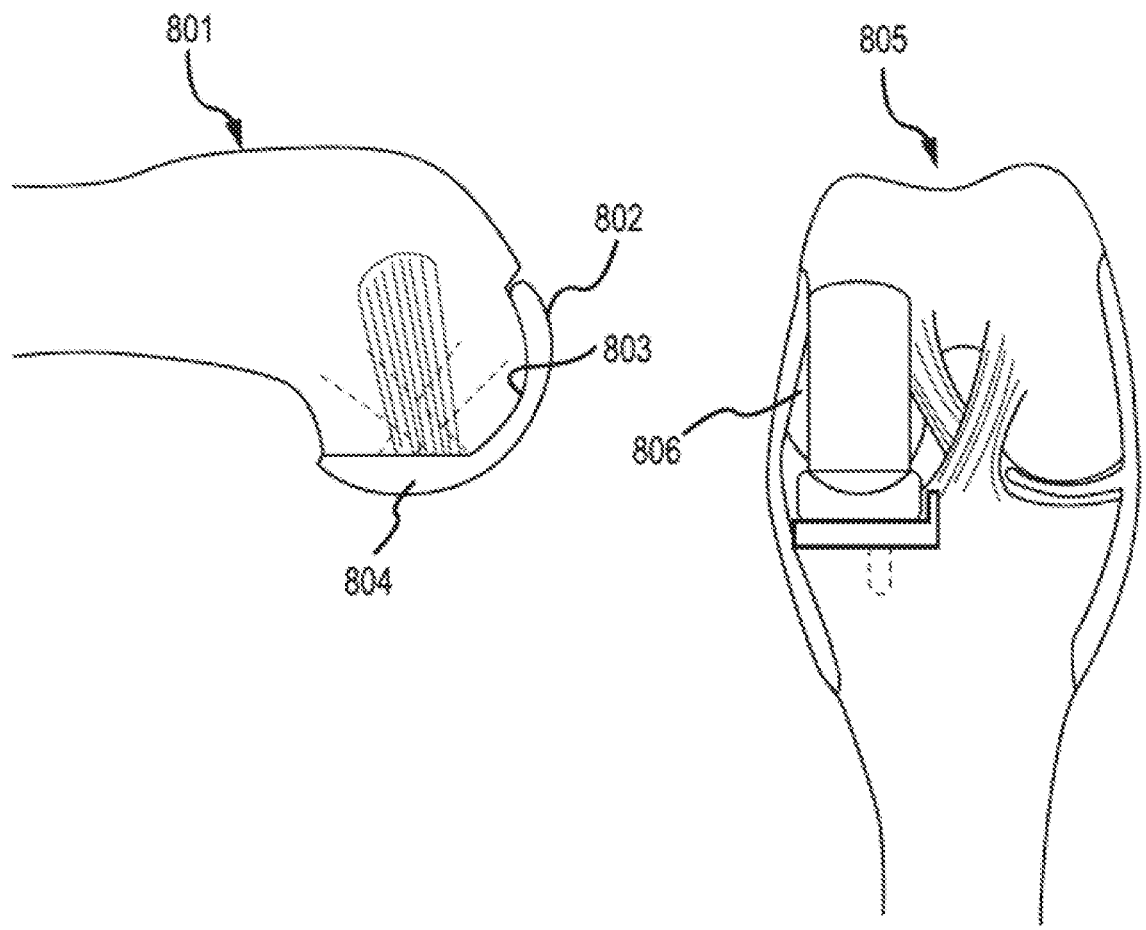
FIG. 8 are illustration of a uni-knee in two views (sagittal and axial).

FIG. 8 is an illustration of a uni-knee prosthesis 802 with continuous internal geometry 803 replacing the medial compartment 805 of femur bone 801 where the damaged bone/cartilage occurred. The internal geometry 803 is typically elliptical in terms of the profile matching the shape of the femoral condyle 205 follow by the straight posterior cut 804. The partial knee implant 802 is better suited for patients with minor cartilage/bone damage. In order to maintain the joint line of the femur (shown as line 206 of FIG. 2), the amount of cartilage/bone removed should match the thickness of the implant 802. In addition, the position and orientation of the implant in sagittal plane 802 and axial plane 806 should match. In one embodiment, the lateral compartment of the knee may be damaged and replaced with uni-knee prosthesis. In other embodiment, both medial and lateral sides are replaced with uni-knee prosthesis called bi-lateral uni-knee replacement.

Figure 9:
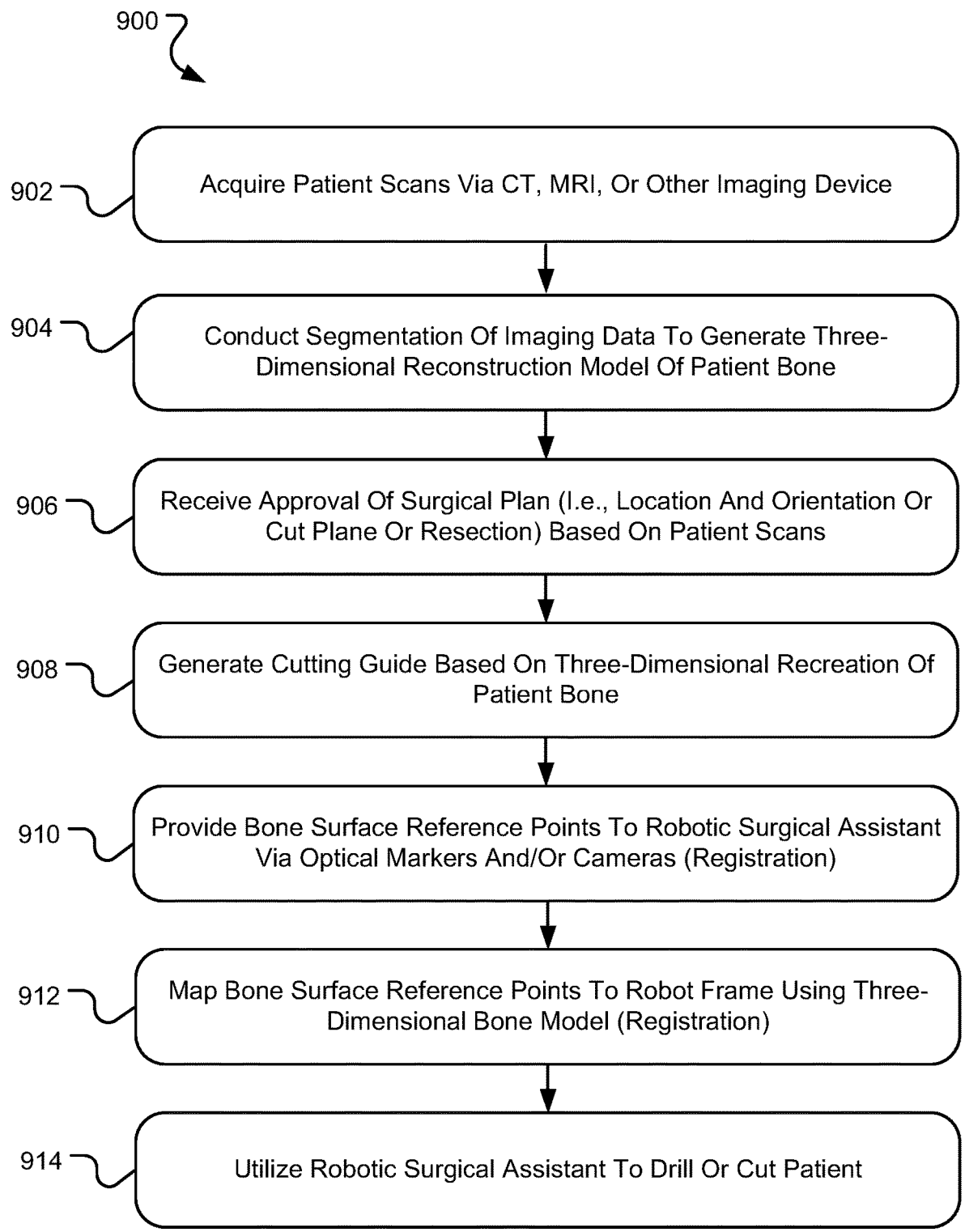
FIG. 9 is a flowchart illustrating a method for performing an arthroplasty surgical procedure in accordance with one embodiment.

As discussed above, the prosthesis may be implanted during an arthroplasty surgical procedure to repair a damaged joint of a patient. FIG. 9 is a flowchart illustrating an example method 900 for performing an arthroplasty surgical procedure in accordance with embodiments described herein. In general, the method 900 provides for a robotic-assisted arthroplasty procedure to repair a damaged joint of a patient. The operations of the method 900 may be performed by many systems or devices, as described below. Additional or fewer operations may be included in the method 900 and may be performed by the systems and devices described or additional systems and devices. Related to the procedure of method 900, FIG. 10 illustrates pre-operative and intra-operative procedures for a robot-assisted arthroplasty surgical procedure associated with the method 900, including some devices and systems for performing the method 900.

Figure 10:
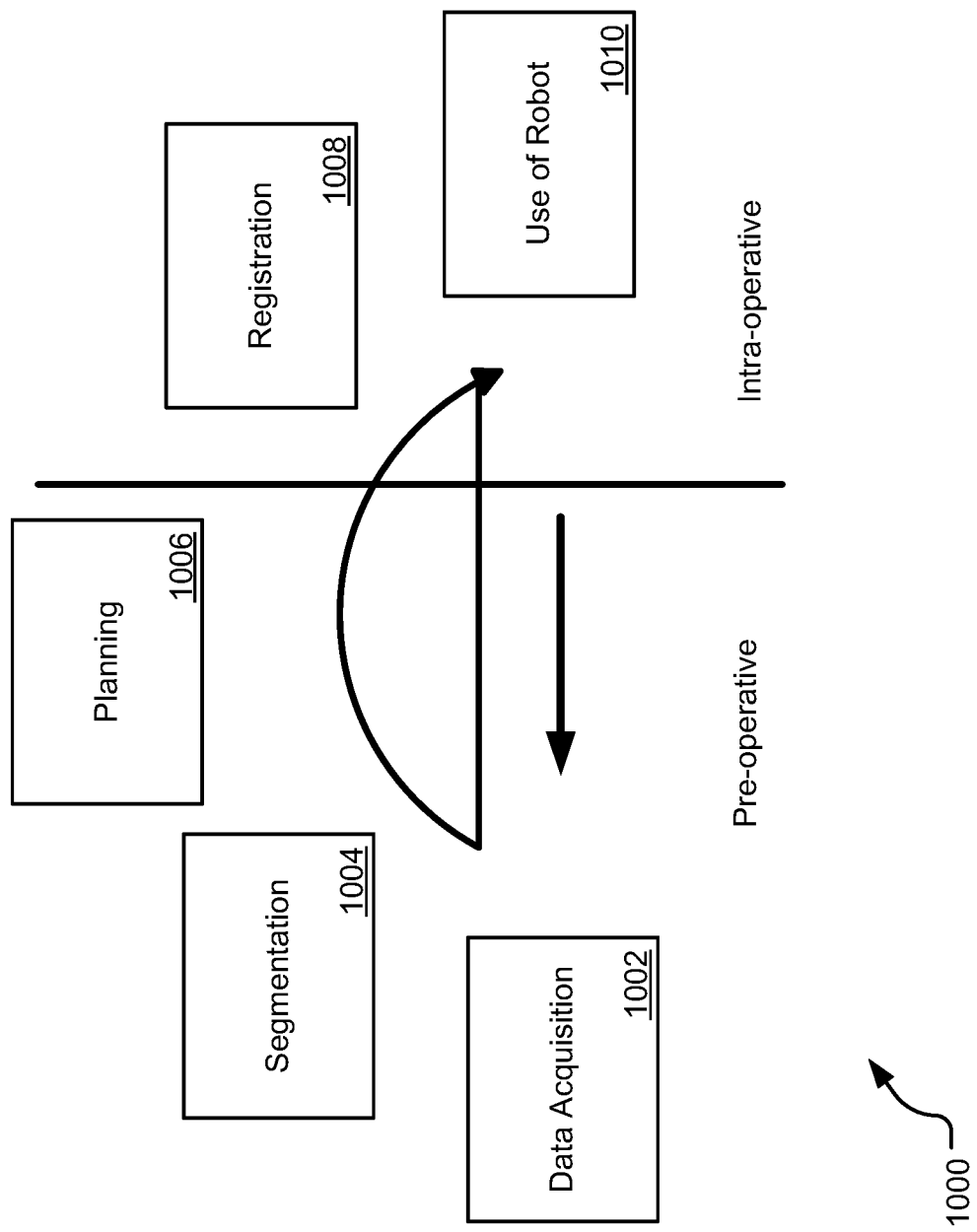
FIG. 10 is a diagram illustrating pre-operative and intra-operative procedures for a robot-assisted arthroplasty surgical procedure in accordance with one embodiment.
Figure 11:
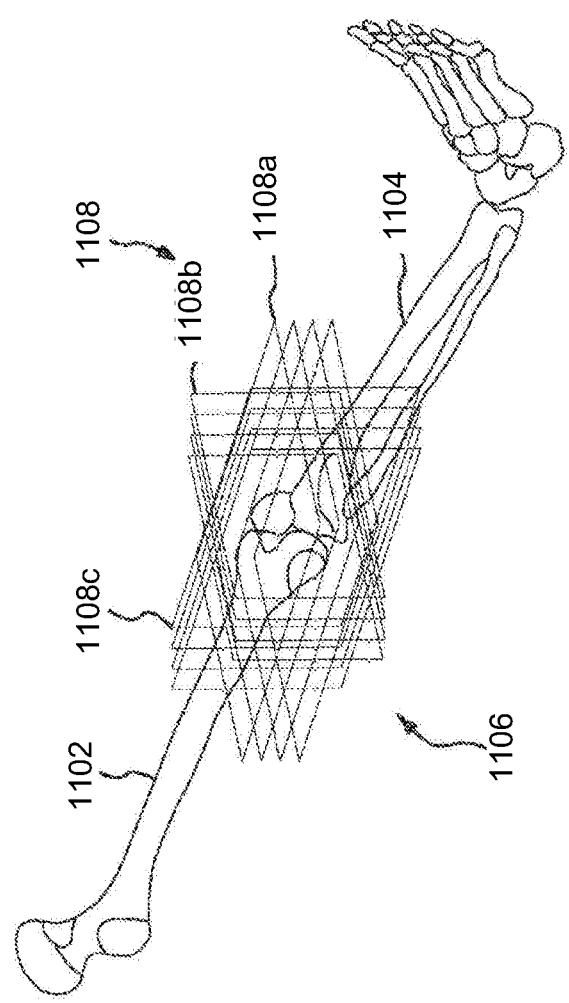
FIG. 11 is a diagram illustrating scan planes for obtaining one or more scans of a patient's anatomy in accordance with one embodiment.

As shown in FIG. 10, a pre-operative portion of the procedure may include a data acquisition phase 1002, a segmentation phase 1004, and a planning phase 1006. An intra-operative portion of the procedure may include a registration phase 1008 and a use of a surgical robotic-device 1010. Each of the various phases of the procedure is discussed in more detail below. In the data acquisition phase 1002, shown in operation 902 of the method 900, one or more scans of a patient may be obtained, and in particular, one or more scans of a damaged joint of the patient may be acquired via an imaging device or system. In one implementation, one or more Computed Tomography (CT) scans, one or more Magnetic Resonance Imaging (MRI) scans, one or more X-Ray scans, or any other type of internal imaging of the patient may be acquired through a corresponding imaging device or system. The imaging of the patient may include two-dimensional or three-dimensional imaging. In one particular example, a series of two-dimensional (2D) images of the patient's joint on which the arthroplasty procedure is to be performed may be obtained or received through a network connection. The 2D images of the patient's joint may be obtained from an imaging device (such as an X-ray or magnetic resonance imaging (MRI) machine) from several aspects of the joint. For example, FIG. 11 illustrates one embodiment for obtaining 2D images of a knee 1106 of a patient. In particular, the patient's knee 1106, including portions of the femur 1102 and tibia 1104, is scanned along with an MRI knee coil to generate a plurality of 2D knee coil MRI images of the patient's knee. In one embodiment, the 2D images 1108 of the knee include a plurality of images taken along a coronal plane 1108a through the knee, a plurality of images taken along an axial plane 1108b through the knee, and/or a plurality of images taken along a sagittal plane 1108c through the knee. In other embodiments, the 2D images may be any combination of coronal, sagittal and/or axial views. In one embodiment, the MRI imaging spacing for the 2D knee coil images may range from approximately 1 mm to approximately 6 mm and may vary from aspect to aspect. For example, the coronal image slices 1108a may be spaced 2 mm apart, while the axial image slices 1108b may be spaced 6 mm apart.

While the embodiments herein are discussed in the context of the imaging being via an MRI machine, in other embodiments the imaging is via computed tomography (CT), X-ray, or other medical imaging methods and systems. Further, although it is discussed herein as a scan of the knee, the 2D images may be obtained for any joint or other area of the patient's body, such as images of the patient's ankle, hip, shoulder, etc.

Once the 2D images of the joint at issue are obtained, the images may be entered into a computing device for processing in a segmentation phase 1004. For example, in operation 904 of the method 900 of FIG. 9, a computing device may receive the acquired patient images or other data through any form of electronic communication with the imaging device. In one particular example, the 2D images may be obtained by the imaging device (such as the MRI imaging machine) and transmitted to a website accessible by the computing device. In general, however, the 2D images may be obtained from the imaging machine in any fashion for further processing by the computing device. Once received, the 2D images may be stored in a computer-readable medium for further processing by the computing device.

The processing of the imaging data may include segmentation of portions of the image to indicate, within the collection of images, the portions of the images that show the patient's bone to generate a three-dimensional model or reconstruction of the patient's bone. For example, a technician may, via a computing device, provide thousands of indicators within each image to outline the outer shape of the bone, such as the patient's femur or tibia within the patient's knee joint. This approach typically uses a dense, three-dimensional grid of points to accurately represent the bone surface, especially a surface having cusps or sharp corners with very small associated radii of curvature. This approach has several disadvantages, however, including the following: (1) this approach is time consuming, often requiring 4-20 hours of intense numerical work to generate and check the accuracy of the grid point coordinates for a single surface; (2) because of the time required to implement this approach for a single surface, use of this approach in mass manufacturing of custom or semi-custom instruments is limited; (3) this approach may introduce geometrical errors, including closing errors; (4) because of the close spacing of grid points, polynomials of high mathematical degree are be used, which can introduce undesirable "ripples" in the mathematical surface produced by a full segmentation process; and (5) formation and analysis of a large number of MRI slices is required. However, as a three-dimensional model of the patient's anatomy is often required for many image-based robot-assisted arthroplasty procedures, segmentation of the patient images is nonetheless conducted.

After segmentation of the patient images and rendering of the three-dimensional model of the patient's anatomy, the arthroplasty procedure 1000 may enter the planning phase 1006. In the planning phase 1006, the surgeon may review the patient scans and/or three-dimensional model of the patient's joint and generate and/or approve of a resection or resurfacing plan for the arthroplasty procedure (in operation 906 of method 900). In some instances, the surgeon may indicate or approve the location and orientation of a resection line on the three-dimensional model of the patient's bone. This information may be stored with the three-dimensional model of the bone as an approved resection line or resurfacing indicator for the patient's arthroplasty procedure.

In some procedures, a conventional cutting guide or cutting jig may be used to aid the surgeon or robotic-assisted device in performing the approved surgical plan. The cutting jigs used in the arthroplasty procedure may attach to the bones of the joint in various ways. Standard cutting jigs (cutting jigs that do not incorporate customization to the particular patient's anatomy) may attach to the bone and often require the surgeon to align the cut line into the proper position during attachment of the cutting jig. As can be appreciated, such general cutting jigs result in vastly different quality of effectiveness, mostly based on the experience and skill of the surgeon. Customized cutting jigs, on the other hand, are designed to mate with the particular patient's bone to reduce the amount of incorrect attachment of the cutting jig to the patient's knee.

The customization of the arthroplasty cutting jigs may vary from procedure to procedure. In one simple example, the customization may include merely selecting one jig from a group of generalized cutting jigs of various sizes in an attempt to match the size of the patient's anatomy based on the three-dimensional model of the patient's joint. On the other end of the spectrum, a customized arthroplasty cutting jig may provide a mating surface that is the exact negative of the joint bone for attachment to the bone surface. Regardless of the customization of the cutting jig used, the jig should be designed to provide the proper location and orientation on the bones of the affected joint such that treatment of the region can be performed accurately, safely, and quickly.

To generate the cutting guide (such as in operation 908 of the method 900), the patient and surgical data or information may be further processed by a computing device. For example, the segmentation information used to form the three-dimensional model may be used to generate a mating surface of the cutting guide that mirrors the surface of the three-dimensional model. In this manner, the cutting jig may be attached to the bone of the joint via the mating surface. The cutting jig may also include a cut guide or line within the jig that guides the surgical saw operated by the surgeon or the robotic device. For example, a surgeon, during the procedure, may insert a saw device into or through the cut line to resect a portion of the bone. In this manner, the ends of the bones of the joint may be resected or resurfaced based on the customized or non-customized guide used in the procedure. The customized cutting guide may be created through a three-dimensional printing process based on the data of the patient model and the approved surgical plan. Particular uses of a customized guide for robotic-assisted surgical procedures are discussed in greater detail below for registering a patient anatomy with a robotic surgical device, attaching a robotic surgical device to a patient's anatomy, locating a patient within an operating environment, and more.

Figure 12:
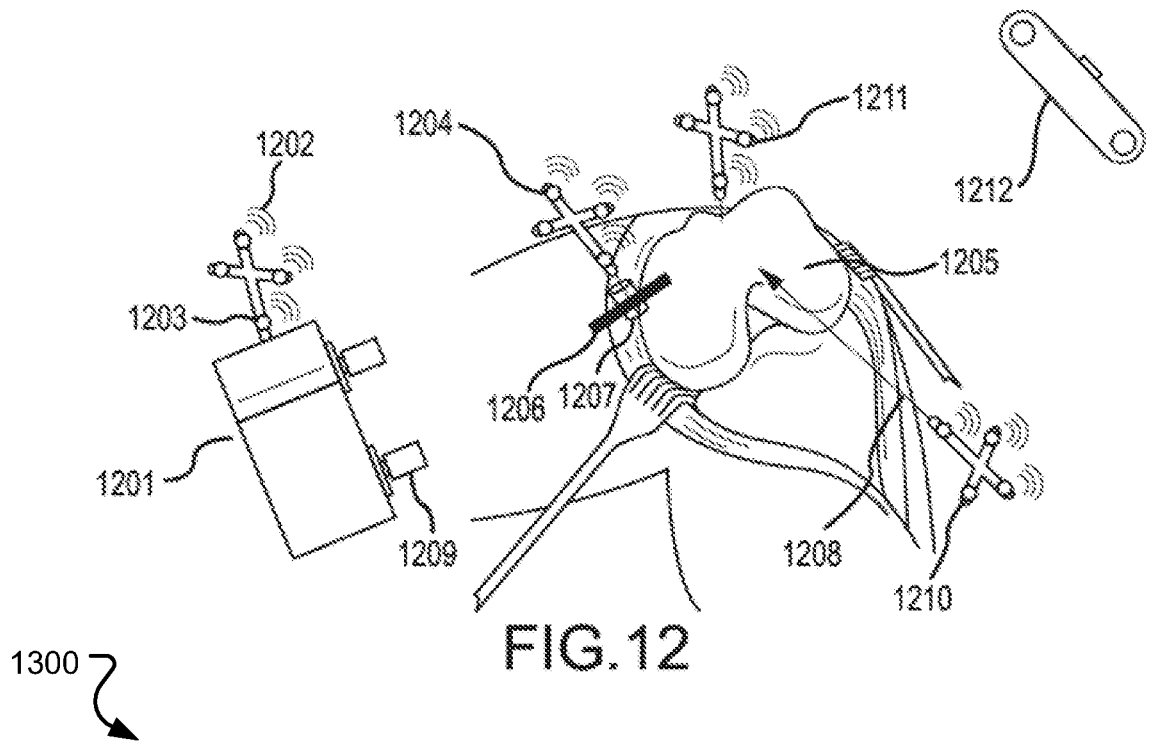
FIG. 12 is an illustration showing robotic registration of the femur and tibia using computer navigation based on a target implant position and size in accordance with one embodiment.

The approval of the surgical plan and, in some instances, the generation of the cutting guide, may end the pre-operative process 1000. To begin the intra-operative portion of the surgical procedure, the patient is prepared for the surgery and the arthroplasty procedure may begin. Upon resection of the tissue surrounding the joint, the surgeon, in operation 910, may provide several reference points on the surface of the patient's bone to the robotic surgical assistance device. The registration of the patient's anatomy to the robotic device may be performed in many ways but generally include locating the patient's anatomy in three-dimensional space so that the robotic device may map the patient's location/orientation in relation to the robotic device location/orientation. In one example as shown in FIG. 12 and using a computer navigation system, the robotic device may include retroreflective markers 1210 and tool tip 1208 with a known offset and tool-tip diameter to register bony landmark of interest. The stereoscopic sensor 1212 may use infrared (IR) 1202 to detect reflective makers 1210 with unique configuration and apply offset to calculate the position and orientation. For example, through triangulation of the reflective markers 1210 as seen by the IR sensors 1212, the location in space of the markers may be determined. The dimensions of the probe device 1210 may also be known by the computer navigation system such that a relationship between the tool tip and the markers of the probe device 1210 may be calculated by the robotic device or a computer navigation system associated with the robotic device. In some implementations, markers 1204 and 1211 may be attached to the patient anatomy for tracking of the patient movement during the procedure. The computer navigation system may be utilized to attach a bone-mounted surgical robot 1201 to the patient's anatomy, as described in more detail below.

In some instances, the robotic device may provide one or more instructions to the surgeon on locations on the patient's bone to place the probe such that the robotic device may calculate the location of the requested point in three-dimensional space. For example, the center of the knee, the lowest points of the medial and lateral condyles, the medial and lateral side of the femur and anterior cortex of the lateral ridge. In addition by attaching marker 1211 to the femur and rotating the knee in a circular and linear motion, the center of the hip can be estimated using a spherical profile with a certain center and radius. In other instances, the surgeon may locate the probe device 1208 at various points along the patient's bone and provide an indication to the robotic device as to a correlation point on the patient's anatomy. The requested or provided locations may correspond to the three-dimensional model of the patient's joint such that the robotic device may map the registration information to the model in operation 912 of the method 900 of FIG. 9. Once the patient location/orientation is mapped to the three-dimensional patient model, a robotic-surgical device may perform the approved resection of the patient's bone based on the approved surgical plan in operation 914, as shown in phase 1010 of FIG. 10. The robotic device may operate independently based on the surgical plan or may be guided by the surgeon to resect or resurface the bone. Upon completion, the results of the procedure may be analyzed for future use by the surgeon or other entity and the process may repeat for other patients.

Despite the accuracy of using a surgery-assisting robotic device, the above-described procedure may have several drawbacks. In addition to the long period of pre-operative time and the costs involved with robotic-assisted devices, the registration process to map the patient bone to the three-dimensional model may be time-consuming and error prone. For example, many registration processes require the surgeon to provide upwards of 50 or so verification points on the patient's bone for a proper mapping. Further, some registration points may require the surgeon to pierce through cartilage or other soft tissues of the joint to locate some reference points. Also, the accuracy of the registration process depends on the accuracy of the three-dimensional model of the patient's joint. If the model is inaccurate due to segmentation or computational error, the registration process may be similarly inaccurate, resulting in a compounded error in the resection of the bone.

Figure 13:
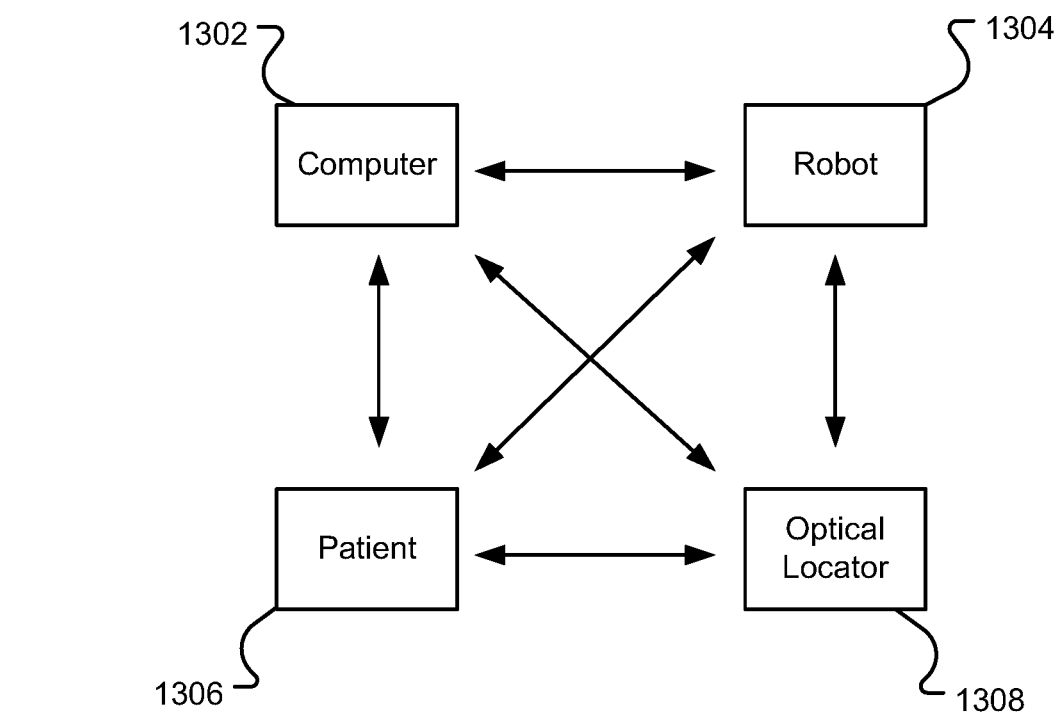
FIG. 13 is a system diagram illustrating the exchange of mapping information between components of a robot-assisted arthroplasty surgical system in accordance with one embodiment.

In addition, the mapping information must be shared between several components of the system including the patient, robotic device and/or computer-navigation system to ensure proper location of the resection during the arthroplasty procedure. For example, FIG. 13 is a system diagram 1300 illustrating the exchange of mapping information between components of a robot-assisted arthroplasty surgical system in accordance with one embodiment. As discussed above, the arthroplasty procedure may include a surgical-assistance robotic device 1304 for executing one or more cuts, resections, resurfaces, and the like on the patient 1306. To determine the location and orientation of the resection, the robotic device 1304 may determine the location and orientation of the patient's anatomy in three-dimensional space by mapping registration inputs to a model of the patient's anatomy. In particular, a three-dimensional model of the patient's joint may be uploaded to a computing device 1302 associated with or in communication with the robotic device 1304. The three-dimensional model may be generated from the imaging and segmentation process discussed above. With the patient model, the robotic device 1304 may be aware of the surgical plan and the location of the resection or resurfacing on the patient's bone. However, the robotic device 1304 may not be aware of the location and/or orientation of the patient 1306.

Locating the placement of the patient 1306 in relation to the robotic device 1304 may be accomplished through the registration process. In particular, an optical locator 1308 may be utilized by the robotic device 1304 and/or the computing device 1302 to locate the patient's 1306 location and orientation via the registration process. A surgeon may be instructed to use a probe tool, a manual coordinate measurement machine (CMM) arm, or other registration tool to locate various points along the exposed bone of the patient's joint 1306. The optical locator 1306 may track or otherwise mark in space the location of markers on the registration tool as the tool is placed onto the patient's 1306 anatomy by the surgeon. Each registered location in three-dimensional space in relation to the optical locator 1306 may be correlated to the same location on the model of the patient's bone, either by the computing device 1302 or the robotic device 1304. By mapping the registration points of the patient's bone to the three-dimensional model, the computing device 1302 and/or the robotic device 1304 may determine the approximate location of the patient's anatomy in relation to the surgical plan generated from imaging scan. Through the modeling and registration process, the robotic device 1304 may calculate or otherwise determine the location and orientation of the resection or resurfacing of the approved surgical plan. Once determined, the robotic device 1304 may aid the surgeon in performing the resection or resurfacing as part of the arthroplasty procedure. Inaccuracies in any of the shared mapping information (segmentation of the patient images, modeling based on the segmentation, registration of the patient's anatomy, mapping of registration points to the model, patient motion, etc.) may result in inaccurate resection and/or resurfacing of the patient's bone and a failed or undesirable result of the arthroplasty procedure.

An additional component of a robot-assisted arthroplasty procedure includes tracking of any patient movement during the procedure. As discussed, the registration process provides the robotic device 1304 with an estimated location mapping of the patient location and orientation in space. However, in some instances, the patient's anatomy may move or be moved during the procedure. To track the movement of the patient, one or more optical markers may be mounted on or near the patient's joint that is the focus of the arthroplasty procedure. The optical locator 1308 discussed above may track the movements of the optical markers during the procedure and provide indicators of the detected movements to the computing device 1302 or the robotic device 1304. Adjustments to the mapping of the patient's location to the three-dimensional model may be made by the computing device 1302 and/or the robotic device 1304 to compensate for the movement of the patient. However, tracking of the patient's movement in this manner may introduce still more inaccuracies into the arthroplasty procedure. For example, optical locators 406 require line of sight with the optical markers to determine when those markers move. In many instances, however, the surgeon, surgical equipment, or other objects may interrupt that line of sight between the optical locator 406 and the optical markers such that some movements of the patient may be missed. Further, movement along the line of sight may also be difficult for the optical locator 1306 to detect. Other inaccuracies, such as resolution of the cameras used and/or foreign objects on the lens of the cameras may negatively affect the accuracy of detecting the movement of the patient. Again, these inaccuracies may further result in inaccurate resection and/or resurfacing of the patient's bone and a failed or undesirable result of the arthroplasty procedure.

Figure 14:
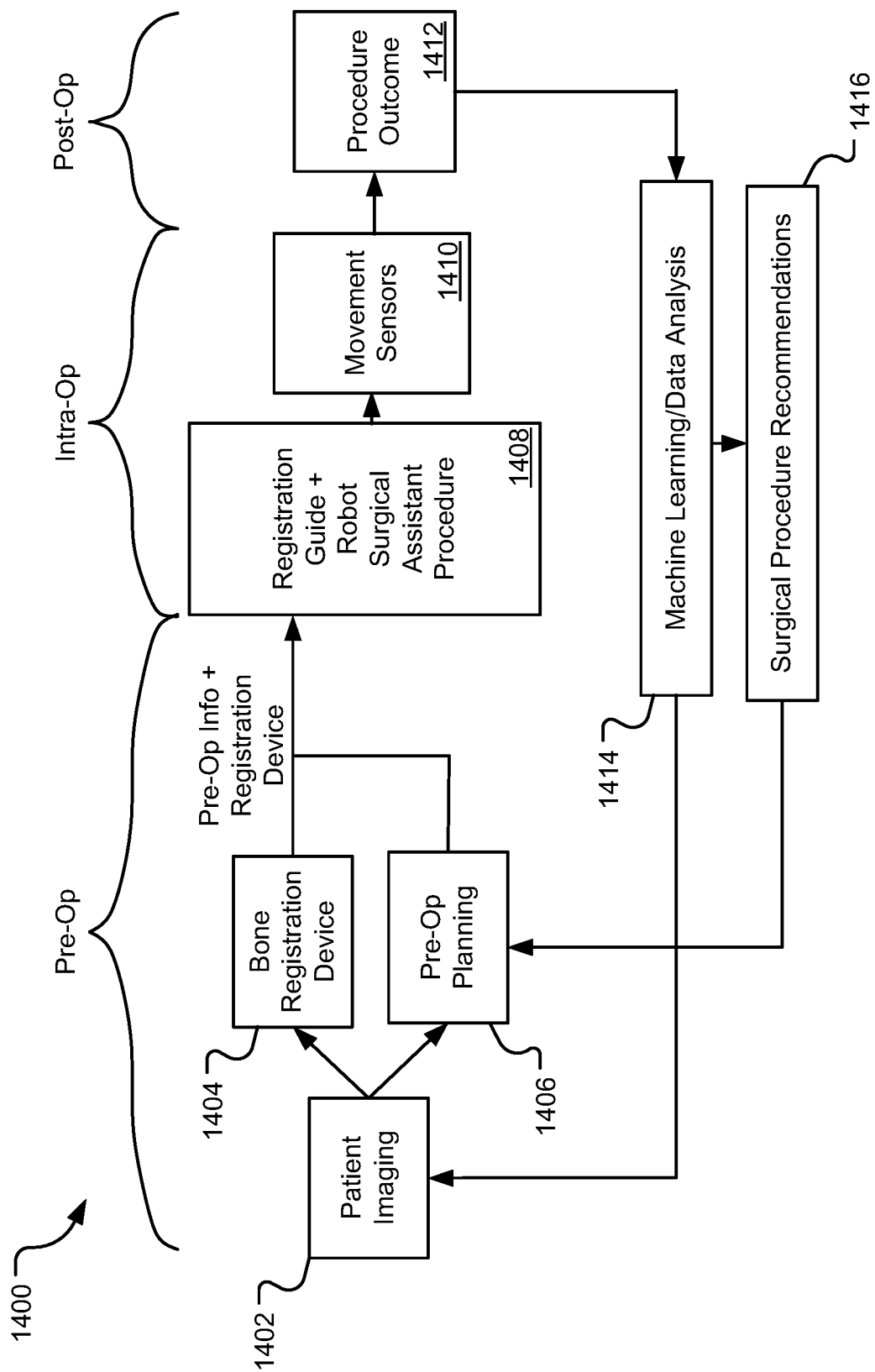
FIG. 14 is a system diagram illustrating pre-operative, intra-operative, and post-operative procedures for a robot-assisted arthroplasty surgical procedure in accordance with another embodiment.
Figure 15:
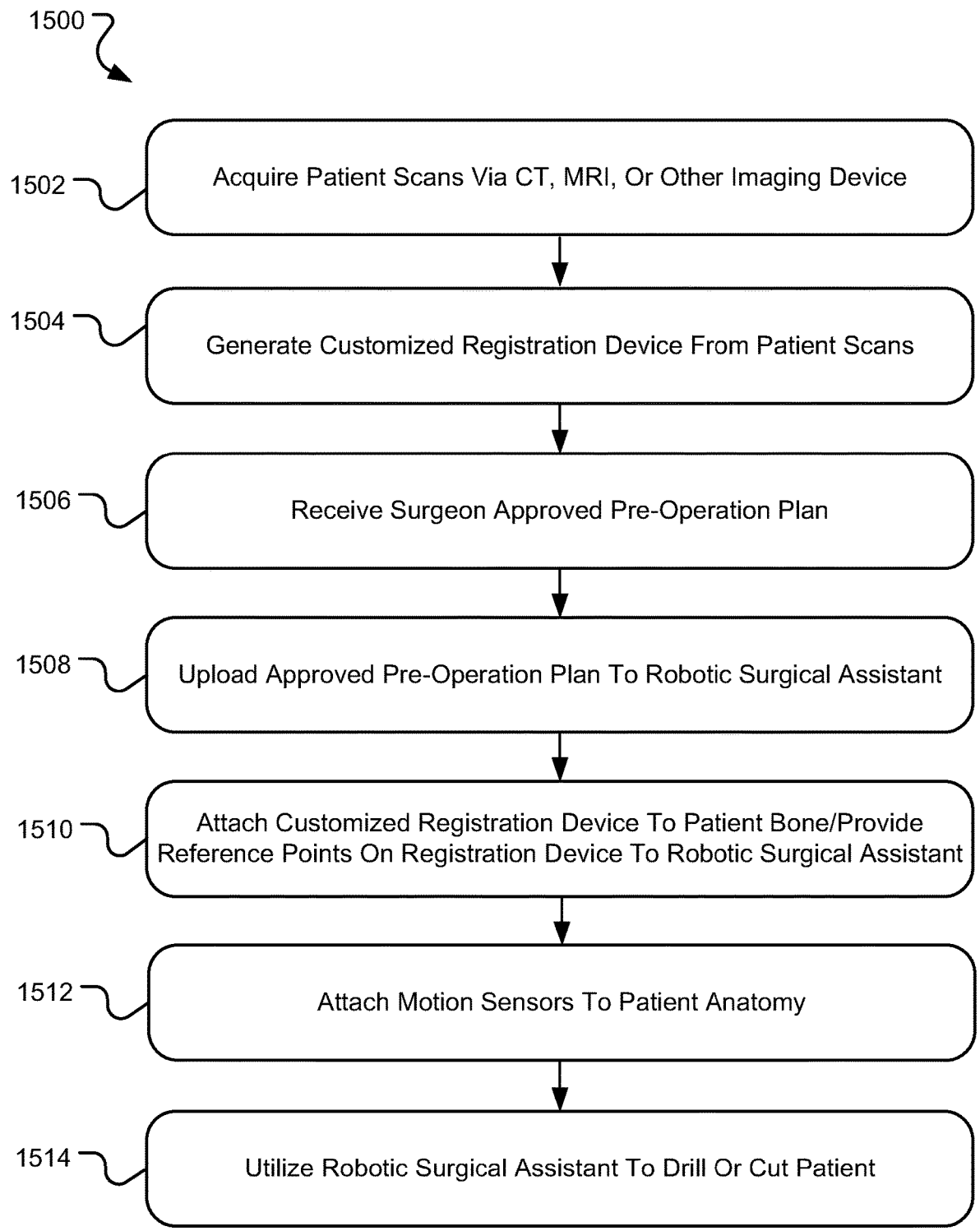
FIG. 15 is a flowchart illustrating a method for performing an arthroplasty surgical procedure using one or more arthroplasty registration customized guides in accordance with another embodiment.

To address these and other undesirable results of the robot-assisted arthroplasty procedures, a system 1400 for pre-operative, intra-operative, and post-operative procedures for a robot-assisted arthroplasty surgical procedure in accordance with another embodiment is provided in FIG. 14. The system 1400 of FIG. 14 illustrates various components and operations to perform an arthroplasty procedure that addresses several of the drawbacks of other robotic-assisted arthroplasty procedures. Several of the operations of the system 1400 are illustrated in the flowchart of FIG. 15. In particular, FIG. 15 is a flowchart illustrating a method 1500 for performing an arthroplasty surgical procedure using the system 1400 of FIG. 14 in accordance with another embodiment. The operations of the method 1500 may be performed by components of the system 1400 or other components not illustrated in FIG. 14 to perform the arthroplasty procedure. In one instance, the method 1500 may include one or more customized registration guides to register the patient's location to the robotic device, as described in more detail below.

Similar to above, the system 1400 of FIG. 14 may include a patient imaging device to obtain a plurality or series of images of a patient's anatomy, such as a damaged joint. The images may be obtained, in operation 1502, via an imaging device or system, such as a CT scanner, MRI scanner, X-Ray scanner, or any other type of imaging device, as described above. Also similar to above, the imaging data or scans may be utilized by a surgeon to generate or approve a surgical plan for the arthroplasty procedure. The pre-operative planning may include a surgeon reviewing the patient scans and selecting one or more steps of the arthroplasty procedure based on the scans, such as cut planes location on the patient's joint to remove the damaged portion of the patient's bone for implanting a joint replacement device, a resurfacing plan of the damaged portion of the patient's bone, an implant location and orientation within the joint, and the like. The pre-operative planning 1406 conducted by the surgeon may include, in some instances, transmitting the scanned images or other patient data over a network to a computing device on which the surgeon may view the images. The surgeon may also provide indications or other information of the planned procedure via the computing system on which the images are viewed.

Simultaneously to the surgeon's pre-operative planning 1406, a bone registration device 1404 may be generated based on the patient scans in operation 1504. Similar to the customized cutting guides described above, the bone registration device 1404 may be based on a segmentation process performed on the patient scans or may include generating a three-dimensional model of the patient's joint. In other instances, however, the customized bone registration device 1404 may be generated from a collection of two-dimensional images or scans of the patient. In particular, systems, methods, computer program products, manufacture process and the like, may be provided for as customized arthroplasty registration device 1404. In particular, a method of creating a customized arthroplasty registration device 1404 from one or more two-dimensional (2D) images of the patient's joint to undergo the arthroplasty procedure. The method includes receiving the 2D images of the joint from an imaging device, reformatting the images, and creating a customized registration device 1404 template from the images. In general, one or more landmarks may be electronically marked on one or more of the series of 2D images of the patient's joint through a computing device. These electronic markers on the series of 2D images correspond to landmarks of the patient's joint undergoing the arthroplasty procedure. Once the template for the registration device 1404 is created by the computing device utilizing one or more of the electronic markers on the 2D images, a tool path or milling program is generated by the computing device. The tool path or milling program may then be provided to a milling or 3D printing machine to create the registration guide corresponding to the machine-specific program. The registration device 1404 is thus customized to the landmarks identified in the series of 2D images of the patient's joint. Further, the procedure does not require the generation of a three-dimensional (3D) model of the patient's anatomy to create the customized nature of the registration device 1404. Rather, by utilizing one or more mating shapes that contact the joint anatomy at particular contact points of the joint anatomy corresponding to the identified landmarks in the 2D images, the customization of the registration device 1404 is achieved. Further, because the process does not require the generation of a 3D model, the customized registration guides may be produced more quickly and efficiently than previous customization methods.

One particular approach for creating a customized arthroplasty registration guide from two-dimensional imaging is described in U.S. Pat. No. 10,139,807, the entirety of which is incorporated by reference herein. The approach described in the incorporated document eliminates the full segmentation process described above and the associated three-dimensional anatomical modeling of a bone surface and replaces that approach with data obtained from relatively few MRI "slices," as few as, for example, six two-dimensional slices, that permits flexibility in choice of contact points between the bone surface and the instrument (guide) that mates with the bone surface. By replacing the full segmentation procedure, with its thousands of grid points, with a simpler, quicker procedure that works with as few as about twelve contact points between an anatomical surface, such as the posterior femur, a customized registration device 1404 may be generated at a faster rate.

Figure 16:
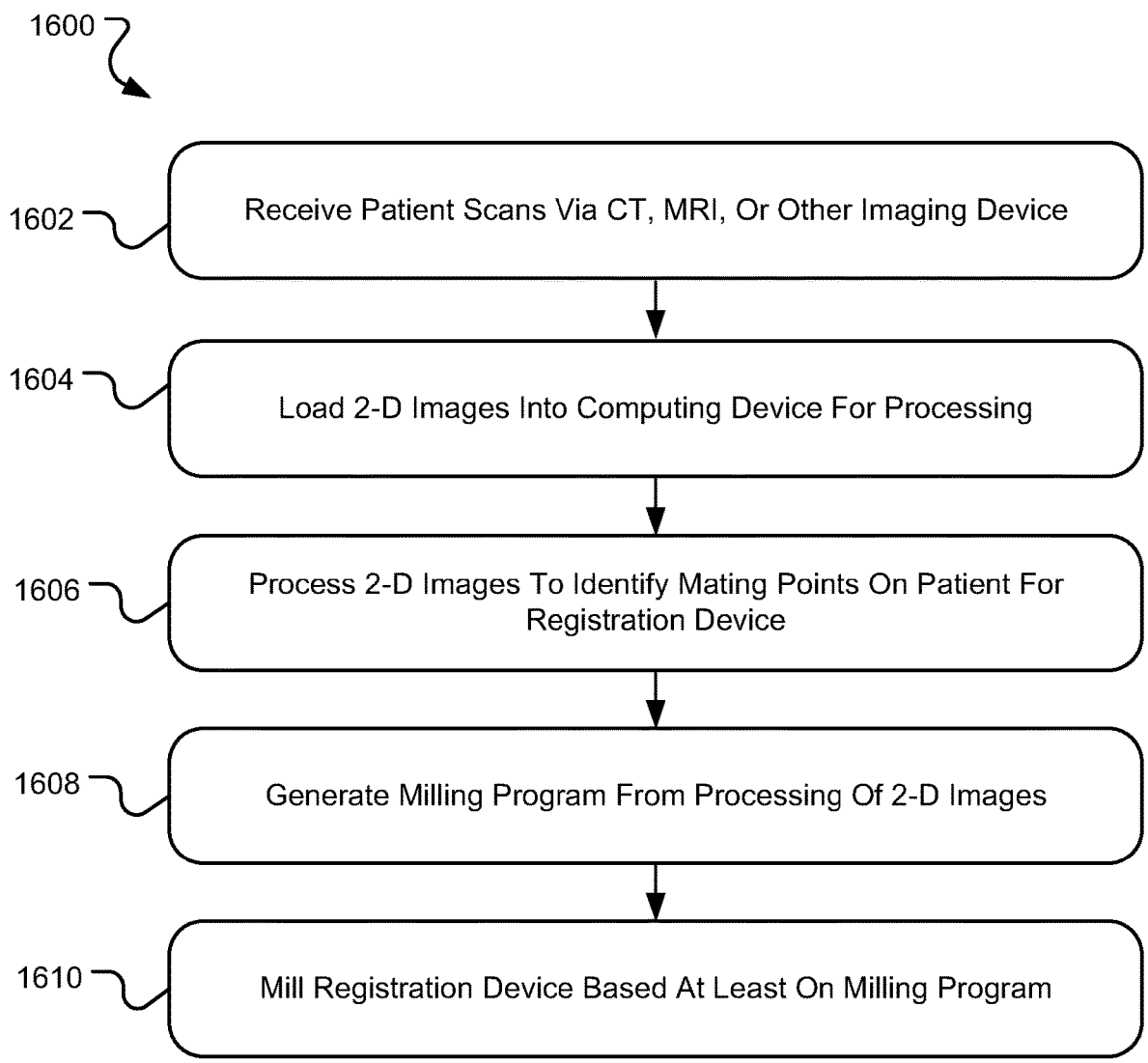
FIG. 16 is a flowchart illustrating a method for creating a customized arthroplasty registration guide from one or more two-dimensional images of a patient's joint in accordance with another embodiment.

One method for creating a customized registration guide for an arthroplasty procedure (such as a total knee arthroplasty) is illustrated in the method 1600 of the flow chart of FIG. 16. In particular, the method described in FIG. 16 provides for creating a registration guide that is customized to the patient's anatomy from 2D images of the patient's joint. Although more or fewer operations may be included in the process to generate a customized arthroplasty registration guide, the operations of FIG. 16 provide a general outline of one such process that utilizes 2D images of the patient's joint.

Beginning in operation 1602, the images or scans of the patient's anatomy may be received via a network. In some instances, the images may include a series of two-dimensional (2D) images of the patient's joint on which the arthroplasty procedure is to be performed. As described, the 2D images of the patient's joint may be obtained from an imaging device (such as an X-ray, computed-tomography (CT), or magnetic resonance imaging (MRI) machine) from several aspects of the joint, such as that shown in FIG. 3. Although shown as a scan of the knee, the 2D images may be obtained for any joint or other area of the patient's body, such as images of the patient's ankle, hip, shoulder, spine, etc. Once the 2D images of the joint at issue are obtained, the images may be entered into a computing device for processing and to further the procedure through which the arthroplasty registration guide is created in operation 1604. The computing device may receive the images through any form of electronic communication with the imaging device. In one particular example, the 2D images may be obtained by the imaging device (such as the MRI imaging machine) and transmitted to a website accessible by the computing device. In general, however, the 2D images may be obtained from the imaging machine in any fashion for further processing by the computing device. Once received, the 2D images may be stored in a computer-readable medium or cloud-based storage for further processing by the computing device.

In operation 1606, the 2D images of the joint are processed to reformat the images to convert the images from a machine-defined coordinate system to approximate a true anatomical coordinate system for the images and/or to identify one or more points or landmarks associated with the patient's joint that mate with contact points or surfaces of the customized registration guide. In general, a true anatomical coordinate of the patient's joint corresponds to the natural alignment of the patient prior to damage to the joint. For example, true anatomical alignment of the patient's knee may correspond to an axial plane through the center of the knee parallel to the ground while the patient is walking. It should be appreciated, however, that reformatting the 2D images to achieve an image that is a true anatomical alignment of the knee is not required. Rather, the reformatting of the images may approximate images of true anatomical alignment of the knee. The images that illustrate the joint at a true anatomical coordinate system may be used for guide creation and to aid a surgeon in approving the guide placement in the damaged joint.

In one embodiment, an operator of the computing device may utilize a monitor or other interface of the computing device through which the images are viewed. Utilizing a software program executed by the computing device, the operator may view the 2D images and provide one or more electronic markers on at least one of the 2D images. These electronic markers may correspond to one or more reference points within the images for processing and reformatting of the images by the computing device and/or identify features or landmarks within the 2D images of the patient's anatomy that correspond to contact surfaces of the customized registration guide.

In another embodiment, a program executed by the computing device may obtain the 2D images, determine the one or more reference points within the images, reformat the images to correspond to a true anatomical coordinate system, and/or identify the landmarks within the 2D images that correspond to contact surfaces of the customized registration guide, with or without the aid of an operator of the computing device. In yet another embodiment, one or more of these operations are performed by the operator, while other operations are performed by the computer program. As such, any of the operations and methods described herein may be performed by an operator of the computing device or the computing device itself through hardware, software, or a combination of both hardware and software. The particular operations and considerations of operation 1606 are discussed in more detail in the incorporated U.S. Pat. No. 10,139,807.

With the various electronic markers identified on the 2D image(s), the computing device may generate a program or computational information based on the electronic markers in operation 1608. This computational information may be provided to a milling device, such as a computer numerical control (CNC) milling device in operation 1610, to create the customized registration guide for the arthroplasty procedure based at least on the computational information provided to the milling device. In general, a CNC machine or robotic device is operated by programmed commands included in a program or list of commands to remove or add material to create an apparatus based on the instructions provided in the commands. Thus, in this example, CNC milling machines translate the commands into control signals of a cutting device (tool) to mill a customized guide out of a guide blank according to the provided information. As pertaining to the method of FIG. 16, the computational information generated by the computing device associated with the electronic markers in the 2D images are utilized to generate the series of commands to operate the CNC milling machine. Thus, a customized arthroplasty registration guide is created by providing the milling or cutting program that includes information concerning the electronic markers in the 2D images and guide blank to the CNC machine so that the machine mills or otherwise creates the customized guide based on the instructions of the milling program. In this manner, 2D images of a joint may be utilized to create a customized arthroplasty registration guide for use in arthroplasty procedures to restore function and use to the joint of a patient.

Through the process above, a customized registration guide may be developed and generated specific to the patient of the arthroplasty procedure. In particular, a portion of the registration guide may be customized to securely mate with the patient's bone at several points. The points along the patient's bone to which the registration guide mates may be particular points identified as providing a secure and stable mating with the patient's bone without requiring an exact mirror of the patient's bone surface for mating. In other words, through the identification of particular locations or portions of the patient's bone within the 2D images, a customized registration guide may be generated that mates with the patient's anatomy without the generation of a three-dimensional model of the patient's bone. This may significantly reduce the amount of time needed to generate a customized registration guide for the patient for use in the arthroplasty procedure. In addition, the generation of the registration guide may occur at the same time as the pre-operative planning 1406 performed by the surgeon as the registration guide may not include a cutting jig or other portion of the resection or resurfacing of the joint. Rather, the registration guide may be developed from the patient scans contemporaneously with the pre-operative planning 1406.

Figure 17B:
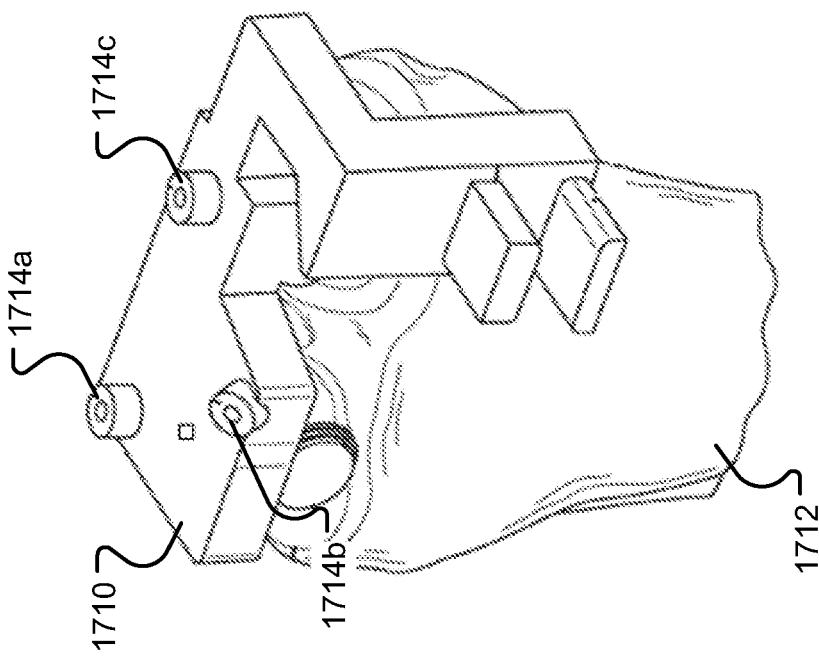
FIGS. 17A-17E are diagrams of exemplary customized registration guides for use in robotic-assisted arthroplasty procedures in accordance with some embodiments.
Figure 17A:
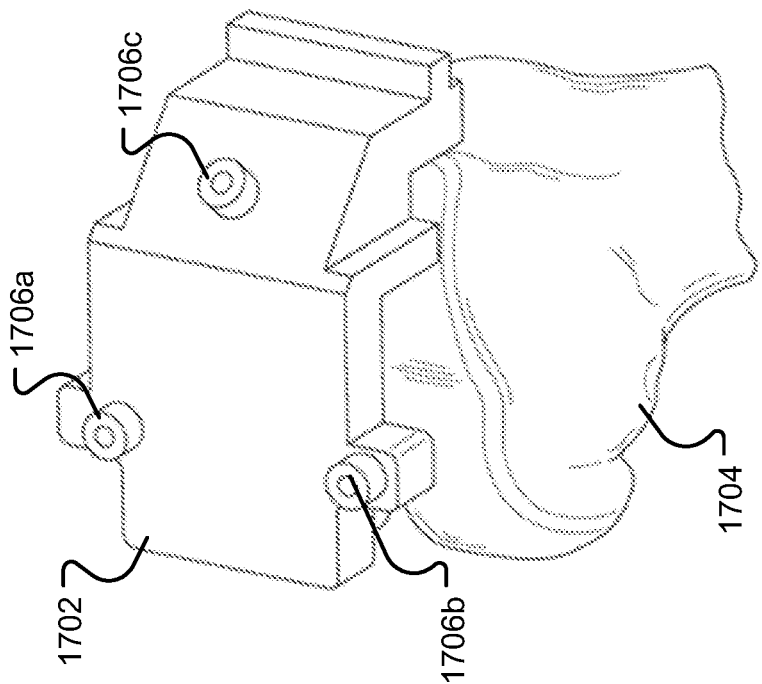

FIGS. 17A-17E are diagrams of exemplary customized registration guides for use in robotic-assisted arthroplasty procedures in accordance with some embodiments. In particular, FIG. 17A illustrates an example customized registration femoral guide 1702 for use in a total or partial knee arthroplasty procedure. The customized registration femoral guide 1702 may be generated from 2D images of a patient's knee, as described above. In general, the femoral registration guide 1702 may mount upon or otherwise mate with the patient's femur 1704 via a plurality of mating surfaces specifically selected and generated based on the images of the patient's knee to provide a stable support base for the registration guide. The selection of mounting locations on the femur 1704 and the generation of the customized femoral registration guide 1702 is described in more detail in U.S. patent application Ser. No. 14/820,451, the entirety of which is incorporated by reference herein. As further explained in more detail, the customized femoral registration guide 1702 may include one or more portions 1706a-1706c for mounting reflective markers by drilling pins into the bone for tracking movement and location of the femoral registration guide 1702. Although three such reflective marker mounting portions 1706a-1706c are shown in the femoral registration guide 1702, the reference guide may include more such mounting portions. Further, the reflective marker mounting portions 1706a-1706c may be located at various locations on the femoral registration guide 1702.

FIG. 17B illustrates an example customized registration tibia guide 1710 for use in a total or partial knee arthroplasty procedure. The customized registration tibia guide 1710 may be generated from 2D images of a patient's knee, as described above. In general, the tibia registration guide 1710 may mount upon or otherwise mate with the patient's femur tibia 1712 via a plurality of mating surfaces specifically selected and generated based on the images of the patient's knee to provide a stable support base for the registration guide. The selection of mounting locations on the tibia 1712 and the generation of the customized tibia registration guide 1710 is described in more detail in U.S. Pat. No. 9,883,871, the entirety of which is incorporated by reference herein.

Further, similar to the femoral registration guide 1702 discussed above, the customized tibia registration guide 1710 may include one or more portions 1714a-1714c for mounting reflective markers for tracking movement by drilling pins into the bone and location of the tibia registration guide 1710. Although three such reflective marker mounting portions 1714a-1714c are shown in the tibia registration guide 1710, the reference guide may include more such mounting portions and may be located at various locations on the tibia registration guide 1714.

Figure 17C:
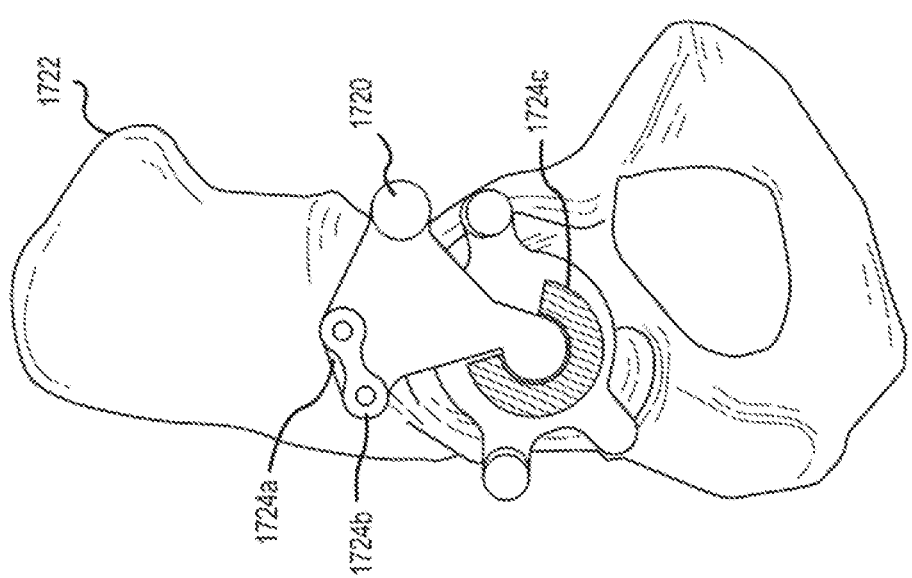
Figure 17D:
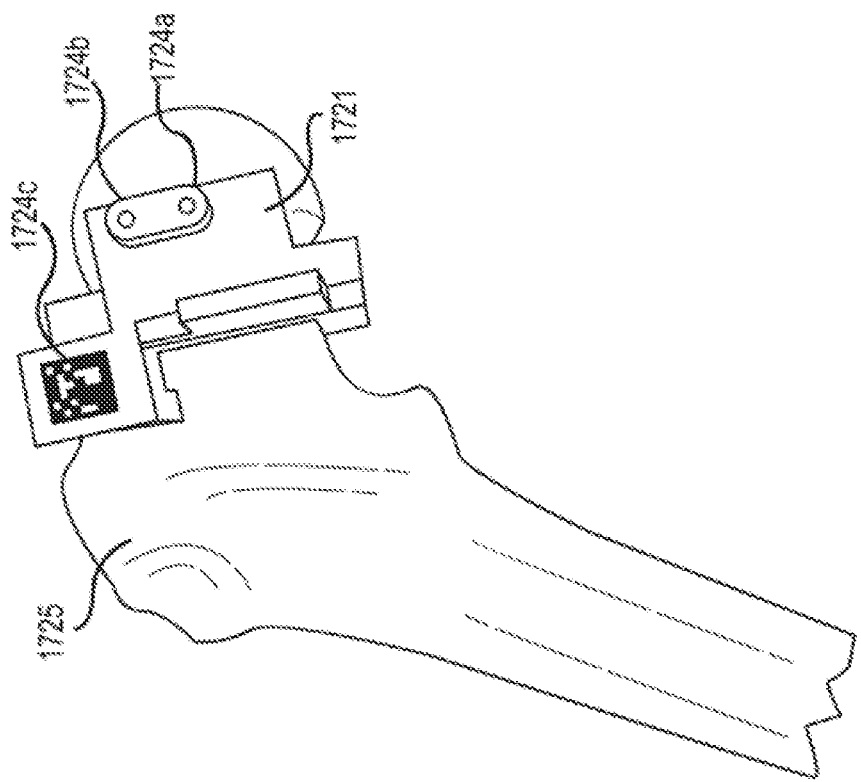
Figure 17E:
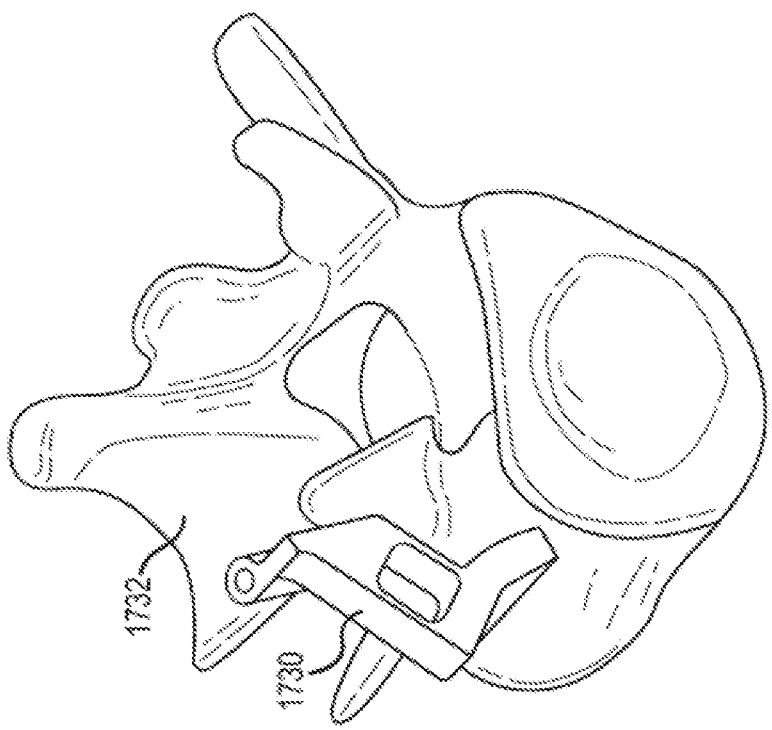

In a similar manner as the femoral registration guide 1702 and the tibia registration guide 1710, other customized registration guides may be generated for other joints and/or patients based on the 2D scans of the patient. For example, FIG. 17C illustrates an example customized registration acetabular guide 1720 for use in a total or partial hip arthroplasty procedure. A corresponding customized registration guide for the femur portion 1725 of the hip joint 1722 may also be generated for the total or partial hip arthroplasty procedure illustrated in FIG. 17D. Also similar to the above customized registration guides, the registration hip guides 1720 and 1721 may include a plurality of portions 1724a-1724b for mounting reflective markers for tracking movement and location of the hip registration guided 1720 and 1721. FIG. 17E illustrates an example customized registration spine guide 1730 for use in a spinal arthroplasty procedure. The spinal customized registration guide 1730 may similarly be generated from image slices taken of the patient's spine 1732 and may mount onto the vertebrae of the patient's spine at a plurality of pre-selected locations that provide a stable mating condition for the registration guide. Also similar to the above customized registration guides, the spinal registration guide 1730 may include a plurality of portions for mounting reflective markers for tracking movement and location of the registration guide 1730.

Returning to the system 1400 of FIG. 14 and the method 1500 of FIG. 15, the surgeon-approved surgical plan 1406 and one or more customized bone registration devices 1404 may be provided, in operation 1506, to begin the intra-operation phase of the procedure. More particularly, the customized bone registration devices may be shipped to the health-care facility in which the procedure is to occur and the operation plan 1406 may be uploaded, via a network connection, to a computing device or the robotic surgical assistant. In some instances, aspects of the milling program generated for creation of the bone registration device 1404 may be provided to the computing device or robotic device. In general, dimensions, orientations, sizes, outlines, structures, shapes, etc. of the bone registration devices for the arthroplasty procedure may be provided to the computing device or robotic device for use in locating the patient's anatomy for performing the arthroplasty procedure. The operative plan may also be uploaded to the robotic surgical assistant device in operation 1508, in some instances. In general, the robot surgical assistant device may be a free-standing robotic device (disconnected from the surgical patient) or an attaching robot device (one that attaches to the patient anatomy in some manner). Regardless of the robot surgical assistant device used, the robotic device may receive the operation plan to perform some aspect of the procedure, such as a resection or resurfacing of the bone, based on the uploaded or received operation plan.

Described first are benefits and advantages gained through the use of patient-customized guides for free-standing or unattached robotic surgical assistant devices. Advantages and benefits gained through the use of attaching robot surgical assistant devices are discussed in detail below beginning with FIG. 20. Regardless of the robotic surgical device utilized, the use of 2D images to generate a bone registration device 1404 may improve the speed and accuracy of both the pre-operative stage and the intra-operative stage of the arthroplasty procedure.

For a free-standing robotic surgical assistant device, the robotic device may determine the location and orientation of the portion of the patient to which the procedure is to be conducted and, from the patient location/orientation information and the surgical plan information, determine the location and orientation of the resection plane or resurfacing shape of the arthroplasty procedure in relation to the patient's anatomy. In other words, the robotic assistance device may perform the resection or resurfacing of the patient's bone once the robotic device has identified, from the surgical plan and the patient location, where such a resection or resurfacing is to occur in three-dimensional space. To locate the patient's location/orientation in relation to the robotic device location/orientation, the computing device or robotic assistant device may map an orientation and location of the robotic device itself with the registration guide located on the patient's bone in operation 1510. In one instance, the robotic device may include an optical locator similar to that described above. As shown in FIG. 12, the optical locator 1210 may include a stereoscopic sensor 1212 that locates one or more optical markers located on or mounted on the registration guide attached to the patient's bone. In this example, the surgeon may attach the registration guide onto the patient's bone during the arthroplasty procedure. In contrast to the above-described system in which optical markers 1204, 1211 may be attached to the patient's anatomy, one or more optical markers may be mounted on or included on the registration guide mounted on the patient's bone, such as in position 1706a-c of the femoral registration guide 1702 of FIG. 17A. This approach would remove the need to attach such markers to the patient's bone or other portions of the anatomy. Other types of registration guides may include similar mounting portions for the mounting of the optical markers.

The stereoscopic sensor, in this example, may locate the optical markers on the registration guide and calculate, from the location and orientation of the optical markers of the registration guide, a location and orientation of the patient's bone. In particular and using the system 1300 of FIG. 13 as an example, the optical locator 1308 may provide the measured distances, from the optical locator to each of the optical sensors attached to the patient, to the computing device 1302 or robotic device 1304. The computing device 1302 or robotic device 1304 may then map, from the received distances, the location of the optical markers in three-dimensional space in relation to the location and orientation of the robotic device. More particularly, with the location of the robotic device 1304 in three-dimensional space known, the computing device 1302 or robotic device may determine the location and orientation of the patient's bone 1306 in relation to the robotic device. Further still, the computing 1302 or robotic device 1304 may know the dimensions and shape of the customized registration device 1404 such that the location and the orientation of the patient's bone 1306 beneath the guide (or otherwise associated with the registration device) may be determined and applied to the surgical plan received in the pre-operative stage. With the precise location of the patient's bone 1306 known by the robotic device 1304, the location and orientation of the cut plane or resurfacing in three-dimensional space may be known by the robotic device for application to the patient's bone. In this manner, the customized registration guide 1404 may aid the robotic device 1304 in locating the patient's anatomy and in aiding the surgeon in performing the arthroplasty procedure.

As should be appreciated, the above method and system removes the need for the registration procedure described in relation to FIG. 12 above. Rather than applying a probe tool to various locations on the patient's bone to register the bone location with the robotic device 1304, the registration guide 1404 may provide the registration information to the robotic device instantaneously. This may eliminate the time consuming and potential errors that occur during the registration process of the arthroplasty procedure. In addition, because the registration information does not need to map to a three-dimensional model of the patient's anatomy, the generation of the three-dimensional model may be eliminated from the pre-operative phase. The improvement in speed and accuracy of the arthroplasty procedure utilizing a customized registration device may reduce the potential drawbacks of previous robotic-assisted arthroplasty procedures.

Figure 18:
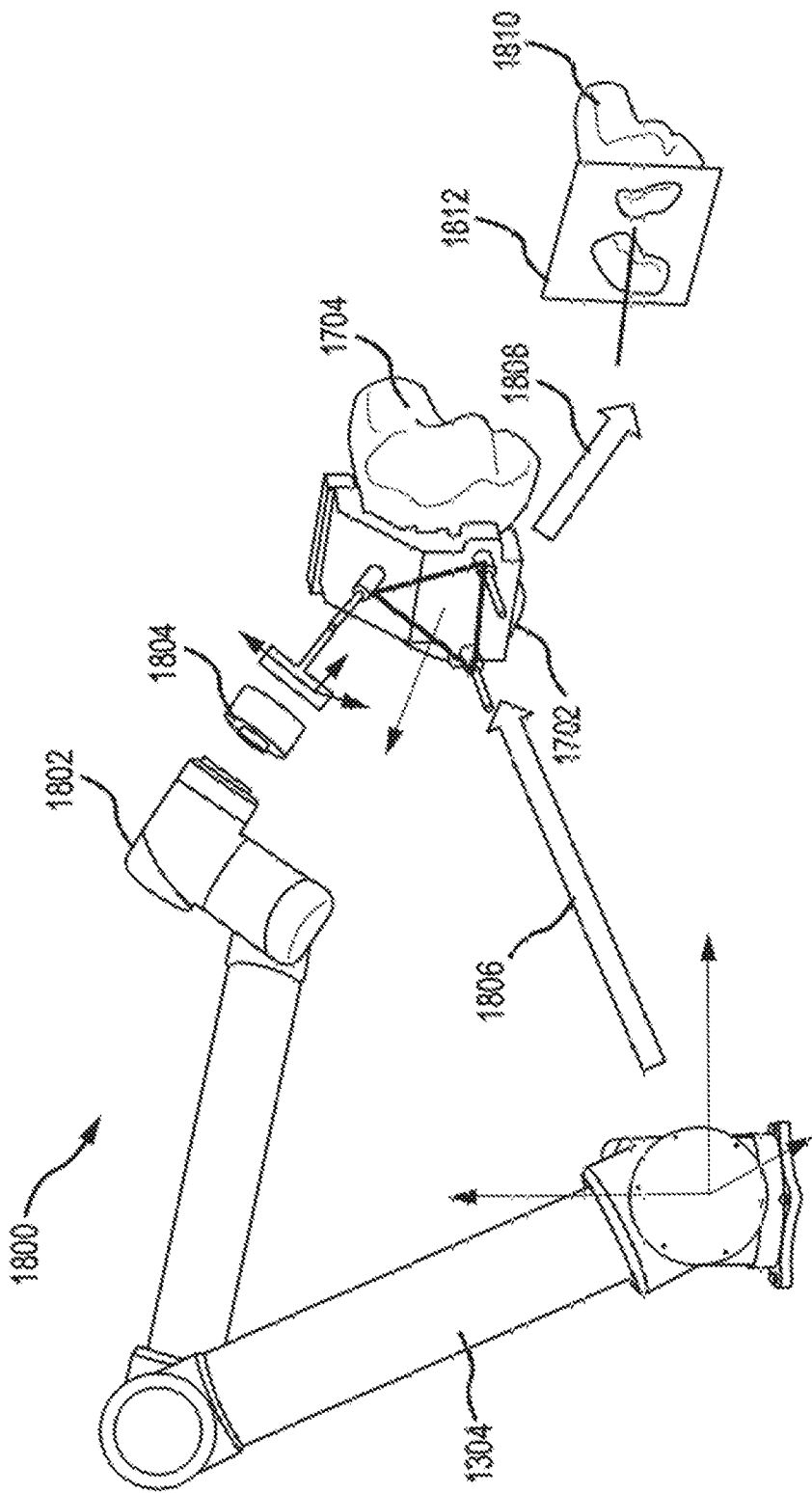
FIG. 18 is a system diagram illustrating an intra-operative procedure utilizing a customized registration device for a robot-assisted arthroplasty surgical procedure in accordance with another embodiment.

In another instance, an optical locator device 1308 may also be removed from use during registering of the patient's location with the robotic device 1304. In particular, FIG. 18 is a system diagram illustrating an intra-operative procedure utilizing a customized registration device for a robot-assisted arthroplasty surgical procedure in accordance with another embodiment. The system 1800 may include a robotic surgical-assistance device 1304 as described above for performing a resection or resurfacing of the patient's bone 1704 during the arthroplasty procedure. To register the location and/or orientation of the patient's bone 1704 for the resection, the robotic device 1304 may utilize a customized registration guide 1702 as discussed above. More particularly, the robotic device 1304 may mate the registration guide 1702 with the patient's bone 1704. In one example, the surgeon may aid or vision system with object recognition software may guide the robotic device 1304 in placing the registration device 1702 onto the patient's bone 1704 either through an initial placement of the registration guide onto the bone while attached to the robotic device 210 or by locating the robotic device 1304 in an initial position from which the device may place the guide onto the bone. For example, the robotic device 1304 may include a guide mounting end 1802 that includes a force or torque sensor 1804 and a mating mechanism for mating with a portion of the reference guide 1702. The robotic device 1304 may be moved or oriented such that the mating mechanism of the mating end 1802 may connect to the registration guide 1702 on or near the patient's bone 1704. In general, any mechanical connection between the robotic device 1304 and the registration guide 1702 may be used to mate the guide with the robotic device for mapping of the location of the guide in relation to the robotic device.

Once connected, the robotic device 1304 or the surgeon may perform a mating procedure for moving the registration guide 1702 into position on the patient's bone 1704. For example, the registration guide 1702 may mate to the patient's femur through a process of placing the guide onto the patient's bone, rotating the guide in a first direction for proper placement, and translating the guide 1702 vertically to lock the guide in place on the bone 1704. Different locking maneuvers may be developed for the various registration guides 1702 discussed above to lock the guides in place on the respective bone portions. These locking steps or maneuvers may be provided to the surgeon or programmed into the robotic device 1304 for proper placement of the registration guides on the respective patient bone portions.

In some instances, the robotic device 1304 may include the torque sensor 1804 at the mating end 1802 of the robotic device. The torque sensor 1804 may provide force and/or torque measurements to the robotic device 1304 or other computing device for placement of the registration guide 1702 onto the patient bone 1704. For example, the customized registration device 1702 may attach to the torque sensor 1804 via a ball probe or other mechanism that translates forces to the robotic device 1304. Upon mating of the robotic device 1304 with the registration device 1702 via the torque sensor 1804 at the mating end (end-effector) 1802, the robotic device may perform the mating procedure for the guide to ensure proper placement of the registration device on the patient bone. For example, the robotic device 1304 may be configured to move the registration guide 1702 in any three-dimensional movement with six degrees of freedom. During seating of the registration device 1702 onto the patient bone 1704, force and/or torque measurements may be accessed by the torque sensor 1804 for feedback to the robotic device 1304 on mating the guide onto the bone. In one particular example, the robotic device 1304 may be configured to place the registration guide 1702 onto the bone 1704 until a particular force against the movement of the guide is measured by the torque sensor 1802, followed by rotation of the registration guide 1702 in the first direction until a torque force measurement value is measured and vertical translation of the registration guide until a second force measurement is received. Through the torque sensor 1804, the robotic device 1304 may perform any locking procedure for the various registration guides 1702 to lock the guide onto the patient's bone 1704 for the arthroplasty procedure.

Regardless of if the registration device 1702 is placed on the patient bone 1704 prior to connecting to the robotic device 1304 or if the robotic device places the registration guide on the patient bone itself, the robotic device may determine the location and orientation of the patient's bone from the location of the registration guide. For example, the robotic device 1304 may include one or more movement sensors such that the robotic device may know, in three-dimensions, a location and orientation of the mating end 1802 of the robotic device. Further, the robotic device 1304 may receive the dimensions of the registration guide 1702 such that a normal vector for the registration guide may be calculated or determined. In addition, the robotic device 1304 may calculate or determine the location and orientation of the registration device 1702 in three-dimensional space in relation to the location of the robotic device. Thus, utilizing the location information of the robotic device 1304 and the location information of the registration guide 1702 (via the connection of the registration device to the mating end 1802 of the robotic device), the robotic device may locate the normal vector within the three-dimensional space relative to the robotic device location using inverse kinematics equation of the robot device. Further still, the calculated normal vector within the three-dimensional space may be mapped, by the robotic device 1304 or a computing device controlling the robotic device, to the normal vector of the cut plane included in the surgical plan.

As shown in the system 1800 of FIG. 18, the robotic device 1304 seats or connects to a seated registration guide 1702 on the patient's bone 1704. Mapping 1806 of the robotic device 1304 location/orientation to the location/orientation of the registration guide 1702 may provide the robotic device 1304 with the location/orientation of the patient's bone 1704 in relation to the robotic device 1304. In addition, the location/orientation of the normal vector of the registration guide 1702 may be determined from the mapping 1806. In some instances, the normal vector may be provided in the approved surgical plan or may be calculated from one or more markers on the registration guide 1702. With the location/orientation of the normal vector for the guide 1702 determined, the robotic device 1304 or computing device may map 1808 the calculated normal vector to the normal vector of the cut plane 1812 through the pre-operative surface model 1810 of the received surgical plan. By matching the determined normal vector location of the registration guide 1702 to the normal vector of the cutting plane 1812 of the surgical plan, the location/orientation of the cut plane through the patient's bone 1704 may be determined by the robotic device 1304. This cut plane location may be used during the resection of the patient's bone by the robotic device 1304, as described in more detail below.

As should be appreciated, the registration process utilizing the customized registration guide 1702 may remove the need for an optical locator during the surgery procedure. Rather than detecting optical markers on a probe device as described above, the robotic device 1304 may map the location of the registration guide 1702 that register the patient bone location to the robotic device 1304 location. The mechanical mating of the registration guide 1702 with the robotic device 1304 therefore may provide the registration for the mapping procedure, removing the need for an optical locator to locate the markers associated with the patient bone 1704. This may reduce the cost incurred for conducting the arthroplasty procedure through the removal of locating equipment (e.g., computer navigation system or imaging system) from the operation. In addition, because the exact dimensions of the registration guide 1702 are known from the milling program, inaccuracies in locating the patient bone 1704 may be reduced, improving the mapping of the cutting plane 1812 to the patient's bone in the operating space.

Figure 19:
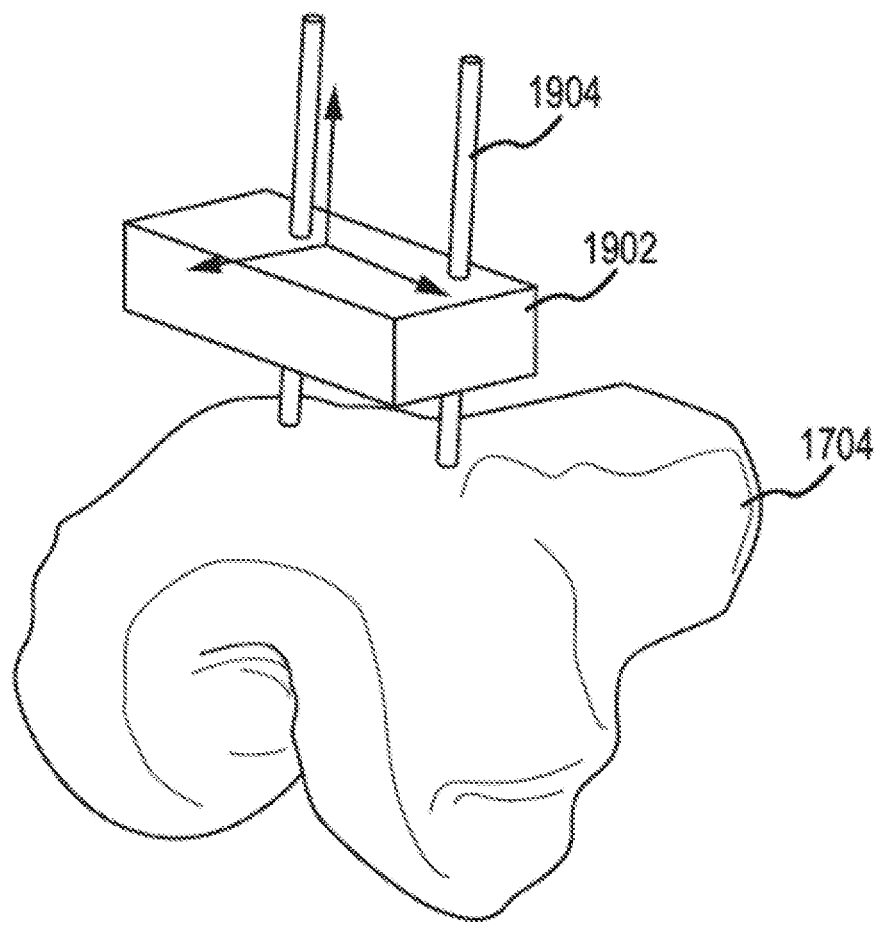
FIG. 19 is a system diagram illustrating an inertial sensor device mounted on a patient bone for use in an arthroplasty surgical procedure in accordance with one embodiment.

Returning to FIGS. 14 and 15, the intra-operative process may include mounting one or more motion sensors 1410 to the patient's anatomy in operation 1512 to detect movement of the patient during the arthroplasty procedure and adjust the determined location/orientation of the cut plane(s) according to the detected patient movement. As mentioned above, previous arthroplasty procedures may use optical markers mounted on or near the patient's anatomy. Movement by the patient during the procedure may be measured by an optical locator monitoring the reflective markers. However, movement in the direction of the line of sight between the locator and the marker may not be measured accurately and/or some obstruction may come between the locator and the markers such that not all movement may be detected, leading to an inaccurate resection of the patient's bone. In another example, illustrated in FIG. 19, one or more inertial sensors 1902 may be mounted on or otherwise attached to the patient's anatomy 1704 and wirelessly provide detected movements to the robotic device 1304 or computing device 1302 for adjustment to the determined location of the cut plane of the surgical plan in relation to the patient's bone 1704. In one instance, one or more mounting posts 1904 may be attached to the patient's bone 1704 (such as through a bone screw inserted into the resected bone). The inertial sensors 1902 attached to the bone 1704 may detect movement in six degrees, including rotation of the bone along any three-dimensional axis. Further, use of inertial sensors 1902 may remove the need for an optical locator viewing reflective markers and may provide more accurate movement detections than previous arthroplasty procedures.

In operation 1514 of the method 1500 of FIG. 15, the robotic device 1304 may perform the resection or resurfacing of the patient's bone based on the determined location/orientation of the cut plane and the surgical plan. However, through the method 1500 and devices described above, many inaccuracies of previous robotic-assisted arthroplasty procedures may be removed while reducing the expense for a health-care/surgery facility to perform the procedure.

Figure 20:
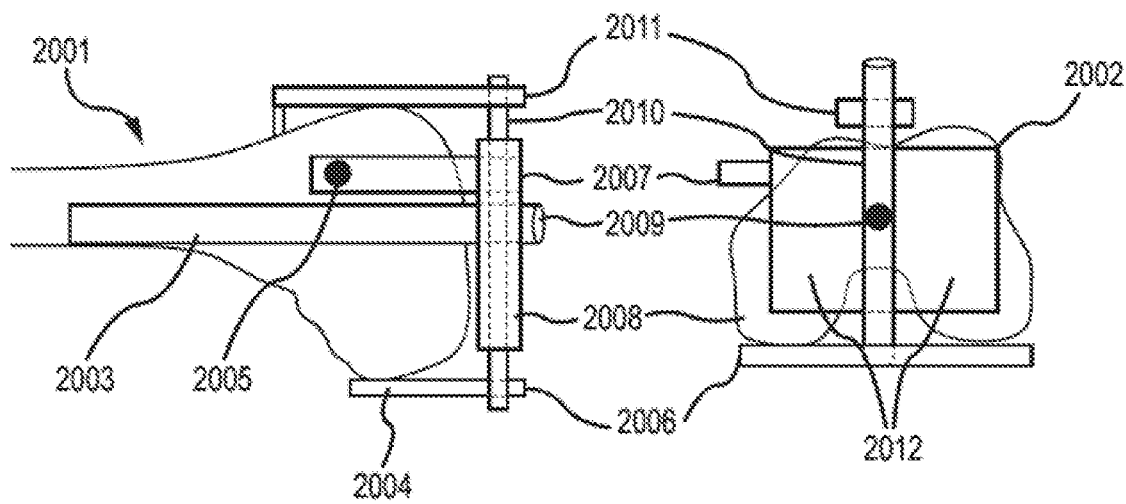
FIG. 20 is an illustration showing robotic registration of the femur using mechanical instrumentation based on a target implant position and size in accordance with one embodiment.

In some implementations, the robotic device 1304 may include an attaching surgical assistant device that attaches to some portion of the patient. For example, the robotic device may attach to the patient's bone 1704 with or without the aid of the registration device 1702 discussed above. Such a robotic surgical device may attach to the patient's bone in several ways. For example, FIG. 20 illustrates one method for mounting an attaching robotic surgical device to the patient's femur 2001 using a mechanical registration guide system. In particular, the robotic device may be mounted by first drilling a tunnel at the center of the patient's knee 2009 and inserting an intra-medullary rod 2003 to represent the superior/inferior lines in 701 and 703 (shown in FIG. 7). Next, a plate 2008 may be attached to the sliding rod 2010 to present the anterior/posterior line 707. The plate 2008 can rotate about the rod 2010 to set the varus/valgus angle and superior/inferior position of the implant. Attached to the bottom of the rod 2010 may be perpendicular plate or paddles 2006 as the lowest reference point of the medial and lateral posterior condyles 2004. The plate 2006 represents internal/external rotational angle 707 in the axial plane 702 about the center of the knee 706. Attached to the plate 2008 on the medial or lateral side is an arm 2007 approximately 40-80 mm in length that is perpendicular 2008. At the end of the arm 2007 may be two parallel drill holes 2005 that positions two drill bits or bone screws near the anterior medial of the femur 2001 that mounts the robot with the correct position and orientation for a given implant size. Drill bits or holes to mount the robot can be positioned anywhere on the medial or lateral 2002 sides of the femur based on the robot's workspace. Finally, the stylus 2011 registers the lateral 2002 anterior ridge of the femur 2001 near the inflection point, which can be raised or lowered along the rod 2010 to determine the appropriate size of the implant.

An alternate method for attaching or mounting the robotic device using a computer navigation system is briefly discussed above in relation to FIG. 12. In particular and with reference to FIG. 12, the method for attachment may use retroreflective markers 1210 and tool tip 1208 with a known offset and tool-tip diameter to register bony landmark of interest. The stereoscopic sensors 1212 uses infrared (IR) 1202 to detect reflective makers 1210 with unique configuration and applies offset to calculate the position and orientation. One of the disadvantages of the optical tracking technology is the established line-of sight. The process starts by using the handheld tool 1208 with markers 1210 to register anatomical landmarks to establish the position and orientation of the knee 1205. For example, the center of the knee, the lowest points of the medial and lateral condyles, the medial and lateral side of the femur and anterior cortex of the lateral ridge. In addition by attaching marker 1211 to the femur and rotating the knee in a circular and linear motion, the center of the hip can be estimated using a spherical profile with a certain center and radius. Once the position of the knee has been established, the corresponding implant size may be chosen based on the height and width of the knee dimensions. Based on the chosen implant size and desired position, a fixation pin 1206 with attached marker 1204 is drilled into the medial condyle that matches the correct varus/valgus angle of the implant and position of the pin relative to the center of knee and posterior condyles is placed within the workspace of the robot for the chosen implant size, discussed in more detail below. Finally, the robot's base joint 1209 with marker 1203 may be secured to the pin 1206. Before securing the robot 1201 to the pin 1206, the marker 1203 is tracking the position and orientation of the robot to match the desired implant position.

Figure 21:
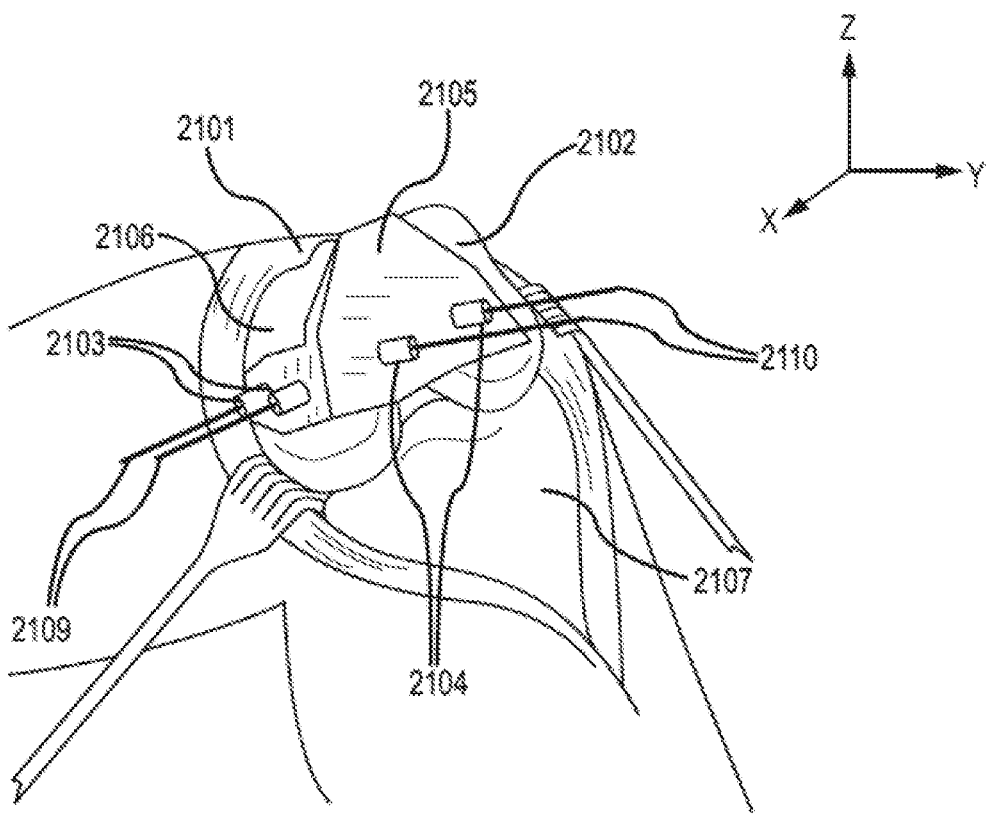
FIG. 21 an illustration showing robotic registration using a custom guide mating with the patient's anatomy in accordance with one embodiment.

In still another technique for attaching a robotic device to a patient's anatomy, FIG. 21 is a perspective illustration of patient's knee with a custom bone registration guide 2105 placed at the end of the patient femur 2102 with drill guides 2103 on the medial femur 2106 and drill guides 2104 on the distal femur 2102 using drill bits, pins, or screws. The custom bone registration guide 2105 may be generated through one or more of the techniques discussed above, such as through analysis and processing of 2D images of the patient's joint. In general, at least one drill guide is included in the custom guide 2105 to mount the robot either on the medial side, distal femur or any desired anatomical location near the surgical site. For example, a lateral uni knee replacement, the robot can be mounted on the lateral femur. For a patella-femoral joint replacement, the robot can be mounted on the anterior cortex of the femur. For femur osteotomy, the robot can be mounted on the femoral shaft near the knee joint. The same can be inferred for the tibia.

In this technique, after opening the soft tissue surrounding the knee joint, the patella is reverted to the lateral side, exposing the femur 2101 and tibia 2107. In pre-operative surgical planning, the desired position and size of the knee implant may be approved by the operating surgeon for the individual patient undergoing the surgical procedure, as described above. By using the same 2D reformatted images, the pre-operative surgical planning and customized guide design have the same anatomical coordinate system. Using this anatomical reference system, the desired position and orientation of the knee implant is subsequently translated or mapped to the customized registration guide 2105 during the production process. In one embodiment, a surface or 3D model may be generated from a series of 2D images (CT or MRI) of the patient's knee, although generation of the 3D model is not required. This is used for pre-operative surgical planning to determine the desired implant position and customized guide design. During the knee procedure, the customized guide is placed on the patient's knee matching the contact points (2D reformatted images) or surface (3D model) in the customized guide design where the implant size and position has been determined. The orientation of the drill bit tunnels (2103 and 2104) represents the position and orientation of the knee implant in all six degrees of freedom (DOF) (3 rotation+3 translation) in the pre-operative surgical planning. For example, the drill bit tunnels 2103 may set the initial the offset (along y-axis) relative to the center of femur (COF) and orientation (about the x-axis and z-axis) of the knee implant and the drill bit tunnels 2104 may set the initial the offset (along x-axis and z-axis) relative to the COF and orientation (about the x-axis and z-axis) of the knee implant. In this manner, the robot registration to the patient is established using the customized patient guide and imaging data obtained through the process described above.

Figure 22:
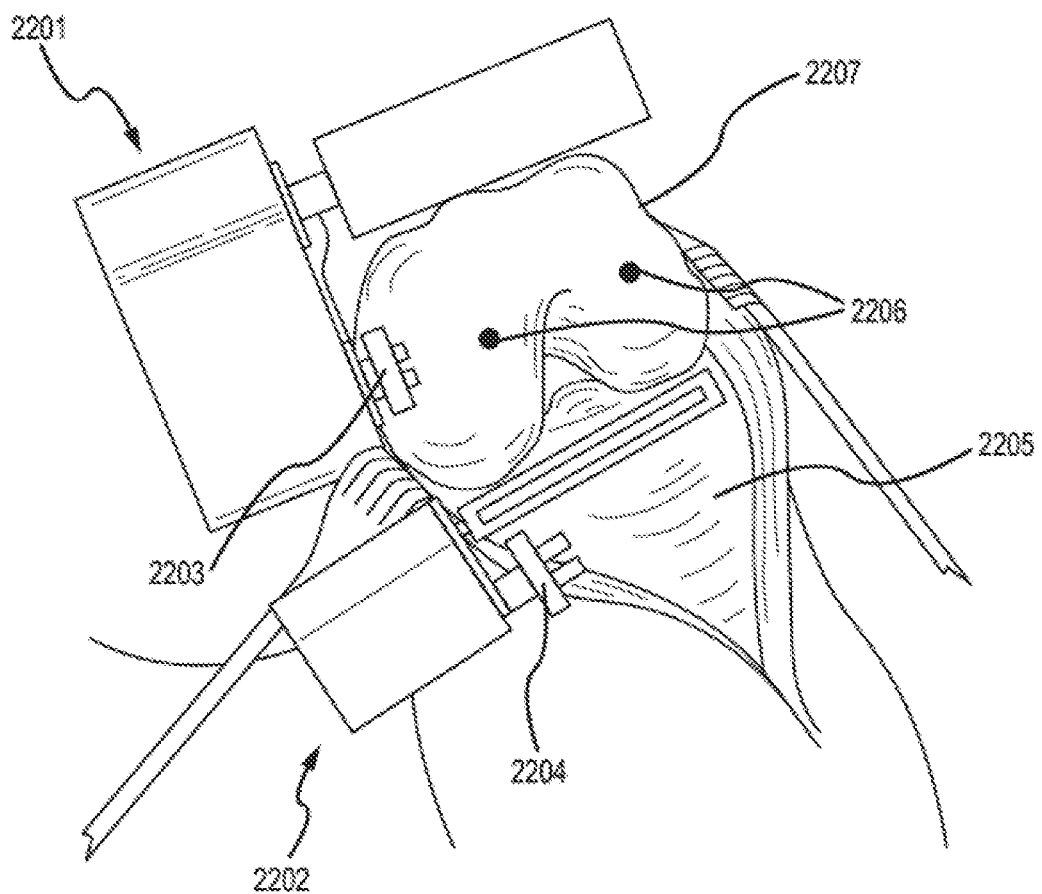
FIG. 22 is a perspective illustration of patient's knee with the robot mounted on the medial side of the femur and tibia using fixation pins with a certain incision size based on the surgical technique in accordance with one embodiment.

FIG. 22 is a perspective illustration of patient's knee with corresponding surgical robot mounted to the femur 2207 and tibia 2205 bone. Using one of the registration methods described above, the robot 2201 may be registered to the femur 2207 mounted to the medial side of the femur using two or more drill bits 2203. The drill bits 2203 generally set the position and orientation of the robot, which corresponds to the desired implant orientation and position determined pre-operatively. Similarly, in the case of the robot 2201 mounted on the distal femur, two or more pin holes 2206 may establish the desired implant position and orientation. In one embodiment, at least one robot is mounted to the bone. In another embodiment, robot 2202 is mounted on the medial side of the tibia 2205 secured by two or more drill bits 2204, which correspond to the desired tibia implant position. As discussed, the robot 2201 can be mounted anywhere on the patient's anatomy near the site of the surgical procedure with the workspace of the robot as needed to accomplish the tasks of the surgical procedure.

Aspects of the present disclosure involve methods and systems for a small robotic-assisted surgical systems mounted to the patient's anatomy. As mentioned above, the present disclosure may be applied to any region of a patient's joint as part of the orthopedic procedure. However, for ease of understanding, the discussion herein is limited to particulars of the knee as an example of the inventions relating to the present disclosure procedure and embodiments. Further, any small robotic-assisted surgical system may be used with the systems, methods, and procedures described herein. A particular small robotic-assisted surgical system for mounting on a patient's anatomy and executing a pre-operative arthroplasty plan is now described for use with the systems and methods described herein.

Figure 23:
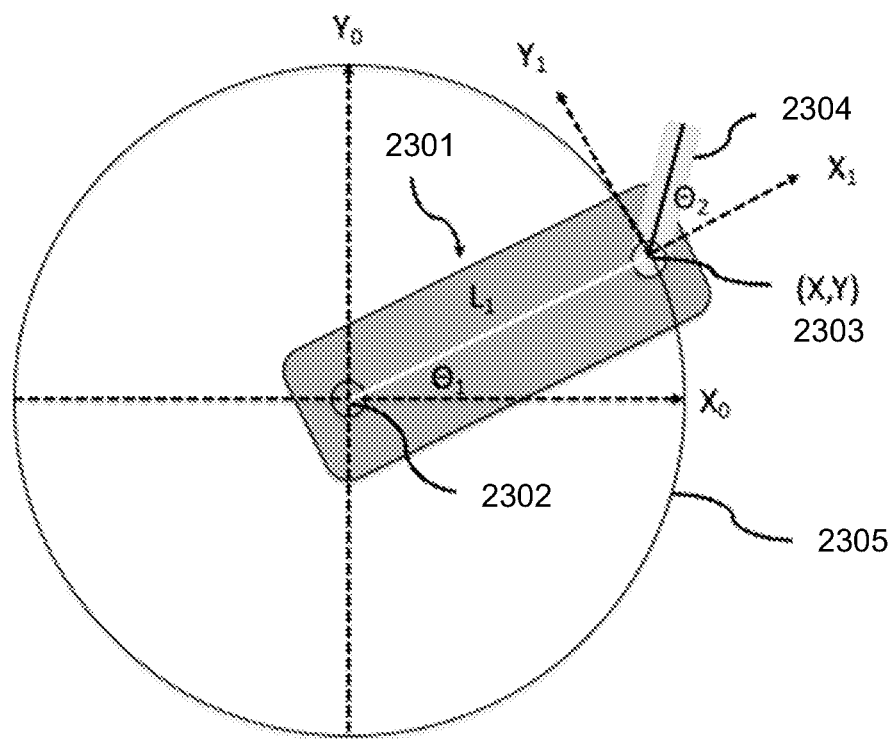
FIG. 23 is an illustration of a one-link planer robot with two Degrees of Freedom (DOF) and corresponding robot's workspace in accordance with one embodiment.

More particularly, FIG. 23 is an illustration of a one-link robot with two rotational joints ($\theta_1$, $\theta_2$) or two Degrees of Freedom (DOF). In one implementation, the robot comprises two rotation joints (el, $\theta_2$), a first joint with ($\theta_1$) at the base 2302 and second joint ($\theta_2$) at the end-effector 2303 interconnected by the body 2301 with length $L_1$. Each joint, $\theta_1$ at 2302 and $\theta_2$ at 2303, is capable of 0-360 Degree or continuous revolution. Different tools or instruments 2304 may be attached to the end-effector 2303. The tool or instrument can be oriented in any angle $\theta_2$ in (X,Y) plane or trajectory in (X,Y) space between 0-360 Degrees controlled by the joint 2303. For example, the attached to the end-effector 2303 may be a saw guide or drill guide 2304 positioned (X,Y) on the workspace 2305 and oriented at angle $\theta_2$. The workspace of the one-link robot with 2-DOF can be described by the following forward and inverse kinematic equations as follows:

Inverse Kinematics:

$$\theta_1 = \tan^{-1}(Y/X)$$

$$\theta_2 = \text{constant}$$

Where X and Y are the end-effector position (X,Y) in millimeters of the end-effector described by the coordinate system ($X_0$, $Y_0$).

Forward Kinematics:

$$X = L_1 * \cos(\theta_1)$$

$$Y = L_1 * \sin(\theta_2)$$

Where $\theta_1$ and $\theta_2$ are joint angles in Degrees of the 2-DOF robot with length $L_1$ from center of rotational joint 2302 to center of rotational joint 2303.

The perimeter or diameter of the workspace may be defined by link $L_1$. In some implementations, $L_1$ is a fixed length that accommodates different implant sizes (height) with different internal geometries. The base or center of the workspace defined by a circle with radius $L_1$ can be positioned in any location on the medial 2206 or lateral side of the femur to accommodate different knee implant sizes and internal geometries. The workspace requirement is described in more detail below for a given robot design depending on the knee procedure.

Figure 24A:
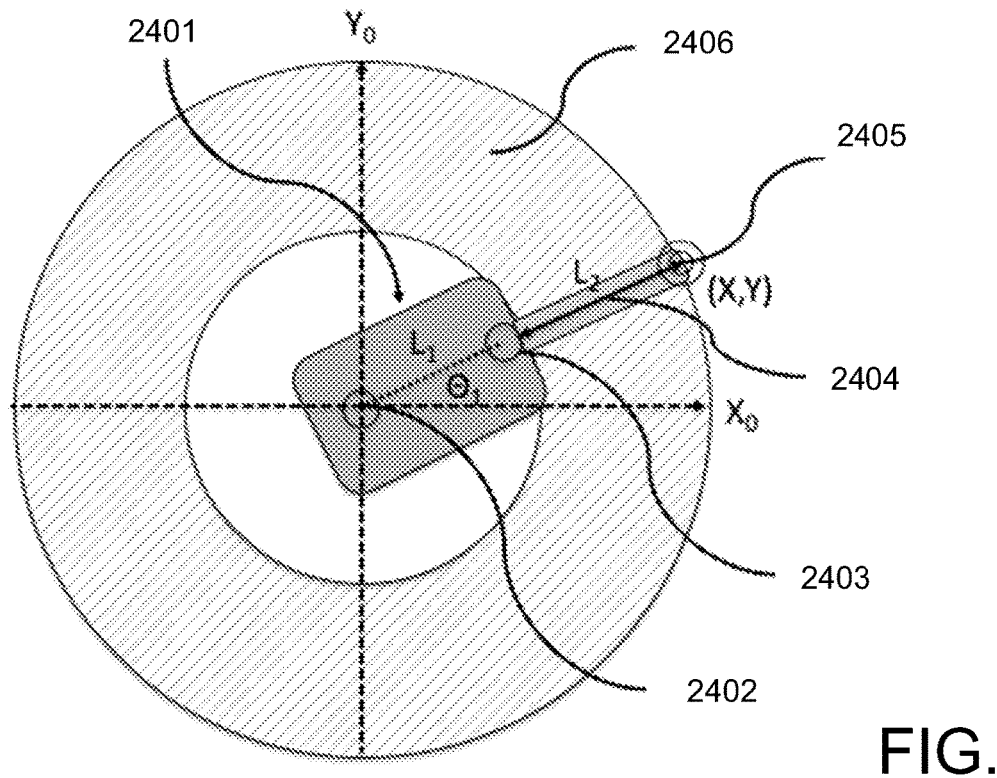
FIG. 24A is an illustration of cylindrical robot with two Degrees of Freedom (DOF) and corresponding robot's workspace in accordance with one embodiment.

FIG. 24A is an illustration of a cylindrical robot with one rotational joint and one linear joint (2-DOF). Similar to the system illustrated in FIG. 23, a linear actuator 2404 with a variable length $L_2$ from 0 to approximately 50 mm may be attached to the end-effector 2403. In one embodiment, the linear arm/actuator can be static or dynamic, meaning the control or adjustment of length $L_2$ can be either driven by a servo motor with universal gears 2403 or adjusted manually with a sliding arm or a fixed length arm. In another embodiment, the linear arm 2404 can be a piston actuated with air or hydraulics, tensioning device such as a spring and/or force/pressure sensor or strain gauge attached to a fixed arm. Base joint, $\theta_1$ in 2402 is capable of 0-360 Degree or continuous revolution. Different tools or instruments can be attached to the end-effector 2405, such as power tools such as mills, drills or cutting guides or instrument/sensors, such as optical markers, cameras or probes. The workspace of the 2-DOF robot can be described by the following forward and inverse kinematic equations as follows:

Inverse Kinematics:

$$\theta_1 = \tan^{-1}(Y/X)$$

$$\sqrt{L_2 = X^2 + Y^2} - L_1$$

Where X and Y are the position in millimeters of the end-effector described by the coordinate system ($X_0$, $Y_0$), $\theta_1$ is the base joint angle in Degrees and $L_1$ is the fixed length of the base joint and $L_2$ is variable length of the linear arm.

Forward Kinematics:

$$X = (L_1 + L_2) * \cos(\theta_1)$$

$$Y = (L_1 + L_2) * \sin(\theta_1)$$

Where $\theta_1$ is the joint angle in Degrees of base joint with fixed length $L_1$ and $L_2$ is the variable length of linear arm.

The area of the workspace 2406 may be defined by $L_1$ to ($L_1 + L_2$). Ideally, $L_2 > L_1$ where $L_1$ is a fixed length while $L_2$ is variable in length that accommodates different implant sizes (height) and internal geometries. The base of the robot or center of the workspace defined by 2402 can be positioned in any location on the medial, lateral or anterior side of the femur to accommodate different surgical techniques, knee procedures, knee implant sizes and internal geometries. In one embodiment, the robot in FIG. 24 may be mounted on the medial side of the tibia shown in FIG. 22 to cut the tibia bone shown in FIG. 8 to substitute with an implant as part of the uni-knee procedure.

Figure 24B:
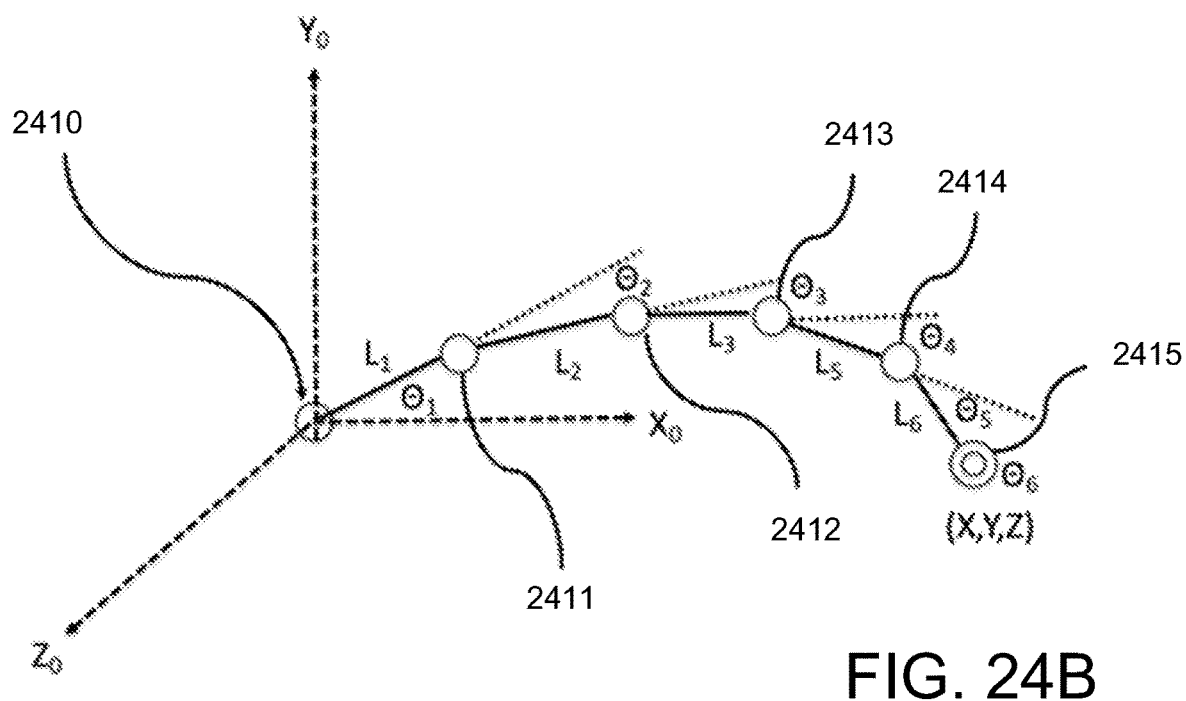
FIG. 24B is an illustration of five-link with six Degrees of Freedom (DOF) corresponding robot's workspace in accordance with one embodiment.

FIG. 24B is an illustration of a 6-DOF robot (five rotation and six linear joints) with a spherical workspace described by radius ($L_1 + L_2 + L_3 + L_4 + L_5 + L_6$). Each joint 2410-2415 ($\theta_1, \theta_2, \theta_3, \theta_4, \theta_5$ and $\theta_6$) is capable of 0-360 Degrees or continuous revolution. In one embodiment, the robot is an nth DOF robot. In another embodiment, each link of the robot ($L_1$, $L_2$, $L_3$, $L_4$, $L_5$ and $L_6$) is either fixed, variable or any combination of fixed and variable length to accommodate the workspace and implant geometries. The workspace of the 6-DOF robot can be described by the Denavit-Hartenber (D-H) parameters and D-H matrices can be used to calculate the forward and inverse kinematic equations of the robot. In general, the D-H convention can be used for any nth DOF robot.

Figure 25:
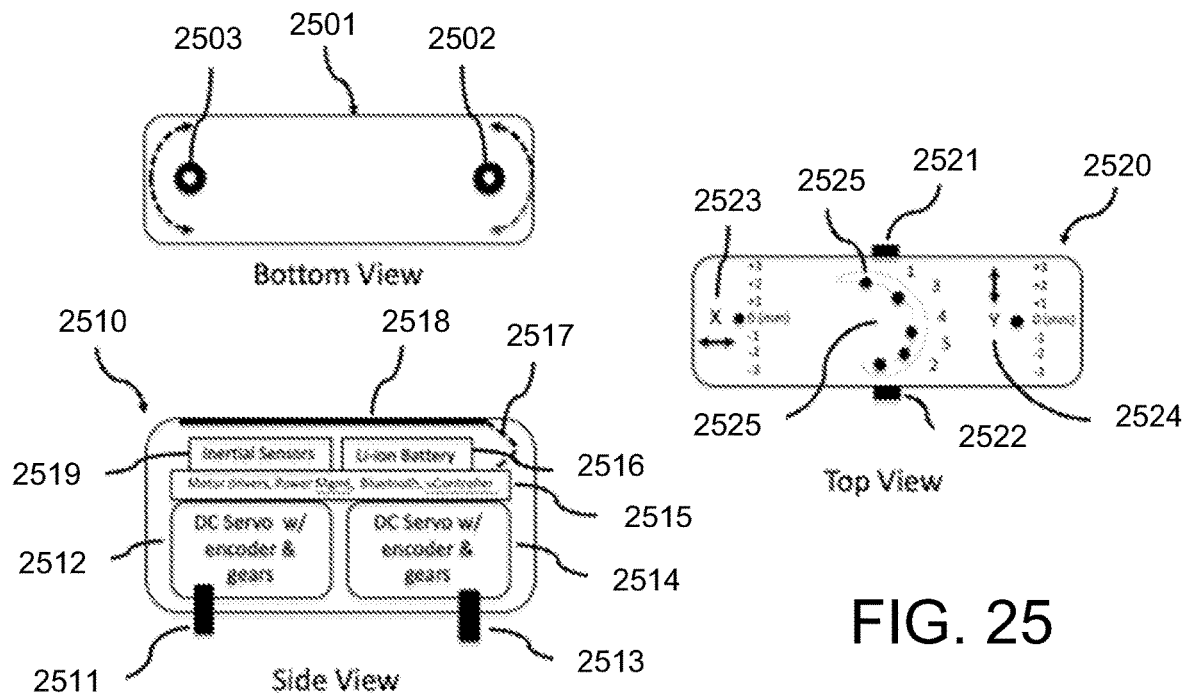
FIG. 25 are perspective illustrations of the robot in FIG. 23 with internal electro-mechanical and external controls of 2-DOF robot in accordance with one embodiment.

FIG. 25 are perspective illustrations of a small, surgical assistant robot according to the embodiments described herein. In particular, illustrated are internal electro-mechanical and external control/display views of a 2-DOF robot. Beginning with the bottom view, the robot 2501 includes two rotational joints at 2502 and 2503 driven by two DC or AC, brush or brushless servo motors. The robot can be rectangular or any shape, such as square, elliptical or other geometric shapes, to accommodate the internal electro-mechanical and incision size of a particular surgical technique or procedure. The robot external shell or case can be plastic, aluminum, carbon fiber or other materials to house the internal subassemblies. A cross-sectional or side view of the robot in 2510 shows the internal subassemblies of the robot, such as sensors, electro-mechanical, electrical, and power system. The robot may include two motors with or without internal gears for increasing or decreasing the torque/speed and encoders (optical or mechanical) to measure the position, velocity or acceleration of the motors, 2512 and 2514 respectively, as feedback control of the motors. The input and output signals are connected to the electronics 2525, which comprises of communication module (wired or wireless), power management, motor driver electronics, micro-controller and other electronics and sensors (e.g., temperature and/or current sensors) to monitor the operation, safety, and status of the robot. The robot is powered by internal rechargeable lithium ion or similar chemical batteries 2516 with voltage in the range of approximately 5 to 48 volts that is removable, rechargeable or replaceable. In one embodiment, the battery or power supply is housed externally. A cable or wireless transceiver is connected to the robot that provides power to the electro-mechanical systems. In another embodiment, the motor, gears, and sensors are housed inside the robot while the electronics, micro-controller, and power are housed externally through a wired cable or wireless transceiver.

In addition, sensors 2519, such as, inertial measurement units (accelerometers, magnetometers and/or gyroscopes), temperature or other sensors are housed inside the robot mounted on the PC board. Typically, higher voltage equates to faster speed while higher current equates to torque. An external display module 2518 provides visual indications as well as controls for the operating surgeon during the procedure. The signals to the display module may be provided by a bus cable 2517. All of the internal subassemblies as a single unit can be removed from the external case 2501 by disconnecting the bus 2517. Finally, the top view of the robot 2520 provides the I/O control and visual displays for the operating surgeon. One or more buttons or other input devices such as voice command, touch sensor or other types of interface, that controls the robot's motion. For example, pressing the button 2521 once advances the robot from position 1 to position 2 indicated by the LEDs in 2525 while pressing the button 2522 once will move the robot from position 2 to position 1 as shown in FIG. 31. In one embodiment, the pressing the button 2521 moves the robot's end-effector linearly along the X-axis 2523 in 0 to 1 mm increments indicated by the LEDs and similarly by pressing the button 2522 moves the robot linearly along the Y-axis as in 0 to 1 mm increments indicated by the LEDs described in FIG. 23 within the robot's workspace. In one embodiment, the LEDs can be LCDs or other types of touch sensitive displays (e.g., capacitive). In still another embodiment, holding down the button for more than 1 second changes the current state of the robot from 2523 to 2524 to 2525 in any order or sequence whereas pressing the button once advances the position of the robot. The entire external shell or case of the robot is sterile and can be single-use or re-usable, which is sealed to prevent water entering the internal subassemblies or contaminating the patient from the re-usable non-sterile robot.

Figure 26:
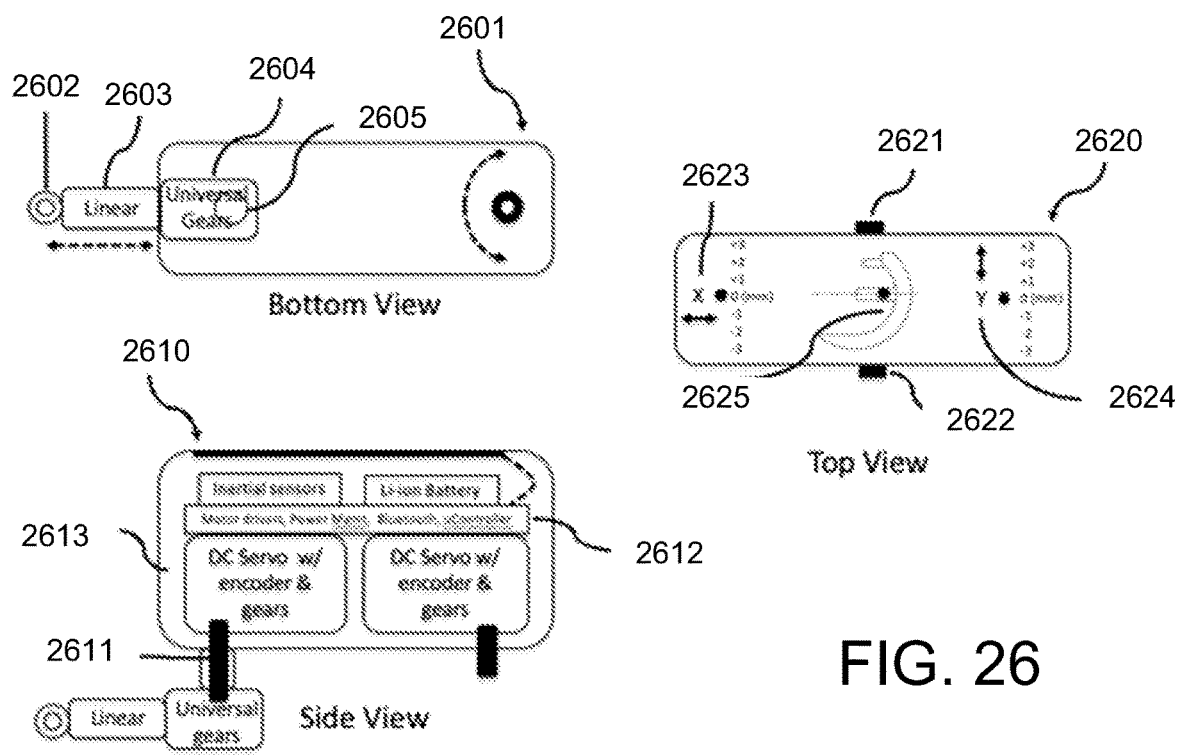
FIG. 26 are perspective illustrations of the robot in FIG. 24 with internal electro-mechanical and external display views of 2-DOF robot in accordance with one embodiment.

FIG. 26 includes perspective illustrations of a small, surgical assistant robot's internal electro-mechanical and external views of 2-DOF robot (one rotation+one linear joint). Similar to FIG. 25, the bottom view of robot 2601 comprises of two rotational joints 2503 and 2502. At either rotation joint a linear actuator 2604 may be connected to the motor 2605 and universal gears 2604 which allows the rotational joint to drive the variable linear actuator 2603 using a 90 degree gear box. Connected to gears 2604 is a linear actuator 2603, which can extend and retract within the workspace. Attached to the end of the linear actuator is the end-effector 2602. Next, the side view 2610 is similar to FIG. 25 except the axle 2611 of the DC servo motor 2613 is connected directly to the internal gears 2604 of linear actuator. The position of the linear actuator is controlled by the DC servo 2613 with encoders and gears. For example, one revolution of the DC servo motor may equate to a certain arm length 2603. The universal gears 2604 and linear arm 2604 can be detached or removed from the motor axle 2611. In one embodiment, the robot in FIG. 15 is the same as FIG. 26 except attached to the end-effector is a mechanical actuator. Finally, the top view of the robot 2620 includes one or more buttons, 2621 and 2622, and visual display 2625 of the current state of the robot's motion: linear along X-axis 2623, implant positions and along Y-axis 2624. In one embodiment, the visual display 2625 is an LCD that can be programmed to display different implant image, text instructions or real-time data based on the surgical procedure.

Figure 27:
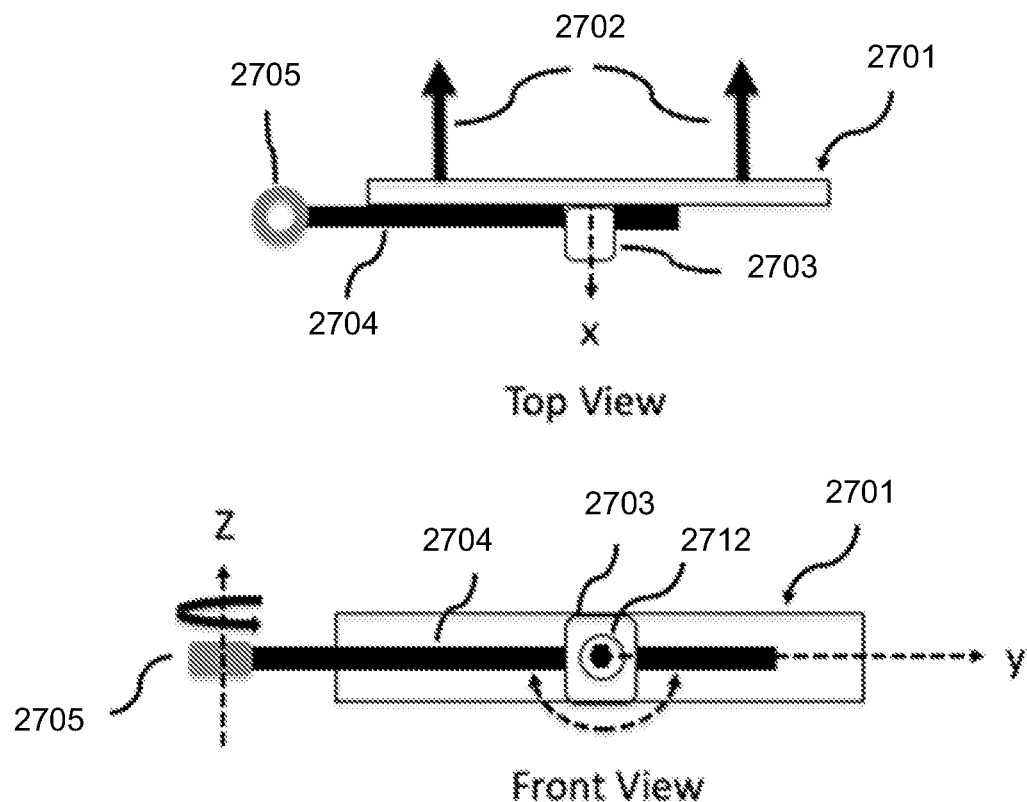
FIG. 27 are perspective illustrations of the robot's fixtures providing additional linear and rotational adjustments and display in accordance with one embodiment.
Figure 28:
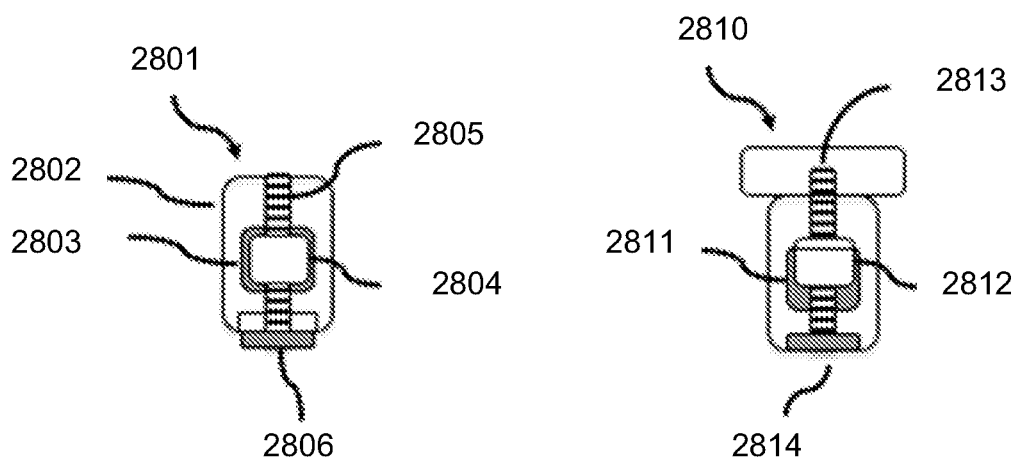
FIG. 28 are perspective illustrations of the locking mechanism for securing the robot to the patient's anatomy through a fixation plate in accordance with one embodiment.

FIG. 27 are perspective illustrations of a fixture attached to the robot's base as shown in FIGS. 25 and 26. Beginning with the top view, the fixture includes a plate 2701 and two perpendicular pegs 2702 that are matched to the distal drill holes 1206. On the other side of the plate is a locking mechanism 2703 attached to the plate along with a tunnel on the side that allows the bar 2704 to be inserted and secured to the plate 2701. The bar 2704 can be square, round or any other shape and the position can be adjusted by sliding along the y-axis. At the end of the sliding bar 2704 is a hinge 2705 that is free to rotate about the z-axis and can be secured in place with a locking mechanism. In one embodiment, the hinge 2705 includes a sensor to measure the angle of the rotating hinge. In another embodiment, the hinge is a DC servo motor, fixed at certain angle, encoder or protractor. Continuing with the front view of the fixture 2701, the locking mechanism 2703 includes a hex screw 2712 that secures the bar 2704 to the fixture. In addition, the locking mechanism allows the bar 2704 to rotate about the x-axis. In one embodiment, the locking mechanism 2703 includes a sensor to measure the angle of rotation. Finally, the hinge 2705 allows the fixture to rotate about the z-axis. The locking mechanism will be described in more detail in FIG. 28. More particularly, FIG. 28 are perspective illustrations of the locking mechanism 2801 for securing the robot to the patient's femur through a fixation plate 2810. The locking mechanism may be cylindrical in shape 2802 and include a window 2803 that extends across the cylinder. A screw 2805 that is approximately the same length as the cylinder 2802 may be included inside the cylinder 2802. Attached to the middle of the screw is a square or round tubing that is the same, bigger or smaller in diameter or cross-section than the window 2803. At the other end of the screw is a head 2806, when tightened is flush with the cylinder 2814. When the screw is tightened, the tunnel 2812 travels along the direction of the screw and the bar 2804 is pinched between the tunnel 2812 and window 2811 locking the bar from sliding. In addition, the screw 2805 may be threaded into to the fixture 2810 locking the bar from rotating. In one embodiment, the locking mechanism in FIG. 28 without the plate 2810 may be the same structure as that illustrated in FIG. 20 as arm 2007, where arm 2006 is the arm 2804 of FIG. 28. The locking mechanism may be part of the plate that is secured to the bone using two drill bits shown in 2203 and 2204 of FIG. 22.

Aspects of the present disclosure involve methods and systems for a small robotic-assisted surgical systems mounted to the patient's anatomy. To aid in the description below, a brief discussion of the different robot configuration from 2-DOF to 6-DOF including mechanical fixture, force/torque sensors and visual indicators such as a protractor is now included. As mentioned above, the present disclosure may be applied to any region of a patient's joint as part of the orthopedic procedure. However, for ease of understanding, the discussion herein is limited to particulars of the knee as an example of the inventions relating to the present disclosure procedure and embodiments.

Figure 29A:
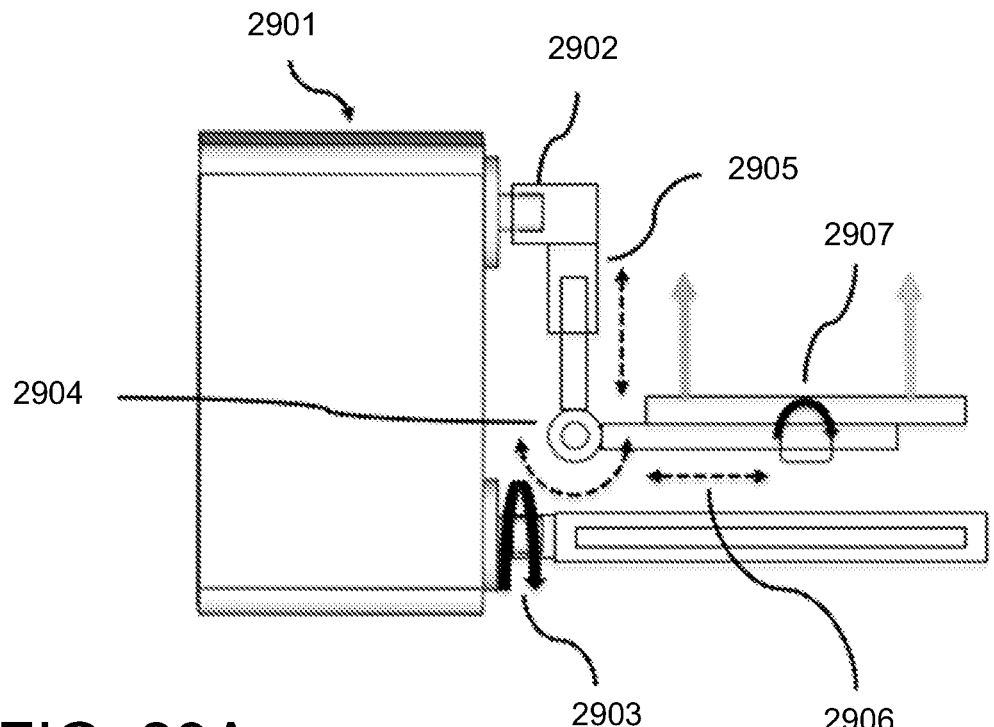
FIG. 29A is a perspective illustration of the robot showing the 5 DOF robot secured to end of distal end of the femur in accordance with one embodiment.
Figure 29B:
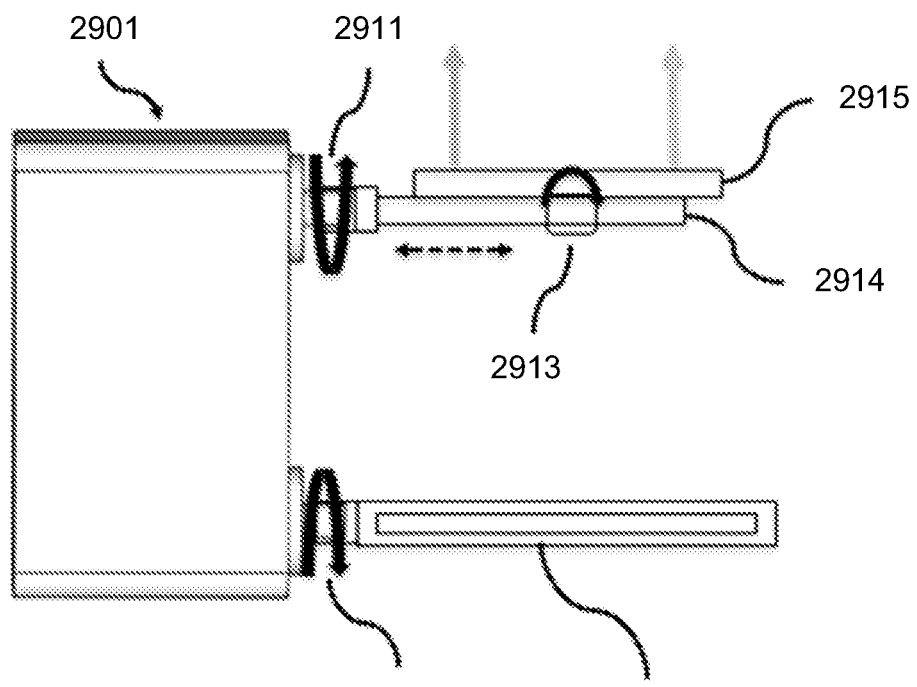
FIG. 29B is a perspective illustration of the robot showing the 4 DOF robot secured to the fixation plate attached to the distal end of the femur in accordance with one embodiment.

FIG. 29A is a perspective illustration of the robot showing the 2-DOF robot 2901 in FIG. 26, with the 3-DOF fixture described in FIG. 27 attached to the robot's base secured to the distal end of the femur. The 5-DOF includes the robot device in FIG. 26 with one rotational joint 2902 and one linear actuator 2905, plus the fixture with rotating hinge 2904, sliding bar 2906 and rotating locking mechanism 2907. In one embodiment, the hinge 2904 is fixed at right angle (90 Degrees) or perpendicular to the sliding arm 2906. In another embodiment, the locking mechanism 2907 is fixed at 0 Degrees. The robot 2901 can detached from structure 2902 and structure 2903 and reconfigured for a different procedure or application. Similarly, FIG. 29B is a perspective illustration of the robot showing the 2-DOF robot 2910 in FIG. 26, with the 2-DOF fixture without the hinge described in FIG. 27 attached to the robot's end-effector 2911 secured to the distal end of the femur. The 4-DOF includes the robot described in FIG. 25 with two rotational joints, 2911 and 2912, plus the fixture with rotating locking mechanism 2913, sliding bar 2914, and plate 2915 secured to the bone after the distal femur resection. Similarly, the robot 2910 may be detached from 2911 and 2912 and reconfigured for a different procedure or application.

Figure 30:
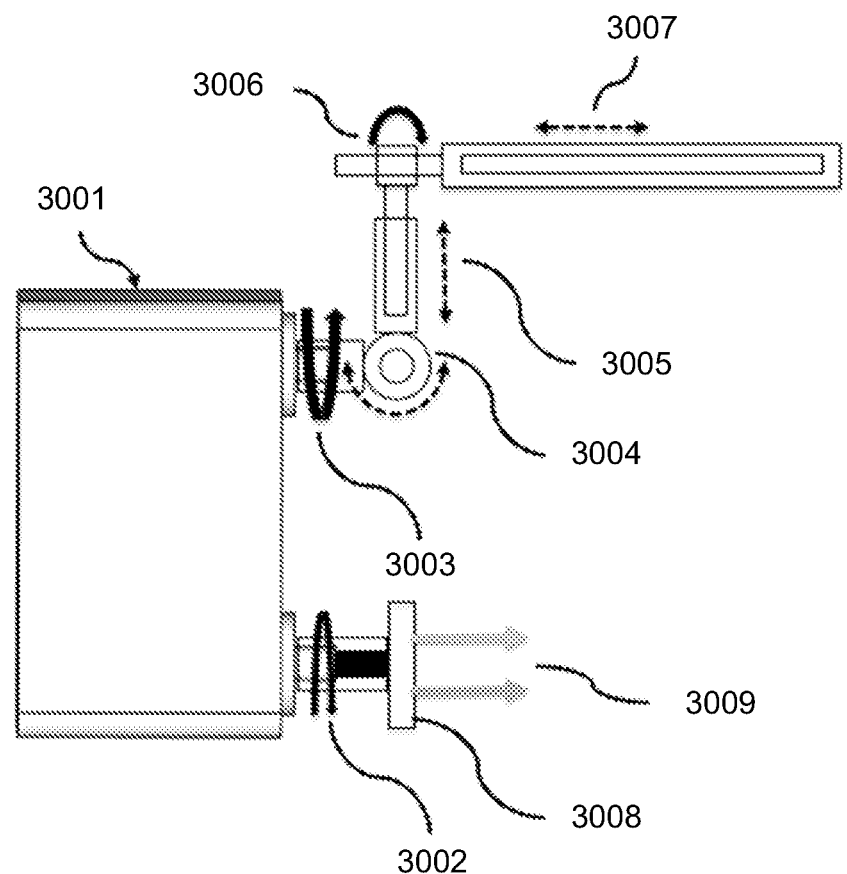
FIG. 30 is another perspective illustration of the robot showing the 2-DOF robot+4-DOF end-effector (six total DOF) secured to the fixation plate attached to the patient's anatomy in accordance with one embodiment.

FIG. 30 is another perspective illustration of the robot showing the 2-DOF robot 3001, with a 4-DOF robot attachment attached to the end-effector secured to the patient's anatomy 3009. The 6-DOF includes the robot device described above in FIG. 25 with two rotational joints 3002 and 3003 and a rotating hinge 3004, linear actuator 3005, locking mechanism 3006 and sliding bar 3007. The robot device in FIG. 30 allows maximum flexibility with 6-DOF. In one embodiment, the hinge 3004 is fixed say at right angle (90 Degrees), which becomes a 5-DOF robot. In another embodiment, the locking mechanism 3006 is fixed, such as at 0 Degrees, which becomes a 5-DOF robot. In another embodiment, the hinge 3004 and locking mechanism 3006 are both fixed, which results in a 4-DOF robot. In another embodiment, a second 2-DOF robot similar to 3001 is attached to the hinge 3004 in a perpendicular fashion with one of its rotational joints, which becomes 4-DOF. It is understood that different attachments, sensors, tools or another same or different robot can be attached to the robot's rotational joints described in FIG. 25. The attachments can be of any degrees of freedom in the form of a linear actuator, another robot 3001, simple cutting guide or drill guide to more complex mechanical fixtures or robotic grippers.

Aspects of the present disclosure involve methods and systems for a small robotic-assisted surgical systems mounted to the patient's anatomy. To aid in the description below, a brief discussion of robot calibration and different robot positions for bone resection or milling is now included. As mentioned above, the present disclosure may be applied to any region of a patient's joint as part of the orthopedic procedure. However, for ease of understanding, the discussion herein is limited to particulars of the knee as an example of the inventions relating to the present disclosure procedure and embodiments.

Figure 31A:
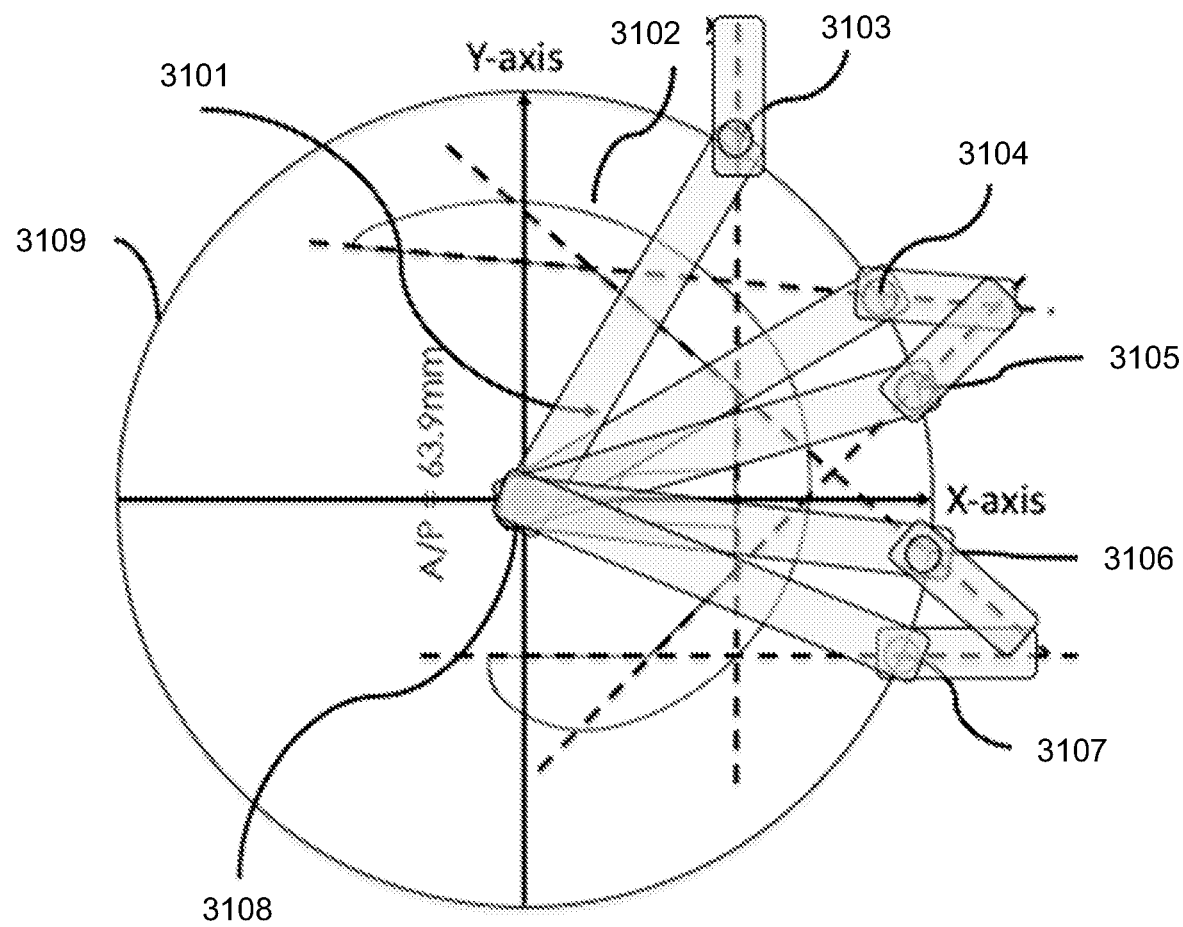
FIG. 31A is an illustration of a robot and workspace in 2D showing the different arm configurations matching the five internal geometries of the femoral prosthesis mounted on the side of the femur in accordance with one embodiment.

FIG. 31A is an illustration of a 2-DOF robot 3101 showing five different arm configurations within the robot's workspace 3109 matching the five internal geometries of the femoral component 3102. Starting with position one 3103, the (X,Y) position 3103 is defined as the intersection of the distal line 604 (of the illustration of FIG. 6) and robot's workspace 3109. Using the inverse kinematic equation described in FIG. 23, the joint angle $\theta_1$ for link 1 at reference 3108 can be calculated. The angle $\theta_2$ for the cutting guide is determined based on the internal geometry of 604. Similarly, the end-effector positions 3104-3107 can be calculated using the inverse kinematic equation described in FIG. 13 and corresponding angle for the internal geometry of the knee implant 3102. For each implant brand and size, the end-effector (X,Y) position is different and can be stored in the robot's memory or transmitted to the robot prior to the procedural. In one embodiment, a look-up table of different implant size and brand is stored in the non-volatile memory of the robot. When the surgeon approves the surgical plan with the desired implant position, size and brand, the robot's arm and cutting guide are automatically configured for each implant internal geometry. In addition, the surgeon can adjust the cutting guide position displayed in FIG. 25 using the buttons 2531 and 2522 in terms of X and Y positions. Using the inverse kinematic equation described above for a 2-DOF robot, the corresponding angles for rotational joints 1 and 2 can be calculated. In addition, the workspace 3109 also defines the length of the robot $L_1$ in 2301. Ideally, the same robot 3101 should be able to accommodate a large number of implant brands and sizes regardless of the location of the base joint which can be adjusted for each patient's anatomy and surgical technique.

Figure 31B:
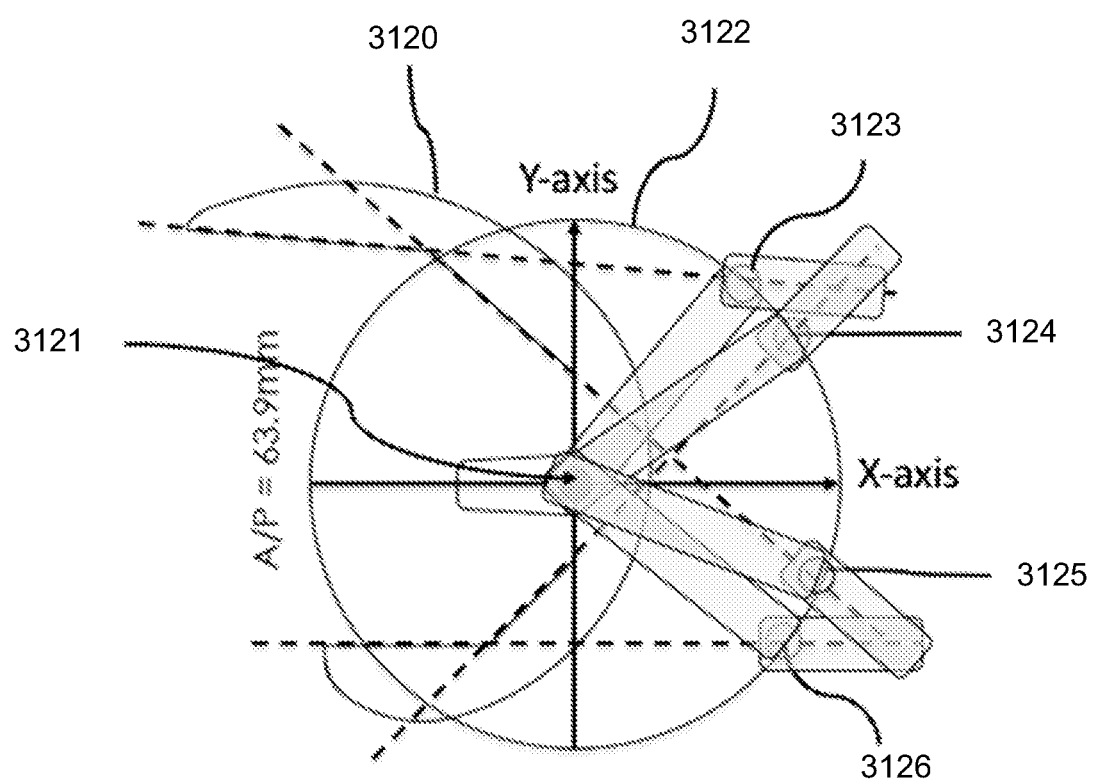
FIG. 31B is an illustration of a robot and workspace in 2D showing the different arm configurations matching the four internal geometries of the femoral prosthesis mounted on the end of the femur in accordance with one embodiment.

FIG. 31B is an illustration of a 2-DOF robot 3102 similar to 3101 showing four different arm configurations within the robot's workspace 3122 matching the four internal geometries of the femoral component 3120. In this illustration, the base position 3121 of the 2-DOF robot 3102 was shifted along the x-axis towards the inferior end of the femur. By doing so, the diameter of the robot's workspace 3122 can be reduced and still accommodate the end-effector position and angles 3123-3126 using the same 2-DOF robot. As discussed above, the robot's workspace is defined by length $L_2$ of the robot in FIG. 23. In addition, the angle $\theta_2$ for the cutting guide has two possible solutions: $\theta_2$ and $\theta_2 \pm 180°$. This would allow a miniature bone-mounted surgical robot for minimally invasive surgery while accommodating a larger number of implant brand and sizes. In one embodiment, the design of the robot can be optimized for each implant brand and size. In another embodiment, the rotational joints of the robot in FIG. 25 will only need to accommodate angles from 0-180 Degrees thus reducing the cost and design complexities of the robot.

Figure 31C:
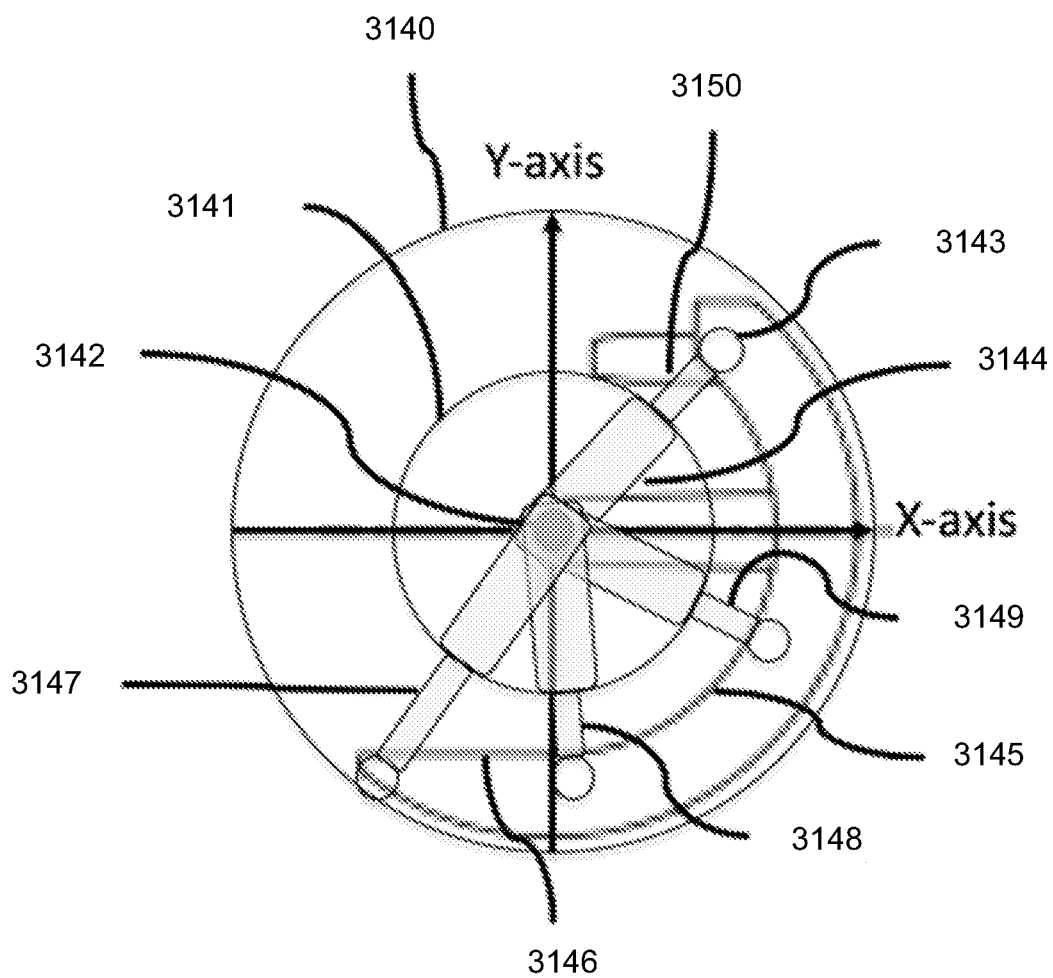
FIG. 31C is an illustration of a robot and workspace in 2D showing the different arm configurations matching the continuous internal geometries of the uni femoral prosthesis mounted on the side of the femur in accordance with one embodiment.

FIG. 31C is an illustration of the 2-DOF robot (one rotational+one linear joint) similar to FIG. 26 showing the uni-knee implant 3145 and the robot's workspace between 3140 and 3141 matching the continuous internal geometries of the uni-knee femoral component 3145. In this illustration, the base position 3142 of the 2-DOF robot base 3142 is positioned to accommodate the shape of the implant. In one embodiment, the robot's workspace is fixed, but the base position 3142 is repositioned to accommodate different implant geometries and size. The robot's end-effector (X-Y) position 3143 follows a continuous profile as the base joint 3144 rotates in a clock-wise or counter-clockwise motion along with the linear actuator 3150 while following the profiles 3145 and 3146 which can described using an nth degree polynomial or look up table with a series of X-Y points. For example, using the inverse kinematic equation, the base joint angle along with the linear actuator position 3143, 3149, 3148 and 3147 can be calculated to follow the end-effector position. In addition, the surgeon can adjust the position of the end-effector in the X and Y direction shown in FIG. 26 in 1 mm increments. For example, the surgeon would like to remove more bone along the X or Y direction by adding an offset to the implant profile.

Figure 32:
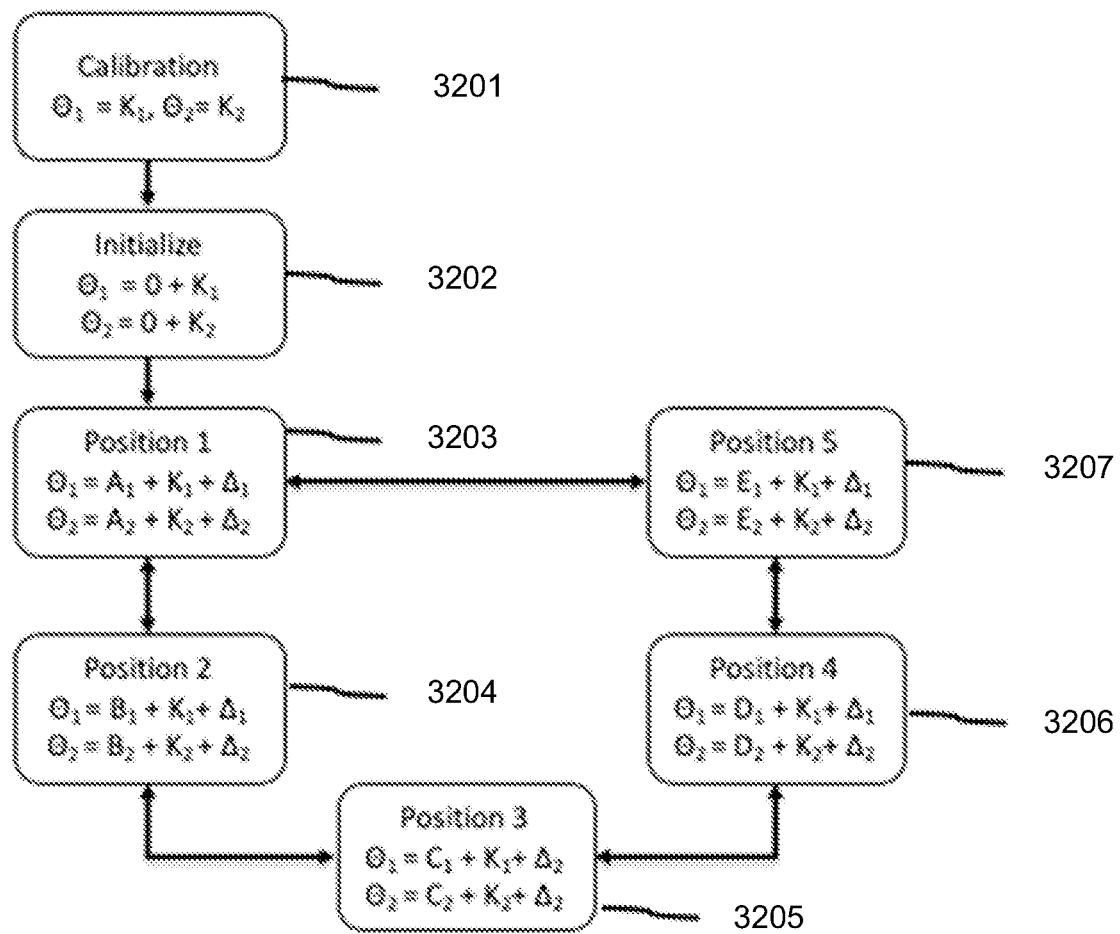
FIG. 32 is a flowchart illustrating the process of calibrating, initializing and positioning the robot's arms in the correct orientation matching the internal geometries of the prosthesis in accordance with one embodiment.
Figure 33:
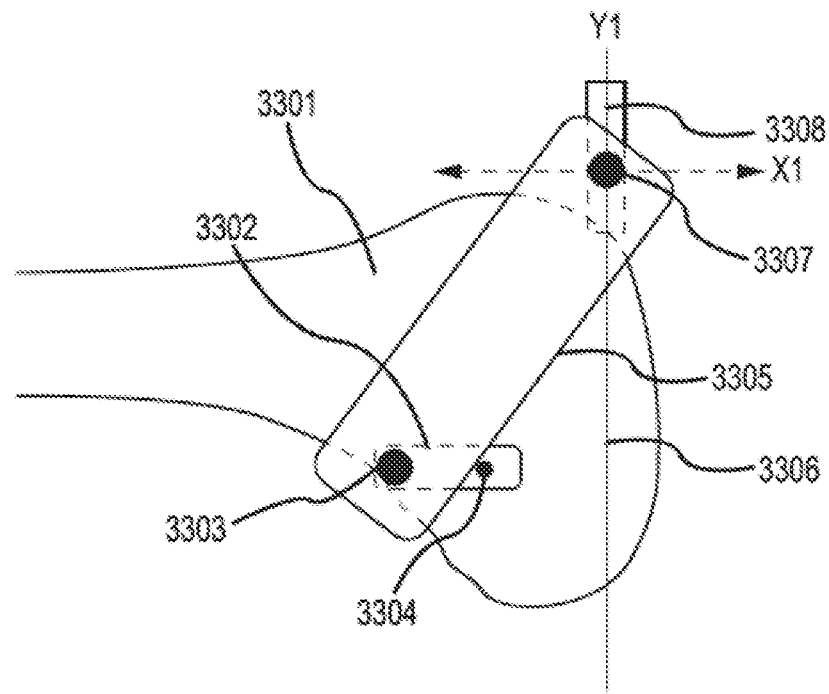
FIG. 33 is a perspective illustration of the robot's arm configuration in the 1st position matching the internal geometry of the femoral component for distal bone resection in accordance with one embodiment.
Figure 34:
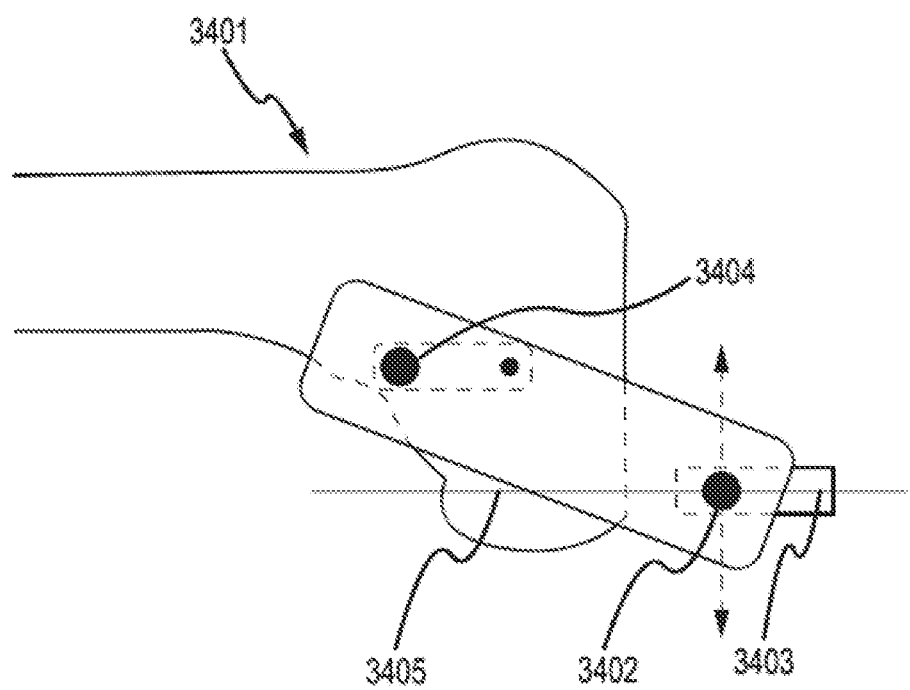
FIG. 34 is a perspective illustration of the robot's arm configuration in the 2nd position matching the internal geometry of the femoral component for posterior bone resection in accordance with one embodiment.
Figure 35:
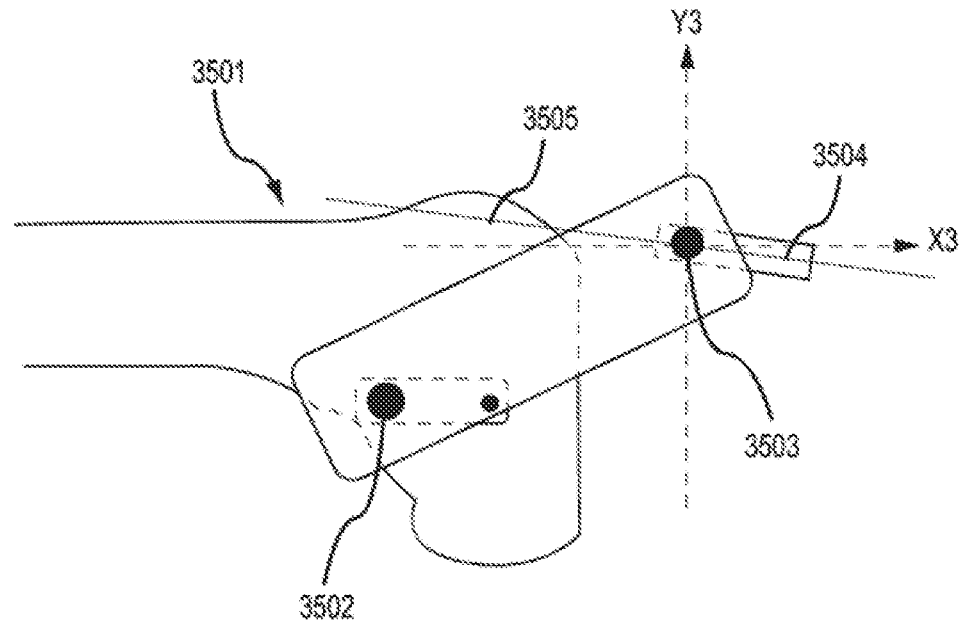
FIG. 35 is a perspective illustration of the robot's arm configuration in the 3rd position matching the internal geometry of the femoral component for anterior bone resection in accordance with one embodiment.
Figure 36:
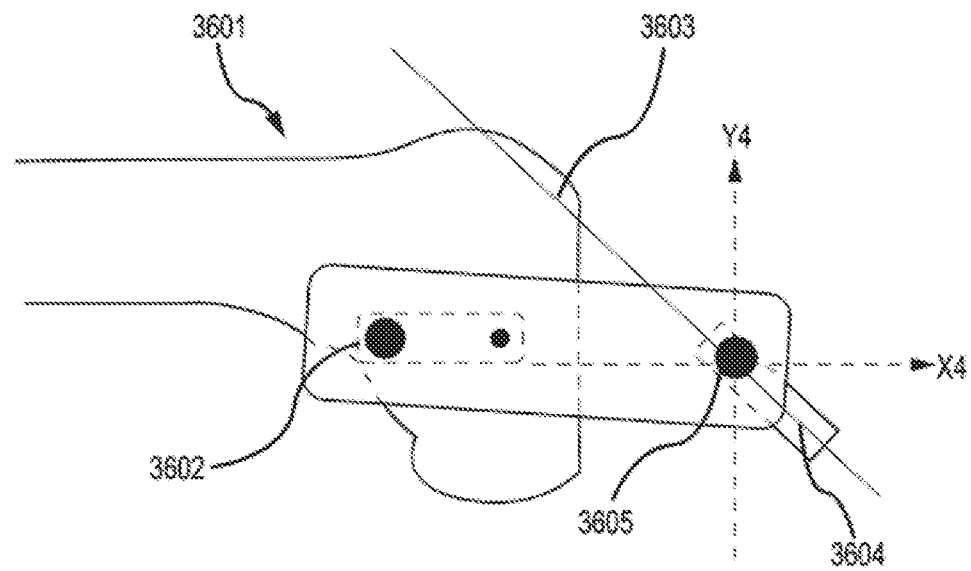
FIG. 36 is a perspective illustration of the robot's arm configuration in the 4th position matching the internal geometry of the femoral component for anterior chamfer resection in accordance with one embodiment.
Figure 37:
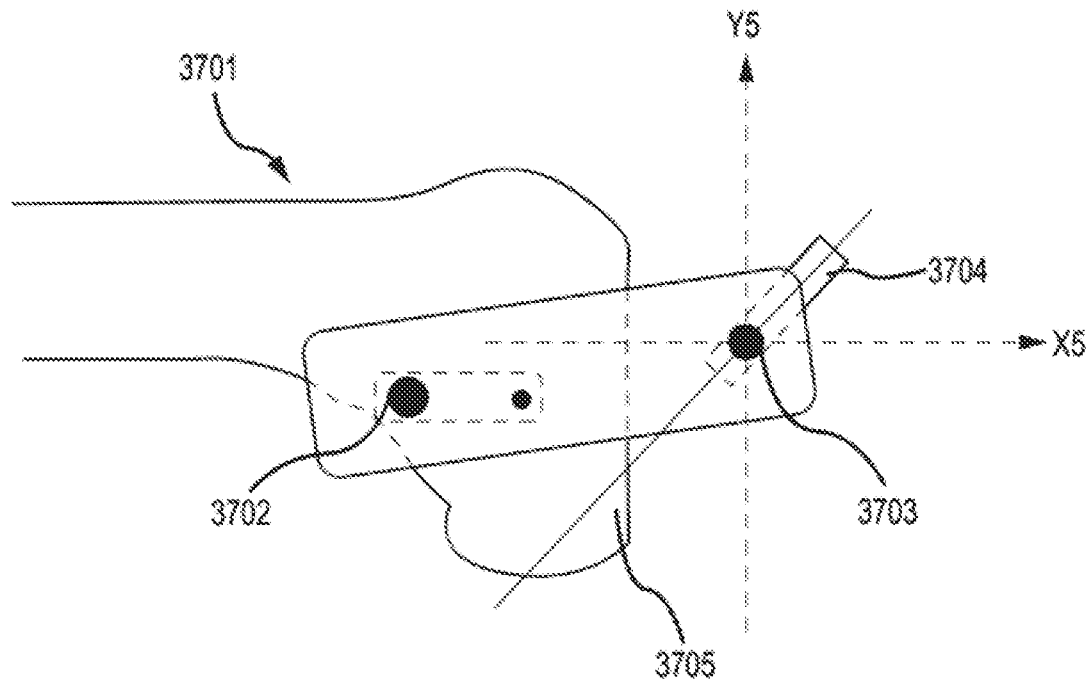
FIG. 37 is a perspective illustration of the robot's arm configuration in the 5th position matching the internal geometry of the femoral component for posterior chamfer resection in accordance with one embodiment.

FIG. 32 is a flowchart illustrating the process of calibrating, initializing and positioning the robot's arms in the correct orientation matching the internal geometries of the prosthesis. Beginning with calibration in 3201, the robot's rotational joints $\theta_1$ and $\theta_2$ are adjusted by adding or subtracting an angular or implant offset ($K_1$ and $K_2$) for each joint such that 0 Degree is defined by the end-effector position ($L_1$, 0) of FIG. 31. Calibration is normally done prior to the surgical procedure to verify the accuracy of the robot using a fixture and sensors, such as high-resolution encoders, that can accurately measure the end-effector angular position. The offsets are then stored in the robot's non-volatile memory. During the procedure, the initialization operation 3202 validates the robot has been mounted to the bone correctly and no angular changes have taken place before cutting or drilling the bone. In operation 3203, the robot moves to position 1 including the arm angle $\Delta_1$ based on the look up table of the implant internal geometry plus calibration offset $K_1$ plus any adjustments $\Delta_1$ in terms of (X or Y adjustments made by the surgeon) and cutting guide angle $\Delta_2$ based on the look up table of the implant internal geometry plus calibration offset $K_2$ plus any adjustments 42 in terms of (X or Y adjustments made by the surgeon). Similarly in operations 3204, 3205, 3206 and 3207 the robot moves to each position with corresponding angles for link 1 and cutting guide plus calibration offsets for each rotational joint plus and (X,Y) adjustments made by the surgeon.

In FIGS. 33-37, perspective illustrations of the robot's arm configuration for all five positions matching the internal geometry of the femoral component are shown. For distal bone resection of the femur 3301 shown in FIG. 33, the one link robot with two rotational joint 3305 is mounted on the medial condyle using two fixation pins 3303 and 3304 positioned by the customized registration guide in FIG. 22. An oscillating saw blade is inserted into the cutting guide 3308 to osteomize the distal bone 3306 along the Y-axis. Linear adjustments along the X-axis while maintaining the cutting angle is possible by recalculating the end-effector position ($X_1,Y_1$) where the cutting line 3308 intersects with the robot workspace in FIG. 31. For posterior resection of the femur 3401 shown in FIG. 34, the robot is mounted to the bone using two fixation pins at location 3404 positioned by the customized registration guide in FIG. 22 in any location suitable location on the femur. An oscillating saw blade is inserted into the cutting guide to osteomize the posterior bone 3405 along the X-axis. Linear adjustments along the Y-axis while maintaining the cutting angle is possible by recalculating the end-effector position ($X_2,Y_2$) where the cutting line 3403 intersects with the robot workspace in FIG. 31. For anterior resection of the femur 3501 shown in FIG. 35, the robot is mounted to the bone using two fixation pins at location 3502 positioned by the customized registration guide in FIG. 22. An oscillating saw blade is inserted into the cutting guide to osteomize the anterior bone 3505 along the X-Y axes. Linear adjustments along the X-Y axes while maintaining the cutting angle is possible by recalculating the end-effector position ($X_3,Y_3$) where the cutting line 3504 intersects with the robot workspace in FIG. 31. For anterior chamfer of the femur 3601 shown in FIG. 36, the robot is mounted to the bone using two fixation pins at location 3602 positioned by the customized registration guide in FIG. 22. An oscillating saw blade is inserted into the cutting guide to osteomize the anterior chamfer bone 3603 along the X-Y axes. Linear adjustments along the X-Y axes while maintaining the cutting angle is possible by recalculating the end-effector position ($X_4,Y_4$) where the cutting line 3604 intersects with the robot workspace in FIG. 31. Finally, for posterior chamfer of the femur 3701 shown in FIG. 37, the robot is mounted to the bone using two fixation pins at location 3702 positioned by the customized registration guide in FIG. 22. An oscillating saw blade is inserted into the cutting guide to osteomize the posterior chamfer bone 3705 along the X-Y axes. Linear adjustments along the X-Y axes while maintaining the cutting angle is possible by recalculating the end-effector position ($X_4,Y_4$) where the cutting line 3704 intersects with the robot workspace in FIG. 31.

Figure 38:
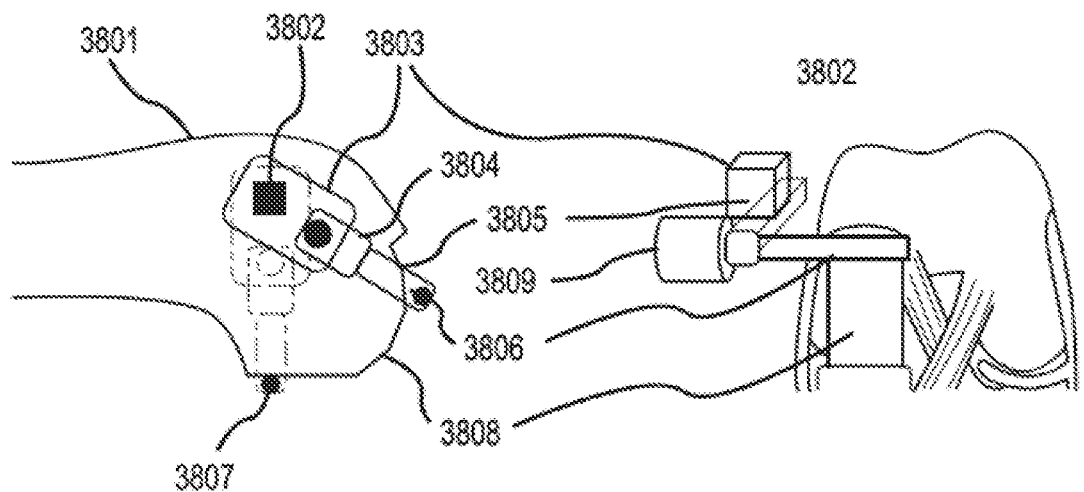
FIG. 38 are perspective illustrations of the robot's arm configuration matching the internal geometry of the uni femoral component for bone resurfacing in accordance with one embodiment.

FIG. 38 are perspective illustrations of the robot's arm includes rotational joint 3803 and variable linear actuator 3804 following the path of the internal geometry of the uni femoral component 3808 for bone resurfacing. The 2-DOF robot is mounted to the medial condyle of the femur 3801 with the workspace accommodating the implant using one or more square fixation pin at location 3802 positioned by the customized registration guide in FIG. 22. A milling tool 3806 attached an electric motor 3809 to the end-effector 3806 follows the implant internal geometries 3807-3808. The end-effector (X,Y) positions can be used to calculate the inverse kinematic equation of the robot described in FIG. 24. Forward kinematics equation can be used to calculate the end-effector position with respect to the X-Y axes. The milling tool with a certain diameter is factored into the calculation of the end-effector position in removing the correct amount of bone.

Aspects of the present disclosure involve methods and systems for a small robotic-assisted surgical systems mounted to the patient's anatomy. To aid in the description below, a brief discussion of static and dynamic soft tissue gap balancing during the procedure is now included. As mentioned above, the present disclosure may be applied to any region of a patient's joint as part of the orthopedic procedure. However, for ease of understanding, the discussion herein is limited to particulars of the knee as an example of the inventions relating to the present disclosure procedure and embodiments.

Figure 39:
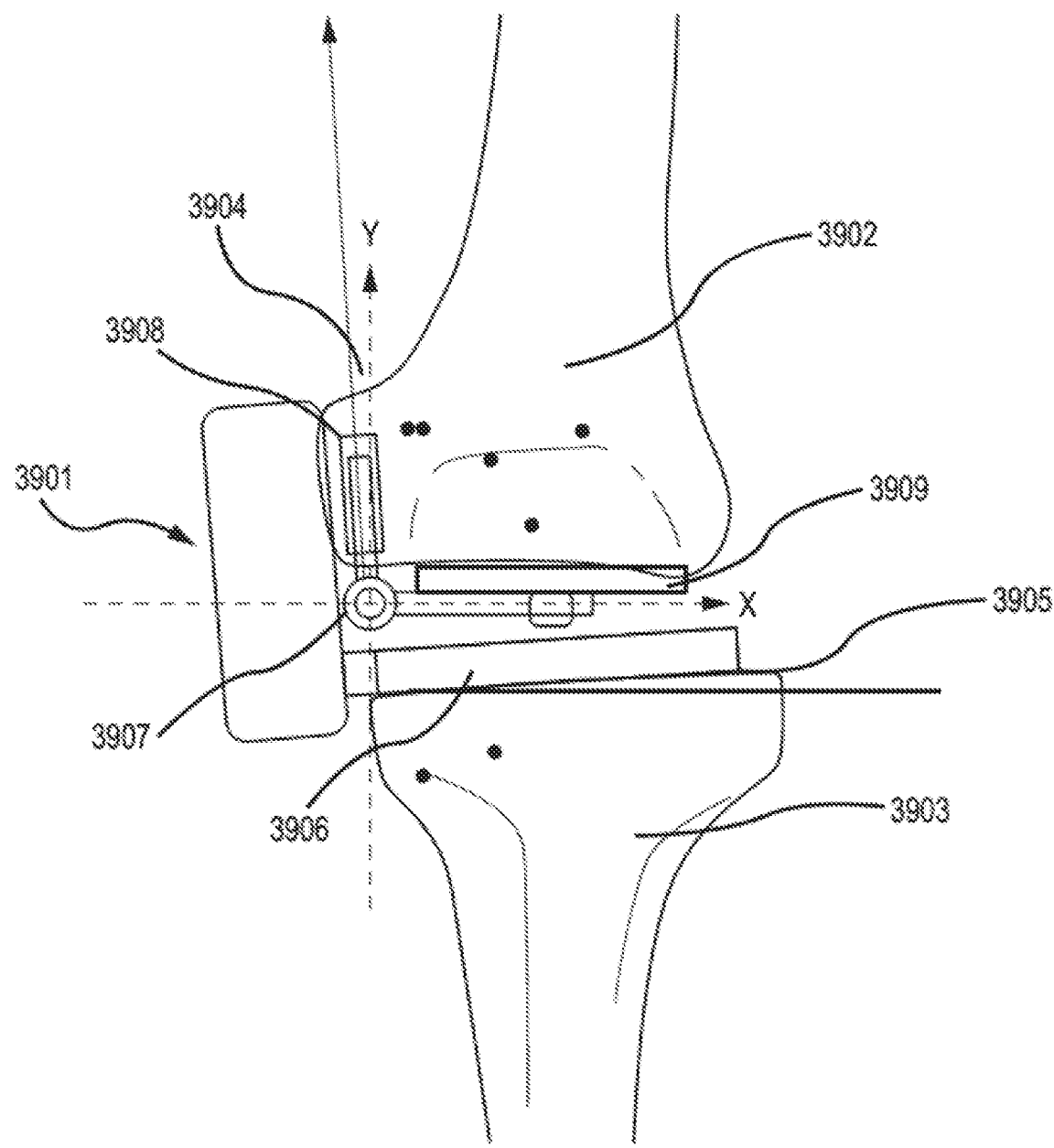
FIG. 39 is illustrating an example of an intra-operative soft-tissue ligament balancing where the knee extension gap is asymmetric using a 5-DOF robot to determine the tension (force) of the ligaments and angular correction in accordance with one embodiment.

FIG. 39 is illustrating an example of soft-tissue balancing of the knee joint gap in extension using a 5-DOF robot 3901 to tension (force) the ligaments and correct varus/valgus angle if needed. In order to achieve ligament balance in extension, the bone gap created by the distal femur and proximal tibial resections should be rectangular to match the corresponding distal femoral and proximal tibial implant internal geometries and thickness. When the gap is asymmetric, the knee is not balanced when load or weight is applied to the knee joint when standing, causing tightness or looseness to the MCL or LCL depending on which side of the ligaments are longer and shorter. Two rectangular fixtures are mounted to the distal femur 3902 and proximal tibia 3903. The fixture 3909 mounted to the distal femur is described in FIG. 27. The plate 3906 pushed against the proximal tibia can be a rectangular cutting guide or spacer block. To measure the gap in extension and balance the ligaments, the knee is placed in full-extension while the linear actuator or piston 3908 is keeping the ligaments tensioned with a certain force. Once the ligaments are tensioned, the hinge 3907 is allowed to rotate. If the gap is symmetric, the hinge 3907 will be approximately 90 Degrees relative to (X,Y) axes. Any asymmetric gap or angle 3904, can be visually inspected or measured with a sensor or protractor to determine the exact angle. In one embodiment, the desired extension gap is asymmetric to correct any deformities in the overall leg alignment. To correct the asymmetric gap, the corresponding varus/valgus 3905 on the tibia is resected to balance the gap.

Figure 40:
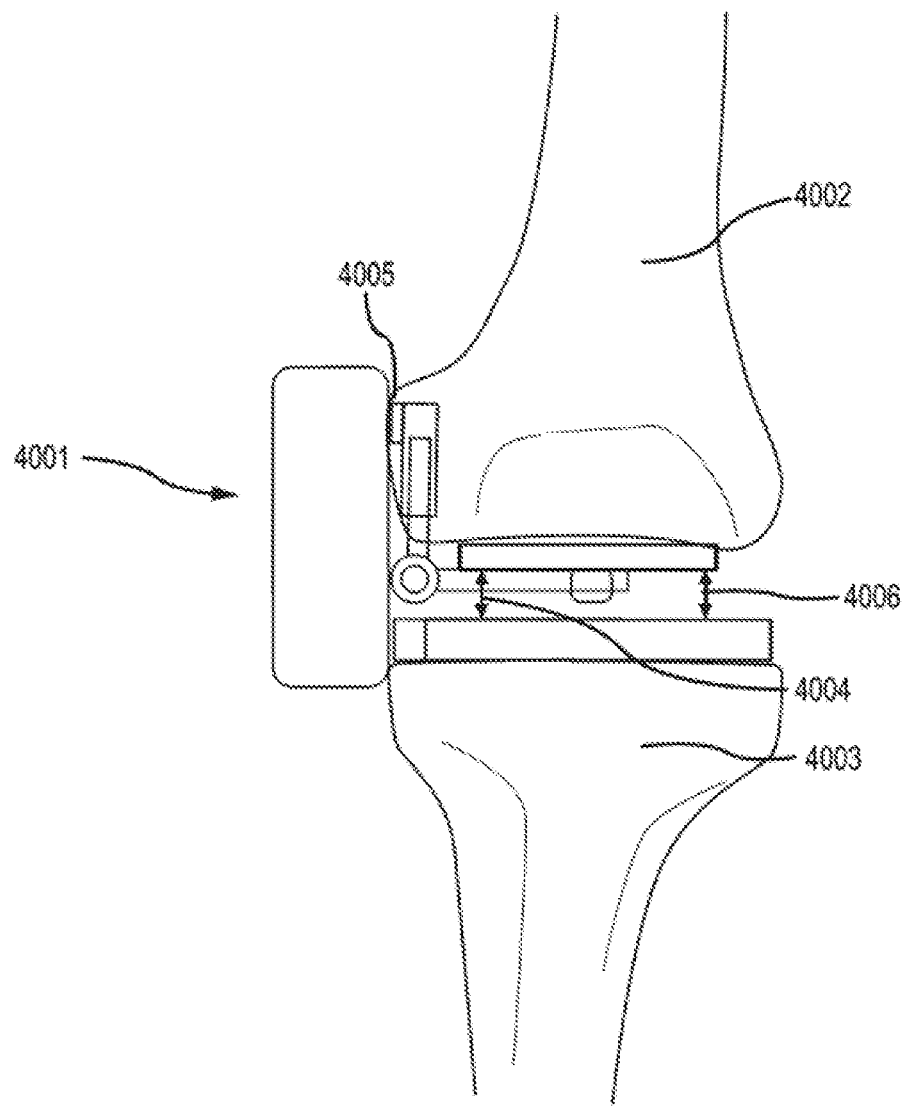
FIG. 40 is illustrating an example of an intra-operative soft-tissue ligament balancing where the knee extension gap is asymmetric using a 5-DOF robot to determine the tension (force) of the ligaments and angular correction in accordance with one embodiment.

FIG. 40 is illustrating an example of balanced joint gap and soft-tissue ligaments using a 5-DOF robot 4001 to determine the tension (force) 4005 of the ligaments in extension. The extension gap of the distal femur 4002 and proximal tibia 4003 are balanced both on the medial and lateral side 4004. In one embodiment, the linear actuator, spring piston, or linear position sensor 4005 measures the gap distance in millimeters. If the gap is not sufficient to accommodate the thickness of the prosthesis (metal and plastic), a parallel re-cut is performed on either the distal femur 4002 or proximal tibia 4003. In one embodiment, the soft tissues are balanced regardless of the symmetry of the gap to accommodate different implant designs. In another embodiment, the soft-tissue or gap is balanced based on a desired ligament tension or medial and lateral stability of the knee.

Figure 41:
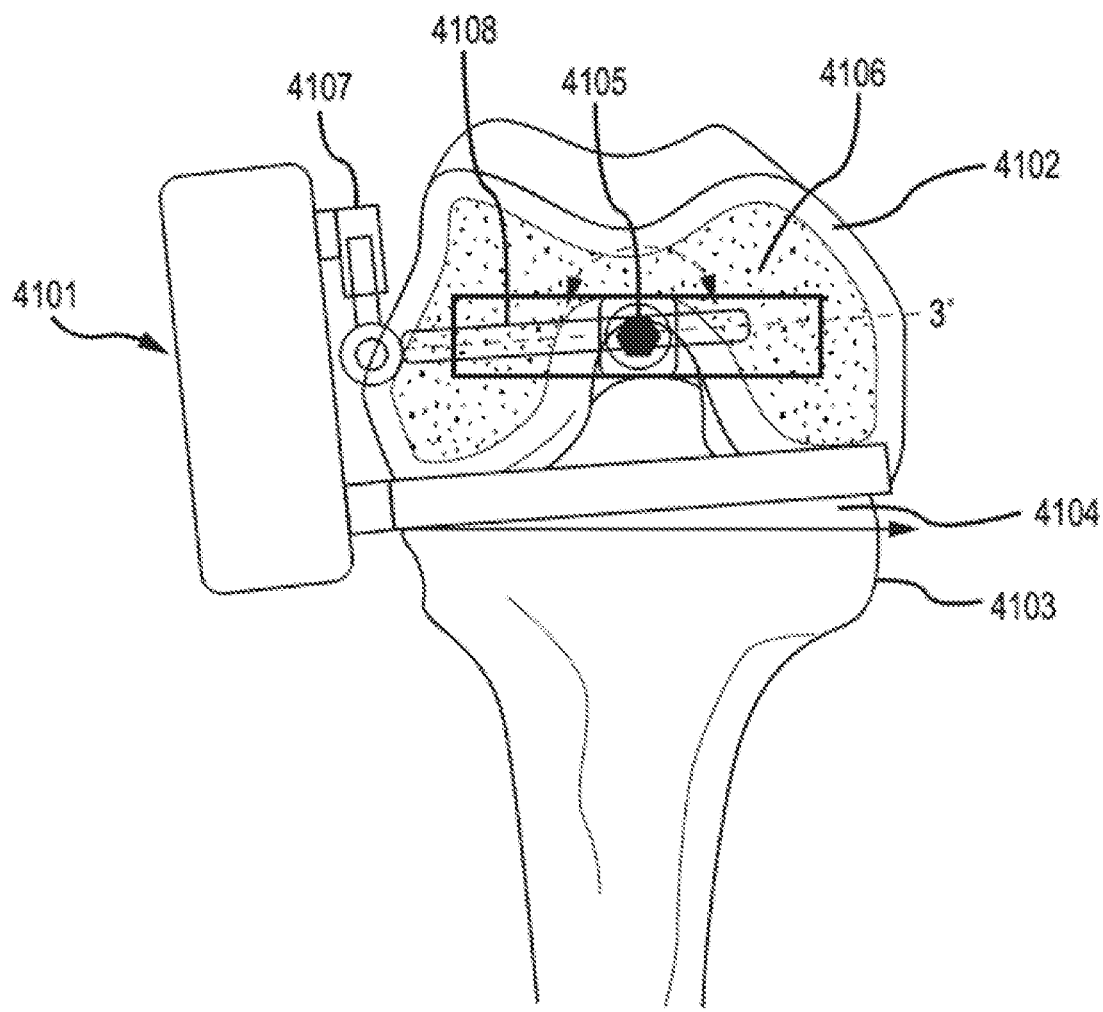
FIG. 41 is illustrating an example of an intra-operative soft-tissue ligament balancing where the knee flexion gap is asymmetric using a 5-DOF robot to determine the tension (force) of the ligaments and angular correction in accordance with one embodiment.

FIG. 41 is illustrating an example of balancing the soft-tissue (knee joint gap) using a 5-DOF robot to determine the tension (force) of the ligaments and rotation angle in flexion. Similar to FIG. 39, the tibia 4103 is flexed approximately 90 Degrees with respect to the femur 4102. In one embodiment, the goal is to create a symmetric gap on the medial and lateral posterior condyles. In another embodiment, the goal is to create an asymmetric gap depending on the amount of ligament tension of the MCL or LCL or rotational stability of the knee. In another embodiment, the medial and lateral posterior condyles are tensioned independently using a spreader instead of paddles. The fixture of 3909 is mounted to the distal femur 4106 and cutting guide or spacer block 3906 is pushed against the proximal tibia by the linear actuator or spring piston 4107. The locking mechanism 4105 is loosened while the hinge 3907 is fixed at 90 Degrees to allow the knee to rotate (internal/external) when force is applied to tension the ligaments. In one embodiment, the hinge 3907 is loosened instead and the bar 4108 of the locking mechanism 4105 is fixed at 0 Degrees to allow the knee to rotate under tension. The rotation angle can be determined visually similar to a protractor with markings on the locking mechanism 4105 or hinge 3907. In one embodiment, the hinge or locking mechanism includes a sensor to measure the rotational angle. The corresponding angle of 4104 can then be used to correct the varus/valgus angle of the tibia or posterior condyles of the femur to create a desired soft-tissue balance or flexion gap.

Figure 42A:
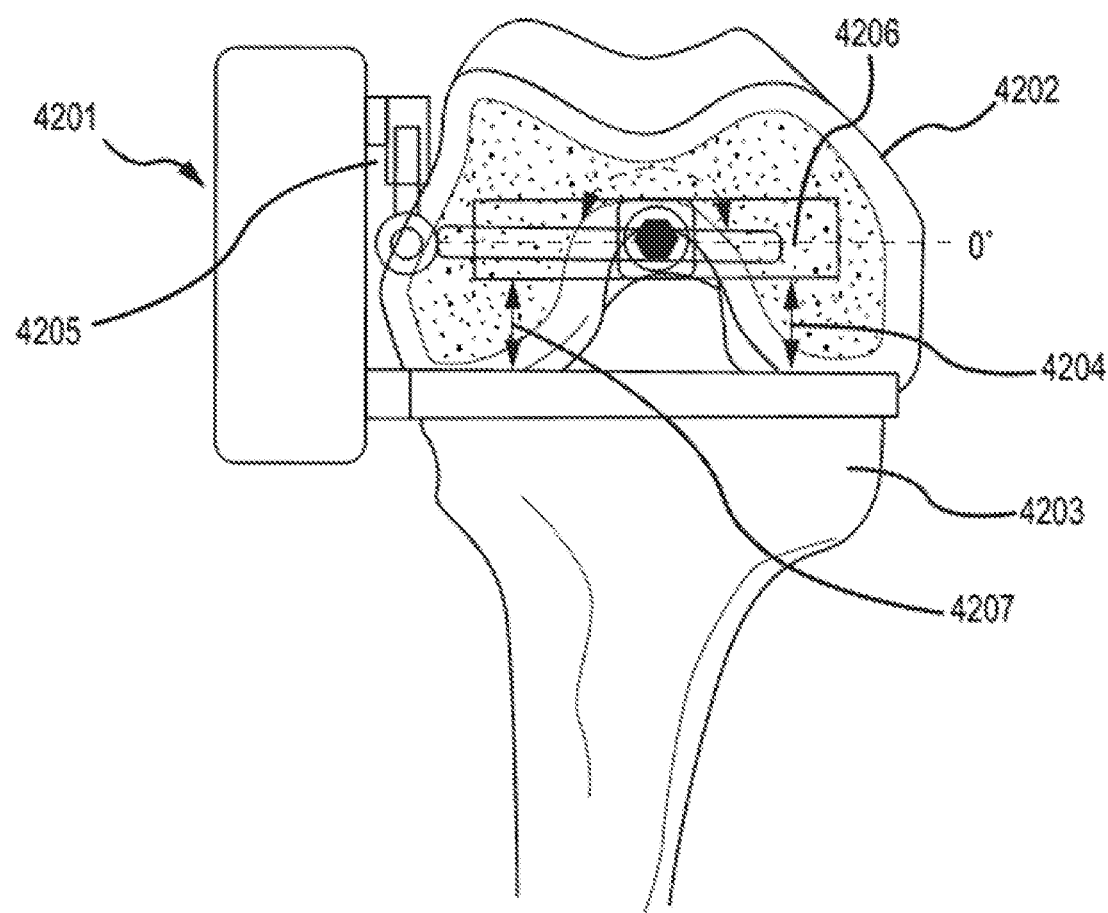
FIG. 42A is illustrating an example of an intra-operative soft-tissue ligament balancing where the knee extension gap can be symmetric using a 6-DOF robot to determine the tension (force) of the ligaments and angular correction in accordance with one embodiment.

FIG. 42A is illustrating an example of a balanced knee using a 5-DOF robot to determine the tension (force) of the ligaments in flexion. The flexion gap of the distal femur 4202 and proximal tibia 4203 are balanced both on the medial and lateral side 4204. In one embodiment, the linear actuator, spring piston, or linear position sensor 4205 measures the gap distance in millimeters. If the gap is not sufficient to accommodate the thickness of the prosthesis, a parallel re-cut is performed on either the distal femur 4202 or proximal tibia 4203. In one embodiment, the soft-tissue is balanced regardless of the symmetry of the gap to accommodate different implant designs such as custom or asymmetric tibial platforms. In another embodiment, the soft-tissue or gap is balanced based on a desired ligament tension or stability of the knee.

FIGS. 42B-42C is another embodiment of a knee joint flexion gap balancing using a 3-DOF robot 4201 and a mechanical scissor jack 4220. As described above in FIG. 41, the linear actuator or spring piston 4107 is replaced by a simple bar/arm 4224 that connects to the locking mechanism 4105. The scissor jack device 4220 consists of a center screw with opposite threads 4226 and 4-bar rotating hinge 4221 is attached to the 2-DOF robot's end-effector joint. Attached to the bottom of 4221 is a metal plate 4227 that is approximately the same width and height as the tibia 4203 to distribute the force equally on the entire surface of the proximal tibia. When the end-effector of the 2-DOF robot 4201 rotates clockwise or counter-clockwise, the 4-bar linkage 4221 can contracts or expands as shown in 4224 thus raising or lowering the metal plate 4227. As discussed above, the goal of the knee joint gap balancing is to create a rectangular flexion gap. This is accomplished when the bar/arm 4225 is approximately parallel to the plate 4227 and proximal tibial cut plane 4228. The surgeon can manually rotate the tibia 4203 in varus/valgus orientation to determine if the MCL and LCL are tensioned correctly. The height of or spacing between the plate 4223 can be adjusted by the 2-DOF robot until the desired tension is achieved.

Figure 42D:
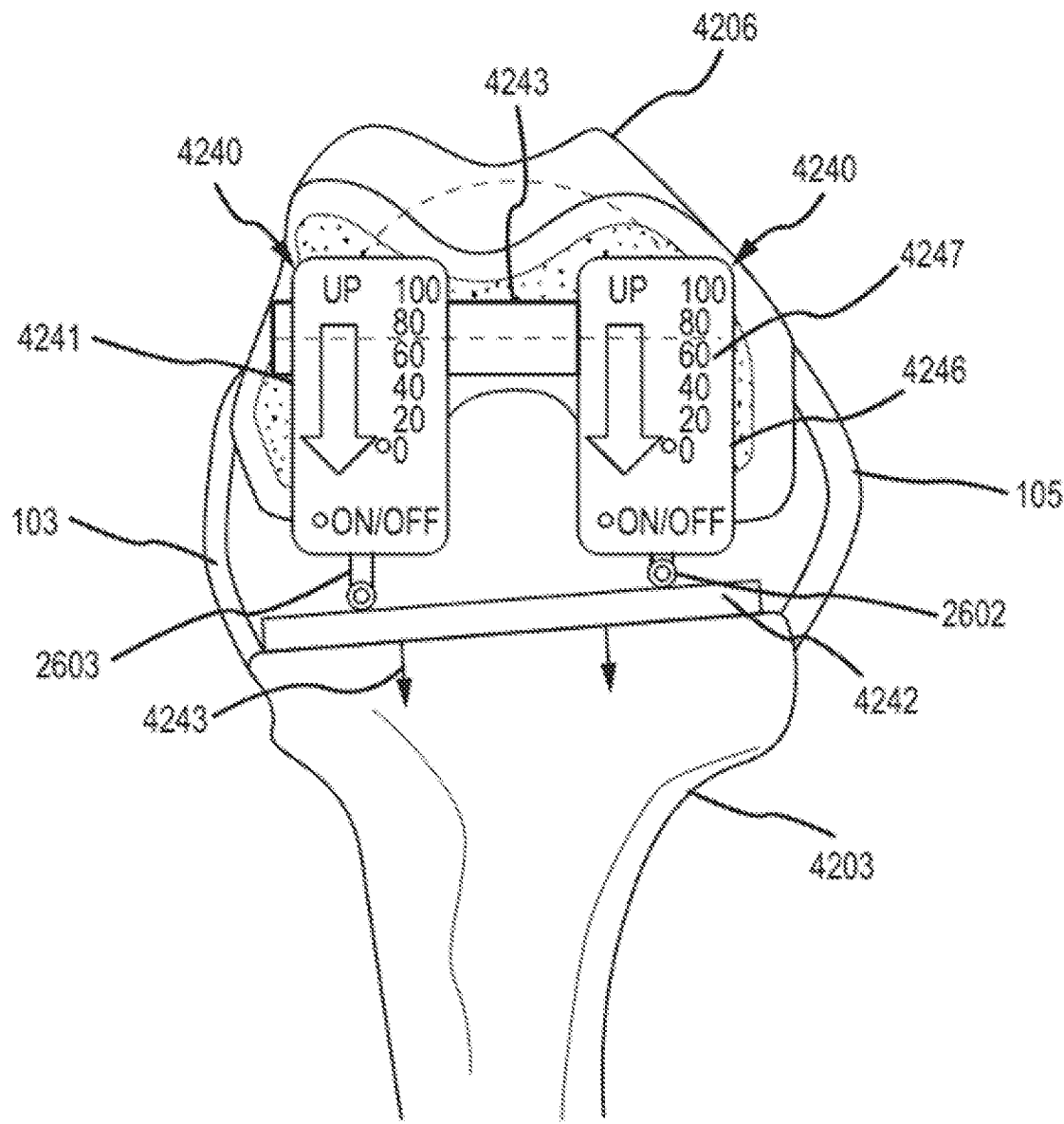

FIG. 42D is another embodiment of knee flexion gap balancing using two 2-DOF robots 4240. The 2-DOF robot 4240 is similar to the uni-knee 2-DOF robot described in FIG. 26 except for the display shown in 2620. The display of 4240 consists of an arrow 4241 pointing in the direction of the linear actuator 2603 pushing against the metal plate 4242 attached to the proximal tibia 4203 using two or more spikes 4243. The spikes prevent the tibia plate from sliding when force is applied through the linear actuators of the robots. In addition, the display consists of force and/or torque measurements within a certain range indicated by an LED 4246 or displayed by an LCDs. At the end of the linear actuator is a ball like instrument attached to the end-effector 2602. The shape of the ball (round) allows the 2-DOF robots to rotate about their respective base joints, which are attached to the distal femur 4206 through the plate 4243 described in FIG. 27. The 2-DOF robots 4240 can operate independently, coordinate with each other via wired or wireless communication or communicate bi-directionally with a computer device.

Figure 42E:
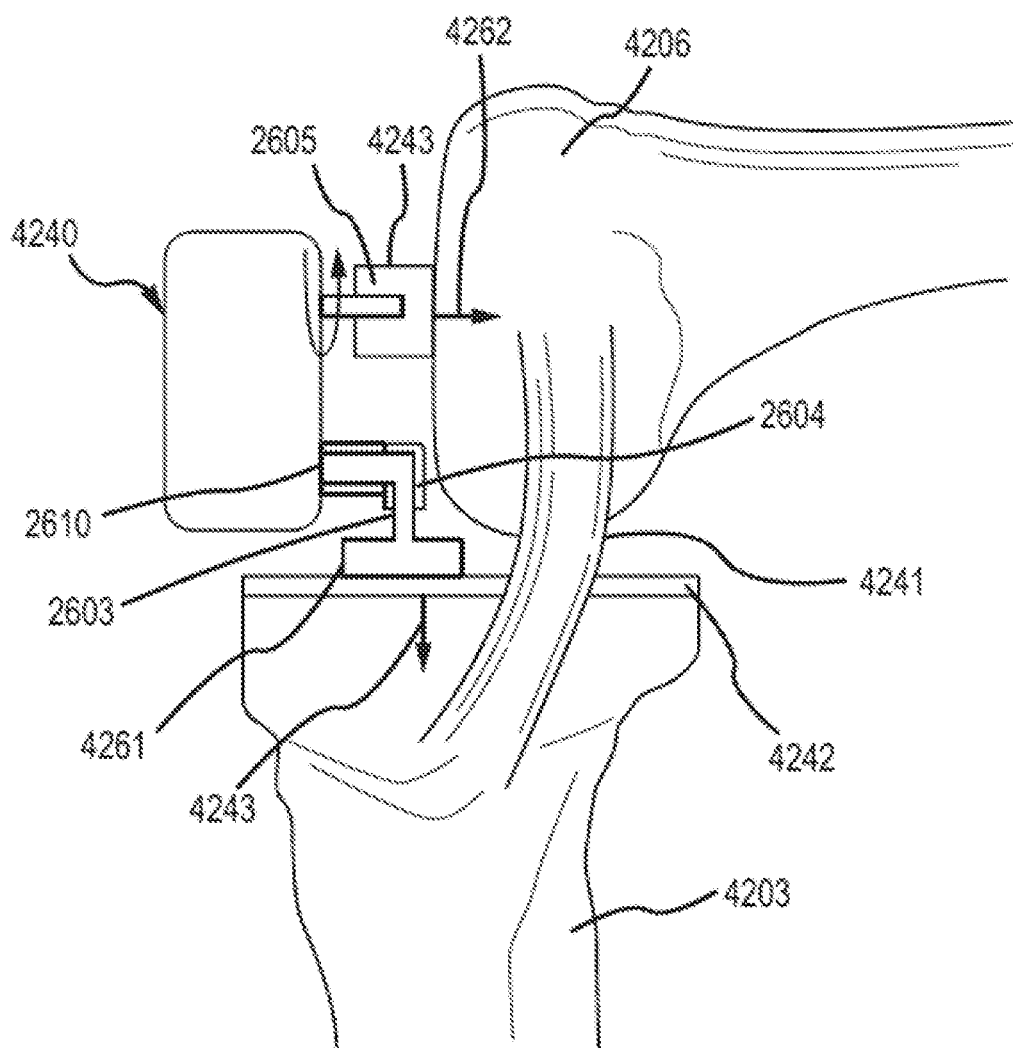

FIG. 42E is a side view of the 2-DOF robot 4240 shown in FIG. 42C with the knee flexed at approximately 90 Degrees. As described above the base rotation joint 2605 of the robot 4240 is attached to the plate 4243 and secured in place by one or more spikes 4262 embedded inside the cancellous bone of the femur 4206. Similarly, the linear actuator of the robot 4240 attached to the rotating joint 2610 consists of a 90 Degree gear box 2640 and a linear actuation arm 2603 is pushing down on the base plate 4242 attached to the proximal tibia 4203 using one or more spikes 4243. In another embodiment, the ball like instrument attached to the end-effector is a feet, skid or paddle for stability. In another embodiment, the ball like instrument is a force sensor measuring the tension of the MCL 4241.

Figure 42F:
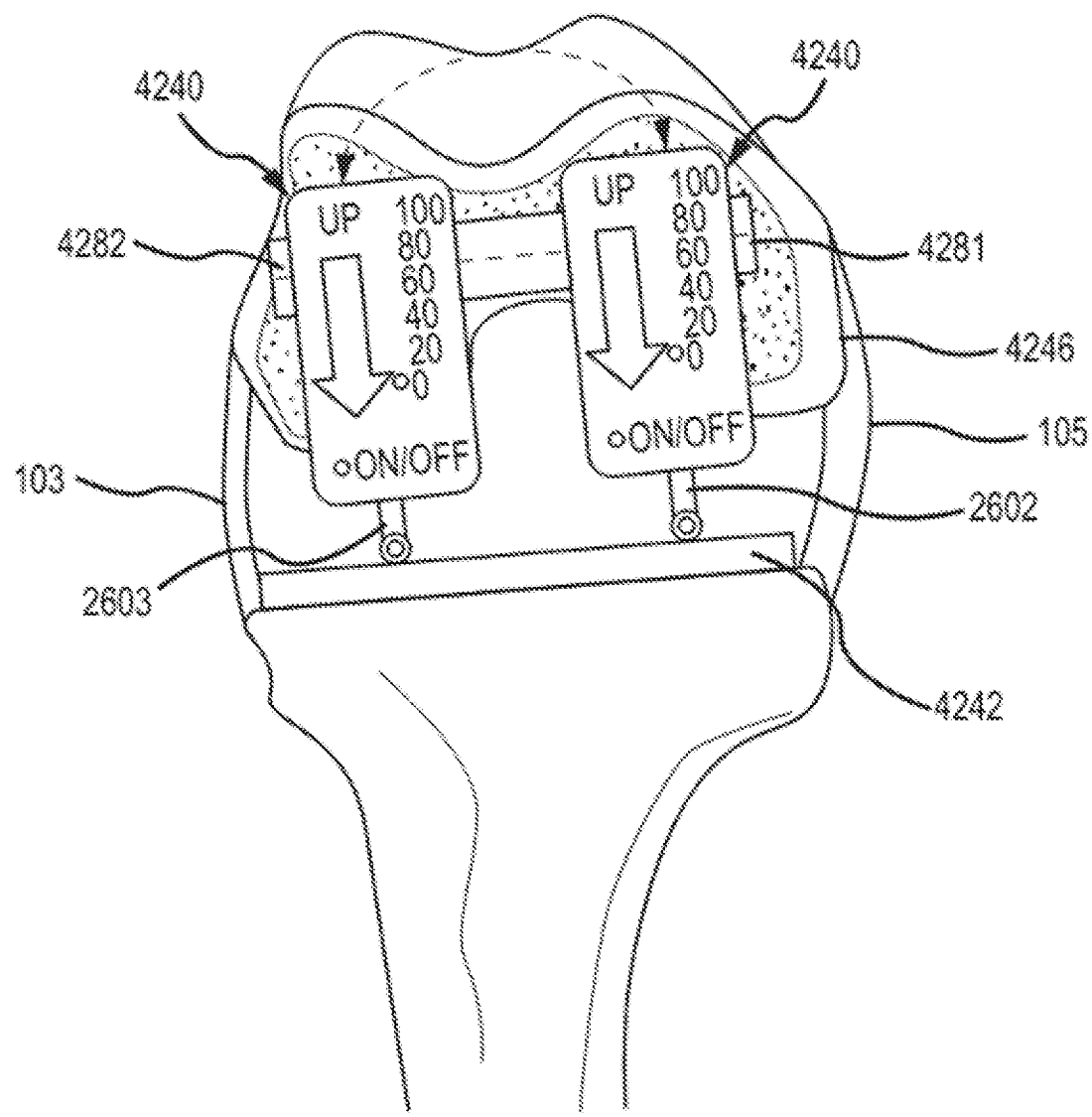

As described above, the goal of knee joint gap balancing is to achieve a rectangular flexion gap. In many instances, it is desirable to have different ligament tensions for the medial and lateral compartments to mimic the human knee or the design of the protheses are such that an asymmetric flexion gap is required. In addition, the tensions of MCL 105 and LCL 103 for the male and female knees are different, therefore it's desirable to customize the ligament tensions for each individual patient and implant design. For ease of demonstration, FIG. 42F illustrates a balanced medial and lateral ligament tensions of 60 Newton's as shown by the LED display 4281 and 4282. Note the desired tension (force) can be pre-programmed in each individual robot 4240 before the procedure or transmitted to the robots wirelessly during the procedure. In addition, the knee compartments (medial and lateral) are balanced when the torque measurements of the base rotating joint of each robot is 0 Newton-meter or some desired torque value and the linear actuators of each robot 4240, respectively 2602 and 2603, is approximately 90 Degrees relative to the tibial base plate 4242. For asymmetric flexion gap, the ligament tension for each compartment can be achieved since each 2-DOF robot can actuate and rotate about the base independently. Once the desired tension (force and/or torque) is achieved, the position of the rotating base joint in Degrees is measured by the encoders attached to the individual motors. The difference in the base joint angles of the medial and lateral robot can then be used to adjust the IR/ER of any of the cutting guide robots in FIGS. 29A-29B, 30 or conventional 4-in-1 cutting block.

Figure 43:
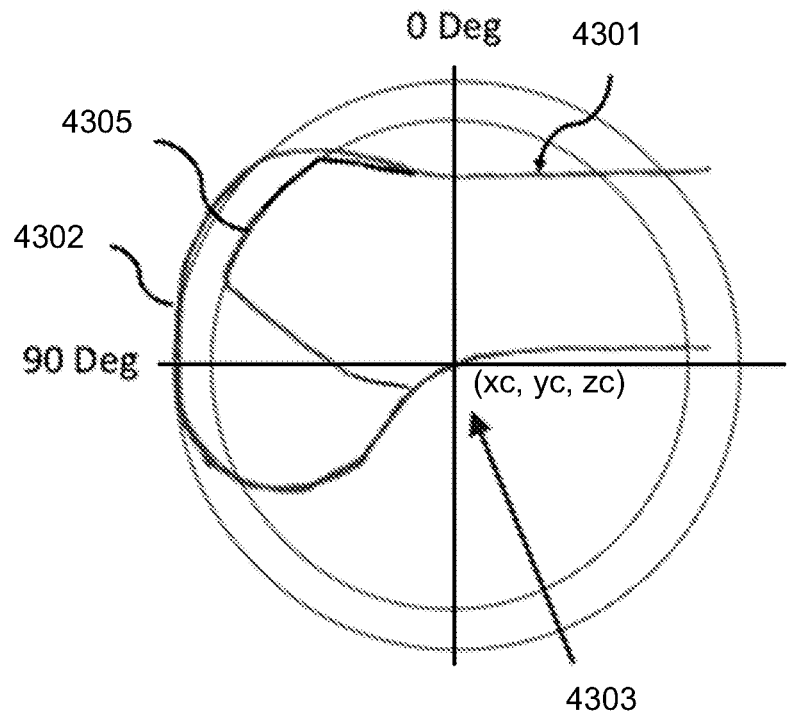
FIG. 43 is a perspective illustration of a knee with single axis of rotation for dynamic soft-tissue ligament balancing in accordance with one embodiment.

FIG. 43 is a perspective illustration of a femur 4301 with a single axis of rotation 4303 defined by the center of rotation of the medial condyle, lateral condyle (overlaps with medial condyle from ~0 to 30 Degrees) (collectively 4302) and patella groove 4305. As described earlier in FIGS. 39-42, the soft-tissue ligament gap is balanced approximately at 0 Degrees (extension) and 90 Degrees (flexion). In order to measure the ligament tension kinematically from 0 to 90 Degrees, a single axis is defined such that a robot described in FIGS. 23 and 24 can measure the ligament tension using a force sensor and the measurement can be transmitted to the computer. The sensor data collected can be used to determine the normal kinematic motion of the patient's knee by comparing to pre-operative simulation, predict clinical outcomes using predictive analytics of post-operative data or compare the performance of different implant brands or sizes.

Aspects of the present disclosure involve methods and systems for a small robotic-assisted surgical systems mounted to the patient's anatomy. To aid in the description below, a brief discussion of a computer system in the operating room for real-time data and communication is now included. As mentioned above, the present disclosure may be applied to any region of a patient's joint as part of the orthopedic procedure. However, for ease of understanding, the discussion herein is limited to particulars of the knee as an example of the inventions relating to the present disclosure procedure and embodiments.

Figure 44:
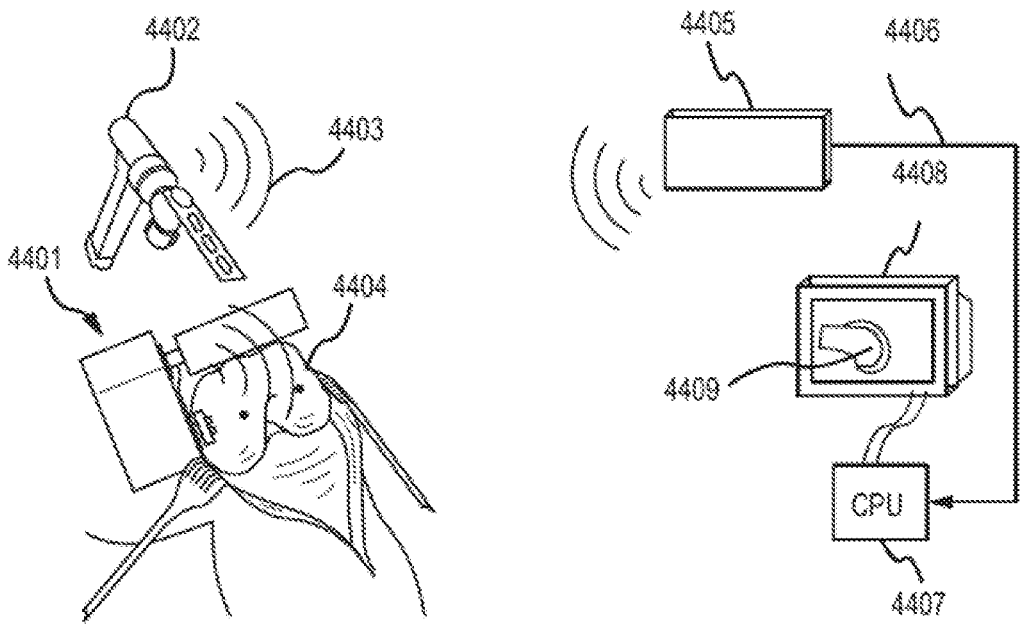
FIG. 44 is a perspective illustration a robotic-assisted surgical system in the operating room displaying real-time information using a computer system and two-way communication in accordance with one embodiment.

FIG. 44 is a perspective illustration of a robotic-assisted surgical system in the operating room. As the discussed previously in detail, using one of the registration methods, the robotic device 4401 may be mounted to the femur bone 4404. In one embodiment, the surgeon approves the surgical plan using pre-operative imaging before the surgical procedure and the implant brand, size and position have been finalized. In another embodiment, the implant brand, size and position are determined intra-operatively. The data is then transmitted using a transceiver 4405 connected to the computer 4407 through an interface 4406 to the robotic device, which can be configured to accommodate implant size and internal geometries. In one embodiment, the implant size and brand were determined before surgery and the implant data was downloaded to the robot using an USB cable. During the procedure, the computer system 4407 is tracking in real-time the surgical procedure and displaying sensor data or other critical information regarding the robot, such as battery life, temperature, current, torque or any error messages on the computer monitor 4408. In addition, commands, similar to the LCD or LED display in FIGS. 25 and 26, can be sent directly to the robot 4401 using the wireless or wired communication. In another embodiment, the final surgical plan is downloaded to the robot right before the surgical procedure using the internet. The computer system 4407, monitor 4408 and transceiver 4405 is not required, but provide additional real-time data. In addition, the wireless transceiver 4405 connected to the computer 4407 through the electrical interface 4406 can communicate with other surgical or robotic device in the form of cooperation or controlling another device remotely. For example, the oscillating saw 4402 is turned on when the saw is at the correct position and orientation.

Returning to the system 1400 of FIG. 14, several post-operative procedures may be performed on the results or data generated from the operation. For example, a procedure outcome dataset 1412 may be generated from information obtained from the robotic device and, in some instances, surgeon and patient feedback. Such information may be provided to a machine learning/data analysis system 1414. The machine learning system 1414 may receive such result datasets from multiple such procedures and, through one or more data analysis algorithms executed on the datasets, calculate a success/failure variable for any one operation or device of the system 1400 and method 1500. In some instances, one or more recommendations 1416 may be generated from the analysis system 1414 and provided during the pre-operative planning 1406 stage or the patient imaging 1402 stage to improve the clinical results of future arthroplasty procedures utilizing a customized registration guide.

Through the systems and processes described herein, a faster, cheaper, and more accurate robotic-assisted arthroplasty procedure may be performed utilizing a registration guide. In particular, a customized registration guide may be generated or created from a plurality of 2D images of a patient's anatomy. The registration guide may include one or more mating surfaces that mate with particular locations on the patient's bone of the damaged joint. Further, the generation of the registration guide may not require the approval of a surgical plan before being generated as the registration guide is based on the patient scans or images and does not include an indication of a resection plane or resurfacing information. During the arthroplasty procedure, the registration guide may be mated with the patient's bone, either by a surgeon or by the robotic device, and a location in three-dimensional space of the registration guide may be obtained for the robotic device. The robotic device may therefore determine the location of the patient anatomy without a registration process requiring a probe or a surgeon to locate particular locations on the patient's bone to provide the patient orientation to the robotic device. Rather, the registration device may attach to the robotic device and, because the dimensions of the registration device may be known, the location and orientation of the patient's anatomy may similarly be known. The location of the patient's anatomy may then be mapped to the surgical plan for resection and/or resurfacing by the robotic device.

Through the registration device, the use of optical locators in the arthroplasty procedure may be removed, thereby reducing the costs for performing the procedure to the patient and health-care facility. The registration device may also provide a more accurate registration procedure than previous registration procedures. Further, one or more movement sensors may be mounted on or otherwise associated with the patient's anatomy that wirelessly transmit patient movement to the robotic device for adjustments to the determined location/orientation of the cut plane in relation to the patient's bone. The use of movement sensors, such as one or more inertial sensors, may be more accurate than optical sensors for detecting the movement of the patient, further increasing the effectiveness of the arthroplasty procedure. The registration guide and inertial sensors may be utilized with any type of arthroplasty procedures, including procedures for knees, hips, shoulders, spine, etc. In some instances, virtual reality systems may be incorporated into the systems described to aid the surgeon in performing one or more aspects of the arthroplasty procedure. These and all other arthroplasty procedures may benefit through the systems and methods described herein.

Figure 45:
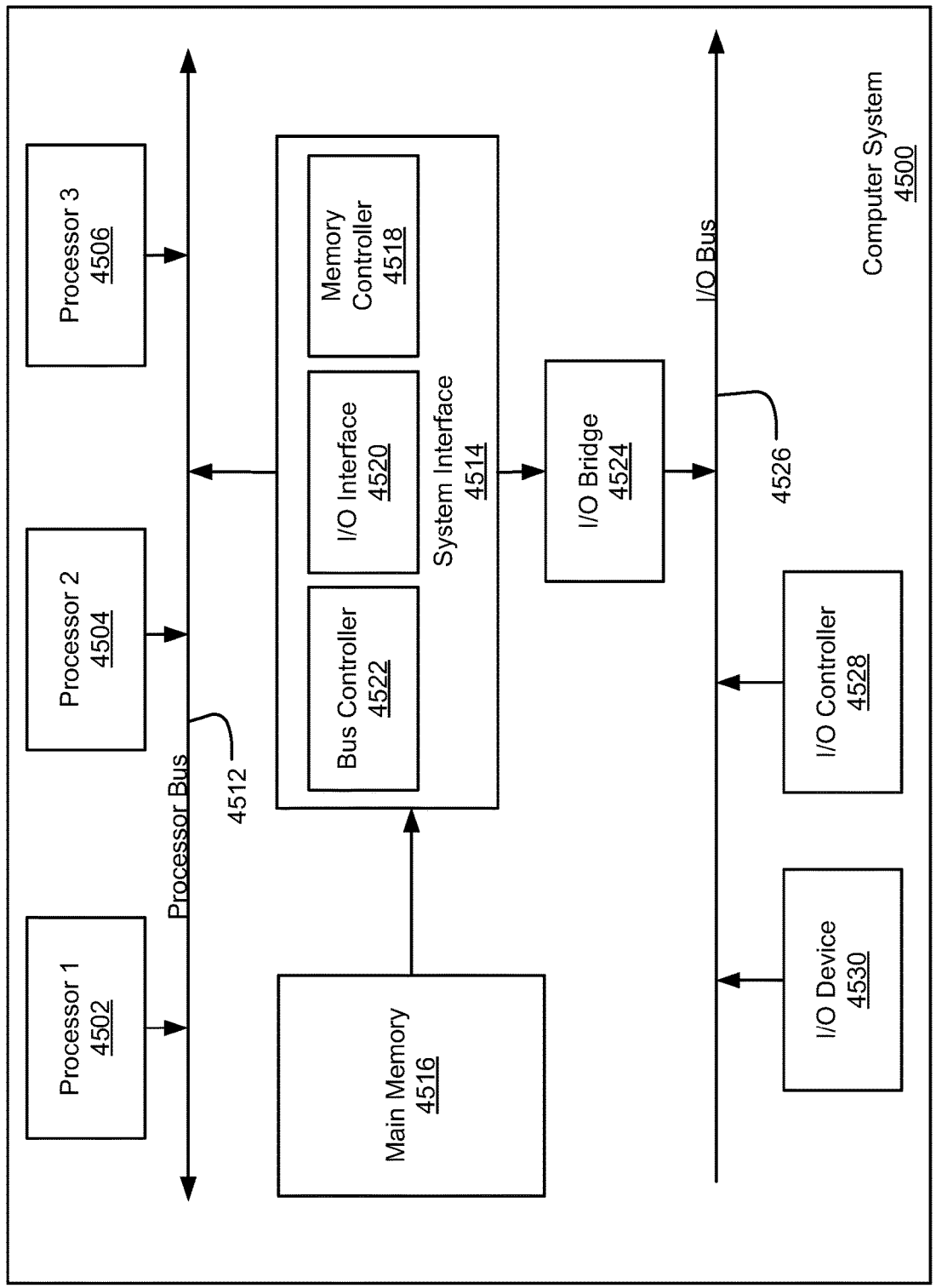
FIG. 45 is a diagram illustrating an example of a computing system which may be used in implementing embodiments of the present disclosure.

FIG. 45 is a block diagram illustrating an example of a computing device or computer system 4500 which may be used in implementing the embodiments of the components of the network disclosed above. For example, the computing system 4500 of FIG. 45 may be the robotic device discussed above is executed. The computer system (system) includes one or more processors 4502-4506. Processors 4502-4506 may include one or more internal levels of cache (not shown) and a bus controller or bus interface unit to direct interaction with the processor bus 4512. Processor bus 4512, also known as the host bus or the front side bus, may be used to couple the processors 4502-4506 with the system interface 4514. System interface 4514 may be connected to the processor bus 4512 to interface other components of the system 4500 with the processor bus 4512. For example, system interface 4514 may include a memory controller 4514 for interfacing a main memory 4516 with the processor bus 4512. The main memory 4516 typically includes one or more memory cards and a control circuit (not shown). System interface 4514 may also include an input/output (I/O) interface 4520 to interface one or more I/O bridges or I/O devices with the processor bus 4512. One or more I/O controllers and/or I/O devices may be connected with the I/O bus 4526, such as I/O controller 4528 and I/O device 4530, as illustrated.

I/O device 4530 may also include an input device (not shown), such as an alphanumeric input device, including alphanumeric and other keys for communicating information and/or command selections to the processors 4502-4506. Another type of user input device includes cursor control, such as a mouse, a trackball, or cursor direction keys for communicating direction information and command selections to the processors 4502-4506 and for controlling cursor movement on the display device.

System 4500 may include a dynamic storage device, referred to as main memory 4516, or a random access memory (RAM) or other computer-readable devices coupled to the processor bus 4512 for storing information and instructions to be executed by the processors 4502-4506. Main memory 4516 also may be used for storing temporary variables or other intermediate information during execution of instructions by the processors 4502-4506. System 4500 may include a read only memory (ROM) and/or other static storage device coupled to the processor bus 4512 for storing static information and instructions for the processors 4502-4506. The system set forth in FIG. 45 is but one possible example of a computer system that may employ or be configured in accordance with aspects of the present disclosure.

According to one embodiment, the above techniques may be performed by computer system 4500 in response to processor 4504 executing one or more sequences of one or more instructions contained in main memory 4516. These instructions may be read into main memory 4516 from another machine-readable medium, such as a storage device. Execution of the sequences of instructions contained in main memory 4516 may cause processors 4502-4506 to perform the process steps described herein. In alternative embodiments, circuitry may be used in place of or in combination with the software instructions. Thus, embodiments of the present disclosure may include both hardware and software components.

A machine readable medium includes any mechanism for storing or transmitting information in a form (e.g., software, processing application) readable by a machine (e.g., a computer). Such media may take the form of, but is not limited to, non-volatile media and volatile media and may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 606 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in main memory 4516, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

Embodiments of the present disclosure include various steps, which are described in this specification. The steps may be performed by hardware components or may be embodied in machine-executable instructions, which may be used to cause a general-purpose or special-purpose processor programmed with the instructions to perform the steps. Alternatively, the steps may be performed by a combination of hardware, software and/or firmware.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations together with all equivalents thereof.

I claim:

1. A surgical system comprising:
a computing device comprising:
one or more processors;
a communication interface receiving a plurality of two-dimensional images of a patient's joint the subject of a joint arthroplasty procedure; and
at least one memory storing non-transitory computer-readable instructions that, when executed by the one or more processors, cause the computing device to:
generate, based on locating a plurality of mating shapes within the plurality of two-dimensional images of the patient's joint, one or more dimensions for a customized registration guide for the patient's joint for use during the joint arthroplasty procedure, the customized registration guide comprising one or more drill bit guides;
a plurality of registration pins configured to be mounted to the patient's anatomy based on the one or more drill bit guides of the customized registration guide; and
a robotic device comprising:
a controller base unit configured to activate a first link joint of the controller base and a second link joint of the controller base, the second link joint distinct from the first link joint;
a mounting device configured to be mounted to the plurality of registration pins and mechanically coupled with the first link joint of the controller base unit via a plurality of configurable links comprising at least a translational link configured to translate with two degrees of freedom transversal to each other to orient the controller base unit in relation to the mounting device and corresponding to the joint arthroplasty procedure; and
a configurable resection guide mechanically coupled with the second link joint of the controller base unit and oriented to provide a resection guide for the joint arthroplasty procedure;
wherein the first link joint provides one degree of rotational freedom between the mounting device and the controller base unit and the second link joint provides one degree of rotational freedom between the resection guide and the controller base unit.

2. The surgical system of claim 1, wherein the plurality of configurable links further comprises:
a rotational link mechanically coupled with the translational link and configured to rotate the mounting device in relation to a linear link.

3. The surgical system of claim 1, wherein the plurality of configurable links further comprises:
a second rotational link in mechanical communication with the first rotational link and configured to rotate the mounting device in relation to the first rotational link.

4. The surgical system of claim 1, wherein the first link joint and the second link joint are each mechanically coupled with one of a plurality of activators.

5. The surgical system of claim 4, wherein the controller base unit further comprises:
a communication port receiving instructions to control the plurality of activators according to the joint arthroplasty procedure.

6. The surgical system of claim 4, wherein the controller base unit further comprises:
an input device receiving inputs to control the plurality of activators.

7. The surgical system of claim 1, wherein the joint arthroplasty procedure comprises an intra-operative, soft-tissue gap balancing for both static and dynamic motion of the patient's anatomy.

8. The surgical system of claim 1, wherein the robotic device is configurable with one of two-degrees, three-degrees, four-degrees, five-degrees, or six-degrees of freedom.

9. The surgical system of claim 1 wherein the plurality of configurable links are detachable from the first link joint of the controller base unit while the mounting device is mounted to the patient's anatomy.

10. The surgical system of claim 1, wherein the plurality of two-dimensional images of the patient's anatomy comprises a plurality of magnetic-resonance images.

* * * * *